US012653873B2

(12) United States Patent
Kallikourdis et al.

(10) Patent No.: US 12,653,873 B2
(45) Date of Patent: Jun. 16, 2026

(54) PEPTIDE ANTIGENS AND USES THEREOF

(71) Applicants: HUMANITAS MIRASOLE S.P.A., Milan (IT); HUMANITAS UNIVERSITY, Milan (IT)

(72) Inventors: Marinos Kallikourdis, Milan (IT); Elisa Martini, Saronno (IT); Gianluigi Condorelli, Milan (IT)

(73) Assignees: HUMANITAS MIRASOLE S.P.A., Milan (IT); HUMANITAS UNIVERSITY, Milan (IT)

( * ) Notice: Subject to any disclaimer, the term of this patent is extended or adjusted under 35 U.S.C. 154(b) by 1038 days.

(21) Appl. No.: 17/634,191

(22) PCT Filed: Aug. 7, 2020

(86) PCT No.: PCT/EP2020/072239
§ 371 (c)(1),
(2) Date: Feb. 9, 2022

(87) PCT Pub. No.: WO2021/028337
PCT Pub. Date: Feb. 18, 2021

(65) Prior Publication Data
US 2022/0323557 A1 Oct. 13, 2022

(30) Foreign Application Priority Data
Aug. 9, 2019 (IT) ........................ 102019000014541

(51) Int. Cl.
| | |
|---|---|
| A61K 39/00 | (2006.01) |
| A61K 9/00 | (2006.01) |
| A61P 9/04 | (2006.01) |
| A61P 37/06 | (2006.01) |
| C07K 14/47 | (2006.01) |
| C07K 14/705 | (2006.01) |
| C07K 19/00 | (2006.01) |
| C12N 9/86 | (2006.01) |
| G01N 33/68 | (2006.01) |

(52) U.S. Cl.
CPC .......... *A61K 39/001* (2013.01); *A61K 9/0053* (2013.01); *A61P 9/04* (2018.01); *A61P 37/06* (2018.01); *C07K 14/4703* (2013.01); *C07K 14/705* (2013.01); *C07K 14/70596* (2013.01); *C07K 19/00* (2013.01); *C12N 9/86* (2013.01); *C12Y 305/02002* (2013.01); *C12Y 306/03014* (2013.01); *G01N 33/6893* (2013.01); *A61K 2039/542* (2013.01); *G01N 2800/325* (2013.01)

(58) Field of Classification Search
CPC .......... A61K 2039/542; A61K 39/0005; A61K 39/001; A61K 9/0053; A61P 9/04; C07K 14/70596; C07K 14/4703; C07K 14/705
See application file for complete search history.

(56) References Cited

U.S. PATENT DOCUMENTS

2014/0271694 A1 9/2014 Lipes

FOREIGN PATENT DOCUMENTS

| | | | | |
|---|---|---|---|---|
| CN | 105001341 | 10/2015 | | |
| KR | 20120094711 | 8/2012 | | |
| WO | WO-2010115141 A2 * | 10/2010 | ............. | G16B 15/00 |
| WO | 2015031645 A1 | 3/2015 | | |

OTHER PUBLICATIONS

Thandavarayan R A et al, "14-3-3 protein regulates Ask1 signaling and protects against diabetic cardiomyopathy", May 1, 2008 (May 1, 2008), vol. 75, No. 9, p. 1797-1806.
Ritu Chakravarti et al., "14-3-3 in thoracic aortic aneurysms", Arthritis & Rheumatology, vol. 67, No. 7, Jul. 2015 (Jul. 2015), p. 1913-1921.
Jafarzadeh Abdollah et al, "High serum levels of rheumatoid factor and anti-phosphatidylserine antibody in patients with ischemic heart disease", Iranian Journal of Immunology : IJI,,vol. 8, No. 1, Mar. 1, 2011 (Mar. 1, 2011), p. 34-44.
Li, J., et al., "Exploring the causal relationship between immune cell and all-cause heart failure: a Mendelian randomization study", Frontiers, Cardiovasc. Med., Jun. 13, 2024, pp. 1-11.
Daou, D., et al., "Inflammatory Mechanisms in Heart Failure with Preserved Ejection Fraction", Physiology, Apr. 4, 2023, pp. 217-230, vol. 38.
Niebauer, J., et al., "Endotoxin and immune activation in chronic heart failure: a prospective cohort study" The Lancet, May 29, pp. 1838-1842, vol. 353, No. 9167.
Xu, X., et al, "Use of a Liver-Targeting Immune-Tolerogenic mRNA Lipid Nanoparticle Platform to Treat Peanut-Induced Anaphylaxis by Single- and Multiple-Epitope Nucleotide Sequence Delivery", ACS Nano, Mar. 14, 2023, pp. 4942-4957, vol. 17, No. 5.

* cited by examiner

*Primary Examiner* — Bao Q Li
(74) *Attorney, Agent, or Firm* — Gregory P. Einhorn; Greer, Burns & Crain, Ltd.

(57) ABSTRACT

The invention provides a new method for identifying peptide antigens relevant to a non-autoimmune disease involving T cell activation as well as novel peptides identified therefrom. The isolated peptides of the invention are useful in the diagnosis, prevention and/or treatment of a cardiovascular disease, more specifically heart failure (HF). The invention further provides a pharmaceutical composition comprising at least one isolated peptide of the invention and a pharmaceutically acceptable carrier, vehicle, excipient and/or diluent. The pharmaceutical composition of the invention is suitable to be orally administered as a tolerizing vaccine.

11 Claims, 12 Drawing Sheets
Specification includes a Sequence Listing.

| Gene | fasta | qstart | qend | peptide | length | # peptides | Homology with Human | |
|---|---|---|---|---|---|---|---|---|
| Adrb1 | MGAGALALGASEPCNLSSAAPLPDGAAT AARLLVLASPPASLLPPASEGSAPLSQQWT AGMGLLLALIVLLIVVGNVLVIVAIAKTPRL | 50 | 71 | SAPLSQQWTAGMGLLLAL IVLL | 21 | 2 | 100% NP_000675.1 | GROUP 3 |
| Adrb1 | MGAGALALGASEPCNLSSAAPLPDGAAT AARLLVLASPPASLLPPASEGSAPLSQQWT AGMGLLLALIVLLIVVGNVLVIVAIAKTPRL | 310 | 327 | KALKTLGIIMGVFTLCWL | 17 | 2 | 100% NP_000675.1 | |
| Adrb1 | MGAGALALGASEPCNLSSAAPLPDGAAT AARLLVLASPPASLLPPASEGSAPLSQQWT AGMGLLLALIVLLIVVGNVLVIVAIAKTPRL | 339 | 354 | HRDLVPDRLFVFFNWL | 15 | 1 | 93% NP_000675.1 | |
| 14-3-3 | MDDREDLVYQAKLAEQAERYDEMVESM KKVAGMDVELTVEERNLLSVAYKNVIGAR RASWRIISSIEQKEENKGGEDKLKMIREYR | 171 | 185 | LGLALNFSVFYEIL | 14 | 1 | 100% NP_001129174.1 | GROUP 4 |
| Snrpd1 | MKLVRFLMKLSHETVTIELKNGTQVHGTI TGVDVSMNTHLKAVKMTLKNREPVQLET LSIRGNNIRYFILPDSLPLDTLLVDVEPKVK | 51 | 75 | EPVQLETLSIRGNNIRYFILP DSLP | 24 | 4 | 100% NP_008869.1 | |
| Atp5o | MAAPAASGLSRQVRSFSTSVVRPFAKLVR PPVQVYGIEGRYATALYSAASKEKKLDQVE KELLRVGQLLKDPKVSLAVLNPYIKRTVKV | 104 | 118 | LTANLMNLLAENGRL | 14 | 1 | 87% NP_001688.1 | |

FIG. 4

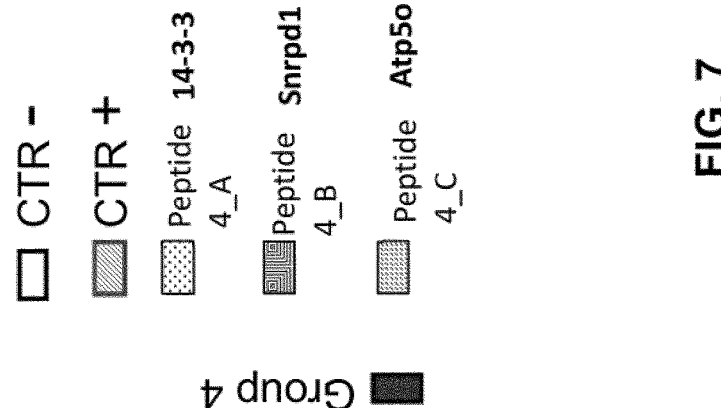
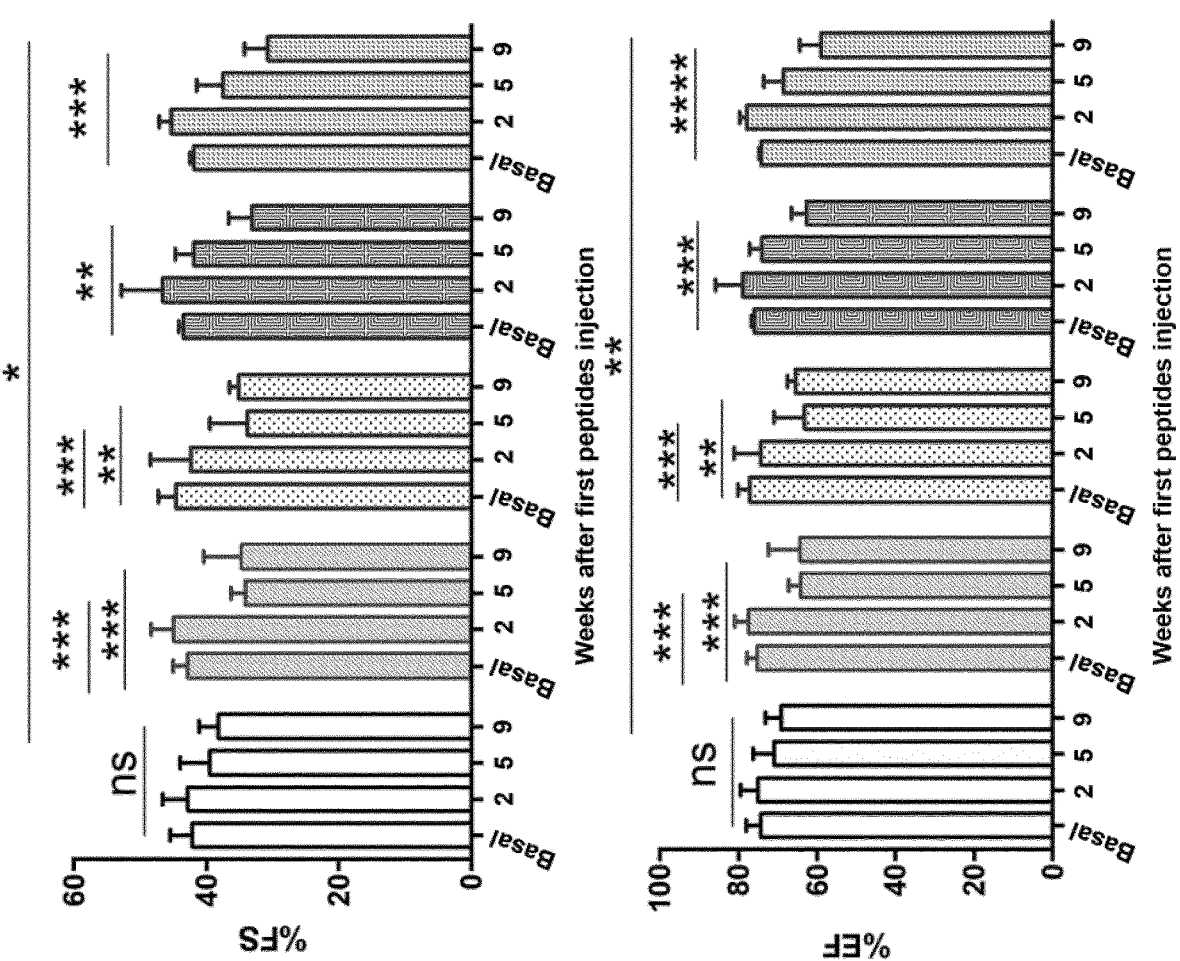
FIG. 7

PEPTIDE ANTIGENS AND USES THEREOF

RELATED APPLICATIONS

This application is a national phase application claiming benefit of priority under 35 U.S.C. § 371 to Patent Convention Treaty (PCT) International Application serial number PCT/EP2020/072239, filed Aug. 7, 2020, now pending, which claims the benefit of priority to Italian patent No. 102019000014541 filed on Aug. 9, 2019. The aforementioned applications are expressly incorporated herein by reference in their entirety and for all purposes.

TECHNICAL FIELD

The present invention relates to a new method for identifying peptide antigens relevant to a disease involving T cell activation as well as novel peptides identified therefrom. The isolated peptides of the invention are useful in the diagnosis, prevention and/or treatment of a cardiovascular disease, more specifically heart failure (HF).

BACKGROUND

The immune system has evolved in response to the threat of invading pathogens. Its first line of defense is innate immunity and the innate immune system, including macrophages, neutrophils and monocytes, which is rapid but non-specific. Innate immune cells can eliminate pathogens, whilst they respond to and also release in a positive feedback loop, pro-inflammatory cytokines.

Adaptive immunity and the adaptive immune system (composed of T and B lymphocytes, termed T and B cells) is utilized to deal with persistent pathogens. It requires several days to become activated. T and B cells have a key feature that distinguishes them from innate immune cells. They express antigen receptors: T cell receptor (TCR) on T cells and B cell receptor (BCR) on B cells. The TCR and BCR have binding sites of variable sequence, unique in every different T cell or B cell, the result of a variability-generating somatic recombination process. As a result, each different T or B cell will have TCRs or BCRs with unique binding sequence, that bind antigens, i.e. mostly protein fragments that are present on invading pathogens. Thus, a population of T and B cells with a repertoire of variable antigen specificities will enable recognition and initiation of a response specific for any possible invading pathogen. This specificity, coupled with lymphocyte longevity, enables T and B cells to maintain long-lasting memory responses, a feature that enables vaccines to function. In the unfortunate case where the antigen does not belong to an invading pathogen, but it is expressed by the body's own cells, the adaptive response allows autoimmunity to occur (Kallikourdis M, (2018) "T cell responses to tumor: how dominant assumptions on immune activity led to a neglect of pathological functions, and how evolutionary considerations can help identify testable hypotheses for improving immunotherapy", Cancer Immunol Immunother. 67(6):989-998). In this case, the memory capacity of the T and B cells, coupled to the persistence of the self-antigen, which cannot be destroyed without destroying the organism, renders the disease chronic. These chronic processes, thus, are involved in the erroneous immune responses against the self, which occurs in autoimmunity. Yet these processes have now also been found to contribute to many other high-morbidity and high-mortality diseases.

To classify as autoimmunity, a disease must satisfy a number of criteria, a summary of which is:

(i) the disease must be demonstrated to be transferrable if one transfers T cells from a sick individual to a healthy individual;

(ii) the disease must be demonstrated to be transferrable if one transfers (auto)antibody-containing serum from a sick individual to a healthy individual;

(iii) the disease must be demonstrated to be inducible if one immunizes a healthy individual with the self-antigens against which the autoimmune T cells and B cells are responding to.

The above-illustrated criteria are well-known (Rose, N. R. et al. (1993) "Defining criteria for autoimmune diseases", Immunology today: 426-430).

Acquired diseases, such as, for example, heart failure and Alzheimer's disease, which usually appear with aging, are not generated as a result of an erroneous autoreactive T cell or B cell response, rather arise as a result of stress within the affected tissue. Therefore, these diseases are not considered autoimmune. For instance, in the case of heart disease, stress in the heart can arise from a number of lifestyle- or environment-related risk factors, such as unhealthy diet (Type 2 Diabetes) or high blood pressure, which damage the cardiomyocytes, setting off a pathogenic process (Bui, A. L. et al. (2011), "Epidemiology and risk profile of heart failure", Nat Rev Cardiol, 8 (1), 30-41).

In the last decades, scientific work has revealed that adaptive immunity plays a role in the processes mediating the effects of many ailments in humans, from metabolic disorders, to cancer, age-related diseases and neurodegenerative/neurological disorders. Cardiovascular disease (CVD) is no exception (Ait-Oufella H. et al., (2006) "Natural regulatory T cells control the development of atherosclerosis in mice", Nat. Med., 12(2), 178-80). Adaptive immunity may have a feature that renders it especially susceptible to non-optimized function, especially in middle- to late-age diseases. Aluvihare V R et al., (2004) "Regulatory T cells mediate maternal tolerance to the fetus" Nat Immunol, 5(3), 266-71 has previously demonstrated that mammals require the anti-inflammatory arm of adaptive immunity, the regulatory T cells (Treg), in order to be able to reproduce via placental pregnancy. This is because the fetus is immunologically half-father. Without an egg to separate them, the pro-inflammatory arm of the maternal adaptive immune system would recognize the fetus as foreign and eliminate it. Treg actively and specifically suppresses this rejection. Importantly, the fully functional form of Treg only evolved in monotremes, which are egg-laying mammals, and in mammals, suggesting that reproduction may have been a key evolutionary driver for the development of the immunosuppressive arm of adaptive immunity. A corollary of this postulate is that little evolutionary pressure may be exerted on adaptive immunity after the reproductively active age of females. Thus, adaptive immunity may act non-optimally in any disease that has high incidence late in life, after the age range when reproduction usually occurs. Whilst the same argument can be applied to a lesser extent to innate immunity, the pregnancy-specific function of adaptive immunity produces a cliff-edge effect at middle age, and effects were identified in autoimmunity (Munoz-Suano A. et al, (2012) "Regulatory T cells protect from autoimmune arthritis during pregnancy", J Autoimmun, 38(2-3), J103-8), age-related inflammation (Benedusi, V, et al. (2015), "Ovariectomy shortens the life span of female mice", Oncotarget, 6(13), 10801-11), cancer (Kallikourdis M, (2018) "T cell responses to tumor: how dominant assumptions on immune activity led to a neglect of pathological functions, and how evolutionary considerations can help identify testable hypotheses for improving immunotherapy", Cancer Immunol Immunother. 67(6):989-998), and in the last four years, Heart Failure (HF) (Kallikourdis, M, et al. (2017), "T cell costimulation blockade blunts pressure overload-induced heart failure", Nat Commun, 8 14680). Most CVD ailments are associated with aging and inflammation, fitting this pattern. Thus, non-optimal function of adaptive immunity may contribute to CVD, thereby offering an efficient therapy target, especially given the role of adaptive immunity in regulating the chronic nature of immune responses, as well as to all the diseases associated with inflammation, such as e.g. metabolic diseases (diabetes not type 1, metabolic syndrome), obesity, neurodegenerative and neurological diseases (Amyotrophic Lateral Sclerosis-ALS, Alzheimer's Disease, Dementia, Age-related Dementia, Mild Cognitive Decline, Parkinson's Disease), and old-age-related diseases.

Cardiovascular diseases, neurodegenerative diseases and cancer are key causes of morbidity and mortality. Importantly, ailments from these three groups of diseases often appear in the clinic simultaneously, in a condition termed multimorbidity. Multimorbidity is an increasingly evident clinical problem, often very difficult to both diagnose and treat, as the division of healthcare into specialized disciplines renders cross-discipline diagnosis almost impossible to apply.

Multimorbidity condition may be either due to tissue degeneration leading to multi-system dysregulation, or it may be iatrogenic, i.e. caused by effects of a drug on a tissue different from the target tissue of the initial disease. Indeed, as more "biological" drugs enter clinical practice, one cannot exclude the possibility that aspects of multimorbidity can occasionally even be iatrogenic, i.e. caused by side-effects of pharmacological treatment. This is because current clinical practice has been developed around single disease-patients, often with little understanding of "off-target" effects. With biological and immunomodulating drugs, "off-target" effects may indeed be legitimate effects of the drugs' mechanism of action, albeit on off-target tissues. Hence, incomplete consideration of these effects may contribute to multimorbidity. Evidence suggests that inflammation and immune responses are implicated in the pathogenesis of all three disease groups listed above. The inherent mobility of the immune system, and its association with most chronic disease forms, renders it a potential contributing mechanism (a "common denominator") of multimorbidity.

As an example, very recent clinical observations have brought to light that cancer patients undergoing immunotherapy to unleash the activity of their T cells against a tumor, occasionally suffer from T cell- and macrophage-mediated lethal myocarditis (Heinzerling, L, et al. (2016), "Cardiotoxicity associated with CTLA4 and PD1 blocking immunotherapy", J Immunother Cancer, 4 50; Johnson, D B, et al. (2016), "Fulminant Myocarditis with Combination Immune Checkpoint Blockade", N Engl J Med, 375(18), 1749-55). As tumor immunotherapy is increasingly applied in the clinic, this may represent an emergent, iatrogenic, immune system-dependent form of multimorbidity involving cancer and cardiac disease.

Heart Failure (HF) is the end stage of several cardiac diseases. It can occur as a result of volume or pressure overload, brought about by aortic stenosis or hypertension or other causes. Alternatively, it can occur as a result of cardiomyocyte damage, brought about by genetic mutations or by myocardial infarction (MI) injury. HF can be characterized by a reduction in left ventricle ejection fraction (HFrEF) or preserved ejection fraction (HFpEF), the two conditions being currently roughly equally prevalent among patients. The defects in cardiac functionality are observed as systolic and/or diastolic ventricular function. A small percentage (<5%) of HF cases are the result of inflammatory myocarditis, a cardiac inflammation that is the result of autoimmune responses or immune responses to viruses infecting the heart.

Clinical data generated in the last two decades show that pressure overload HF and MI-induced HF are also characterized by inflammation, as the stressed cardiomyocytes release pro-inflammatory cytokines such as TNFa, IL1b and IL6 (Shioi, T, et al. (1997), "Increased expression of interleukin-1 beta and monocyte chemotactic and activating factor/monocyte chemoattractant protein-1 in the hypertrophied and failing heart with pressure overload", Circ Res, 81(5), 664-71; Hofmann, U and S Frantz (2013), "How can we cure a heart "in flame" ? A translational view on inflammation in heart failure", Basic Res Cardiol, 108(4), 356). This is in agreement with the observation that during pathological hypertrophy, a state preceding HF, a key event in the ailing heart is fibrosis, which is an immune-mediated phenomenon (Wynn, T A (2003), "IL-13 effector functions", Annu Rev Immunol, 21: 425-56). Cells of the innate immune system (macrophages) have been found to contribute to pathological cardiac inflammation (Mann, D L (2015), "Innate Immunity and the Failing Heart: The Cytokine Hypothesis Revisited", Circ Res, 116(7), 1254-68; Patel, B, et al. (2018), "CCR2+ Monocyte-Derived Infiltrating Macrophages Are Required for Adverse Cardiac Remodeling During Pressure Overload", JACC Basic Transl Sci, 3(2), 230-44).

Early attempts to therapeutically block cytokine function (TNFa) in HF failed, for various reasons, possibly including the redundancy of pro-inflammatory cytokine function. The extension of pro-inflammatory cytokine studies have more recently led to more successful clinical trials using inhibition of IL1b in a cardiac disease context (Ridker, P M, et al. (2017), "Anti-inflammatory Therapy with Canakinumab for Atherosclerotic Disease", N Engl J Med, 377(12), 1119-31). Yet this effect was still not efficient enough to warrant FDA approval.

However, as inflammation is demonstrably involved in the progression of HF, a better therapeutic target that can inhibit the deleterious inflammatory process would still have substantial potential for clinical benefit.

As outlined above, adaptive immune cells (T and B cells) act in an antigen-specific and chronic manner, meaning that they may be key regulators of long-lasting responses and thus of the diseases which involve them, such as chronic conditions, for example HF (including pressure overload-induced HF, congestive HF, age-related HF). Indeed, Nevers and co-workers (Nevers, T, et al. (2015), "Left Ventricular T-Cell Recruitment Contributes to the Pathogenesis of Heart Failure", Circ Heart Fail, 8(4), 776-87), and Laroumanie and co-workers (Laroumanie, F, et al. (2014), "CD4+ T cells promote the transition from hypertrophy to heart failure during chronic pressure overload", Circulation, 129(21), 2111-24) recently demonstrated that ablation of T cells, either in gene-deficient mice or by antibody depletion, had protective effects from HF induced by Transverse Aortic Constriction (TAC), the gold-standard mouse model for the preclinical study of HF (Rockman, H A, et al. (1991), "Segregation of atrial-specific and inducible expression of an atrial natriuretic factor transgene in an in vivo murine model of cardiac hypertrophy", Proc Natl Acad Sci USA, 88(18), 8277-81). In parallel, Kallikourdis and co-workers (Kallikourdis, M, et al. (2017), "T cell costimulation block-
ade blunts pressure overload-induced heart failure", Nat
Commun, 8 14680) demonstrated that inhibition of T cell
activation, via co-stimulation blockade with recombinant
molecule CTLA4-Ig, even if administered late in the course
of disease, can block progression of HF in the TAC model.
The effect obtained was several-fold stronger than that
achieved by standard b-blocker therapy. The cardiotoxic
effect of the T cells involved the action of cardiac macro-
phages and affected the extent of cardiac fibrosis and car-
diomyocyte viability. This was blocked by treatment with T
cell co-stimulation blocker CTLA4-Ig. The presence of T
cells was identified in both biopsies of human patients with
HFrEF as well as HFpEF, whilst T cells are also implicated
in age-related HF. These findings demonstrate that T cells
are necessary for the progression of HF, even when the cause
of HF is not immunological.

This cardiotoxic function of T cells may be inhibited by
anti-inflammatory Treg cells (Kanellakis, P, et al. (2011),
"CD4+CD25+Foxp3+ regulatory T cells suppress cardiac
fibrosis in the hypertensive heart", J Hypertens, 29(9),
1820-28), as well as by the molecule CD73 (Borg, N, et al.
(2017), "CD73 on T Cells Orchestrates Cardiac Wound
Healing After Myocardial Infarction by Purinergic Meta-
bolic Reprogramming", Circulation, 136(3), 297-313). T
cells are also important for the progression of heart failure
following myocardial infarction (Hofmann, U, et al. (2012),
"Activation of CD4+T lymphocytes improves wound heal-
ing and survival after experimental myocardial infarction in
mice", Circulation, 125(13), 1652-63; Weirather, J, et al.
(2014), "Foxp3+CD4+ T Cells Improve Healing after Myo-
cardial Infarction by Modulating Monocyte/Macrophage
Differentiation", Circ Res, 115:55-67).

Despite growing evidence of the cardiotoxic activity of T
cells, the antigen specificity of naturally occurring T cell
responses mediating non-autoimmune heart failure is still
not known.

So far, studies on the antigen specificity of the responses
in heart failure (HF) have mainly focused on autoimmune
myocarditis, which however represents a very small per-
centage (<5%) of HF cases. In this pathology, a defect of the
immune system results in an autoimmune response that
happens to target the heart (Caforio, A L, et al. (1992),
"Identification of alpha- and beta-cardiac myosin heavy
chain isoforms as major autoantigens in dilated cardio-
myopathy", Circulation, 85 (5), 1734-42; Caforio, A L, et al.
(2015), "Passive transfer of affinity-purified anti-heart
autoantibodies (AHA) from sera of patients with myocardi-
tis induces experimental myocarditis in mice", Int J Cardiol,
179 166-77; Basavalingappa, R H, et al. (2016), "Identifi-
cation of an Epitope from Adenine Nucleotide Translocator
1 That Induces Inflammation in Heart in A/J Mice", Am J
Pathol, 186 (12), 3160-75; Krishnan, B, et al. (2017),
"Branched chain α-ketoacid dehydrogenase kinase 111-130,
a T cell epitope that induces both autoimmune myocarditis
and hepatitis in A/J mice", Immun. Inflamm. Dis, 5 (4),
421-34).

US2014/0271694 discloses that the alpha isoform of
myosin heavy chain raises a T cell immune response and
IgG autoantibodies in autoimmune or pathogen-induced
inflammatory cardiovascular diseases such as myocardial-
infarction related autoimmunity (post-infarction autoim-
mune syndrome, PIA) and inflammatory myocarditis.

In other studies aiming at elucidating immune responses
against the heart, artificial model antigens were used, ren-
dering them not relevant to the antigens that "physiologi-
cally" drive responses in heart failure, which arise naturally during the onset of this disease (Gröschel, C, et al. (2017),
"T helper cells with specificity for an antigen in cardiomyo-
cytes promote pressure overload-induced progression from
hypertrophy to heart failure", Sci Rep, 7 (1), 15998).

There is therefore a strong need of providing new effec-
tive therapeutic approaches aiming at preventing the onset of
heart failure or reducing the severity of this disease.

There is also a strong need of providing a diagnostic
method for diagnosing heart failure, particularly heart fail-
ure not resulting from autoimmune myocarditis.

More particularly, there is a need of providing a diagnos-
tic method that enables to ascertain with a high degree of
accuracy the presence of heart failure disease in a subject
and/or the propensity of a subject to develop this disease,
thereby allowing the prescription of lifestyle and/or medi-
cation choices which may further reduce the risk of devel-
oping heart failure.

SUMMARY

These and other needs are met by the method, the isolated
peptide and the diagnostic and therapeutic use thereof as
defined in the appended claims, which form an integral part
of the description.

as discussed in detail in Example 1, below.

Figure 2:
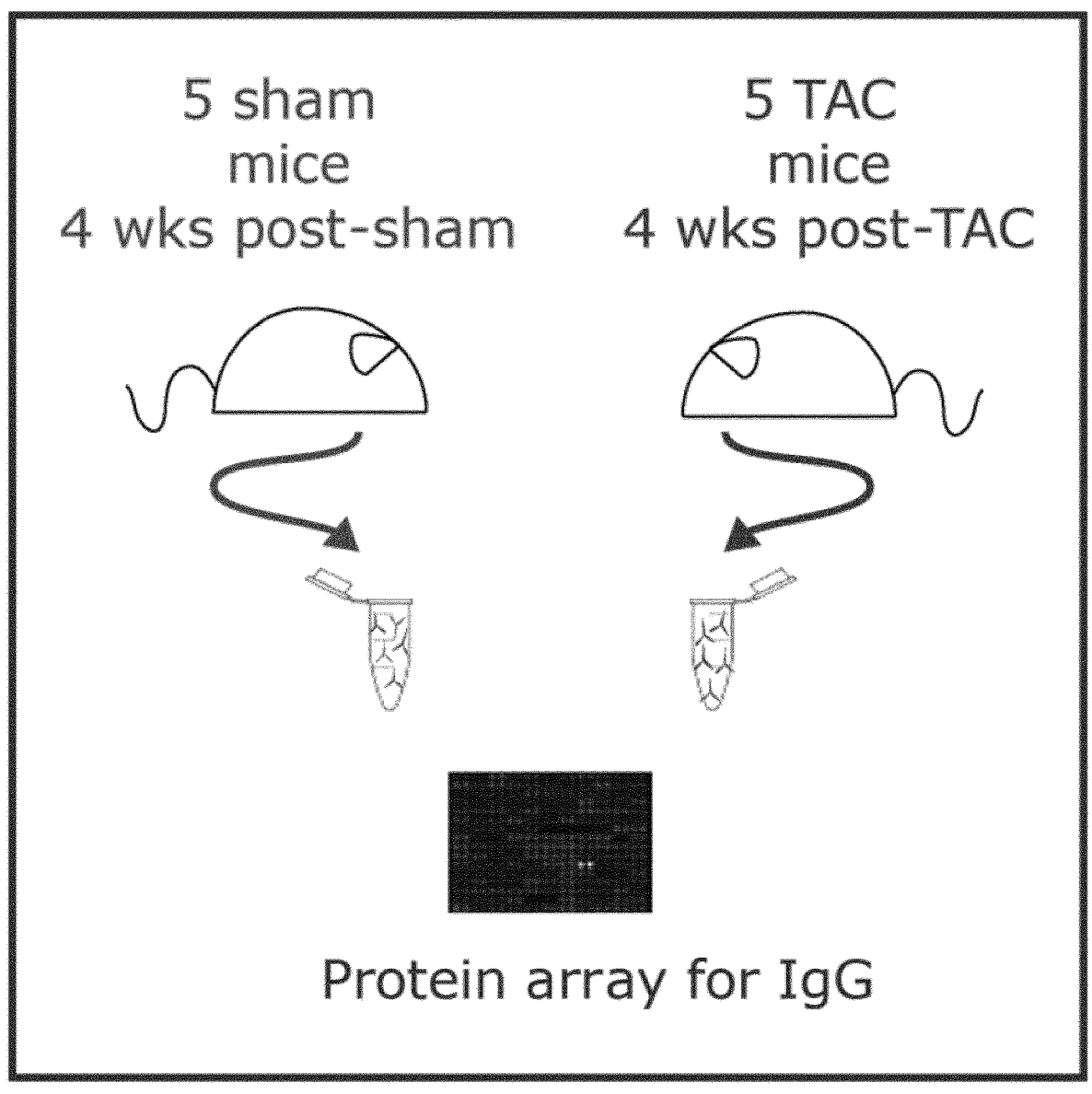

FIG. 2 schematically illustrates an exemplary protocol
where serum samples were collected from 5 sham-operated
mice or 5 TAC-operated mice 4 weeks after sham or TAC
surgery; and the sera were pooled into two samples, respec-
tively (1 TAC and 1 sham); and the pooled serum samples
were assayed on a commercial mouse autoantigen and
random antigen-discovery array, as discussed in detail in
Example 2, below.

Figure 3:
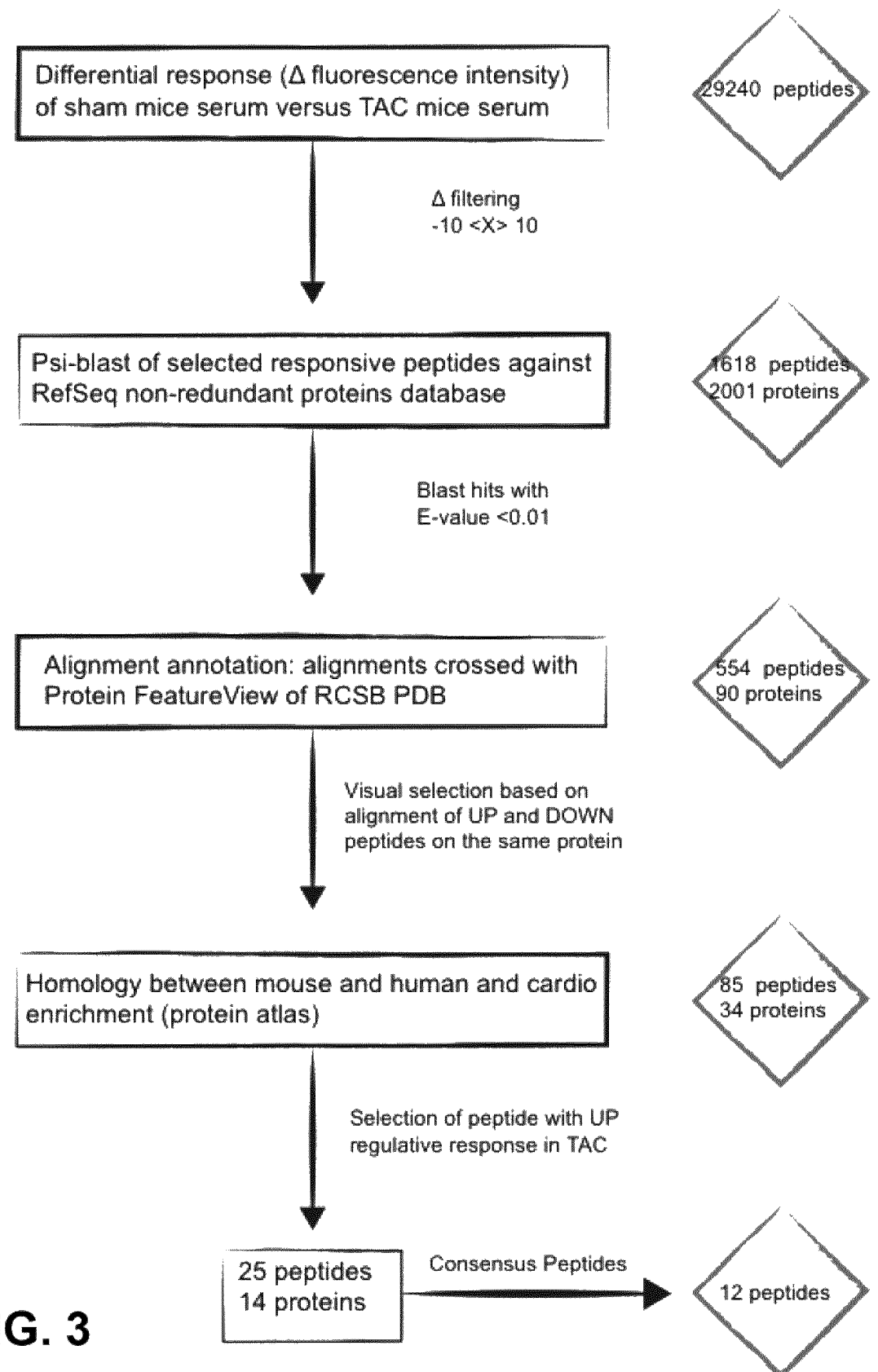

FIG. 3 schematically illustrates an exemplary protocol, a
discovery strategy, having the aim of identifying peptide
antigens driving T cells involved in HF pathology, as dis-
cussed in detail in Example 3, below.

FIG. 4 illustrates in table form peptides identified as
end-results of the above-described process, as discussed in
detail in Example 3, below.

Figure 5:
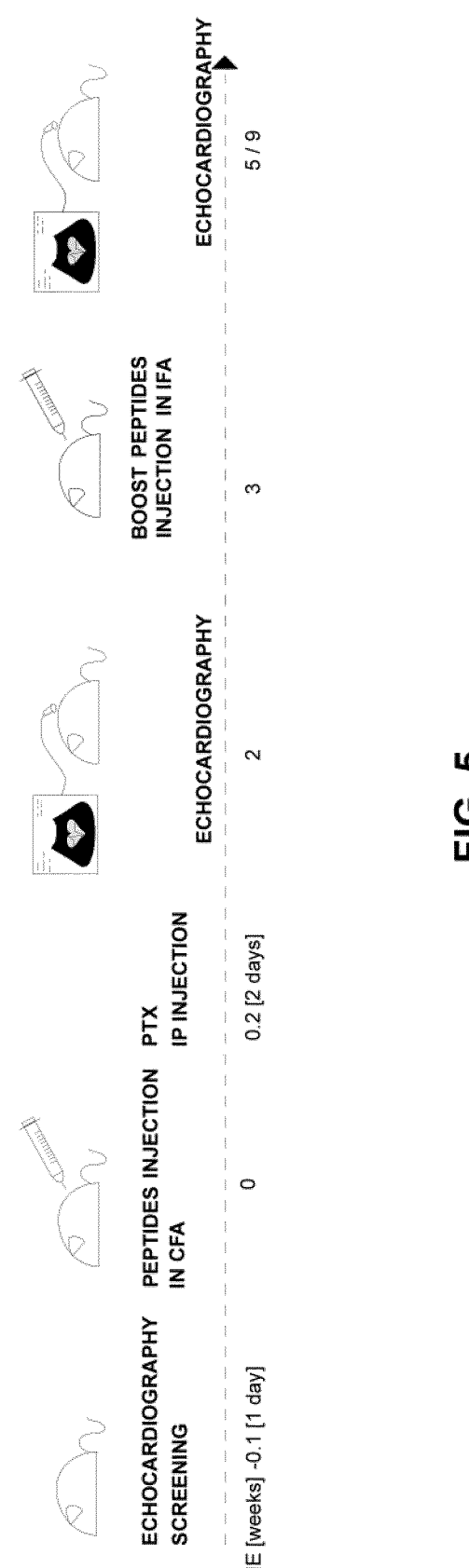

FIG. 5 schematically illustrates an exemplary protocol for
validating the functional relevance of identified antigens
recognized by T cells driving HF, as discussed in detail in
Example 4, below.

Figure 6:
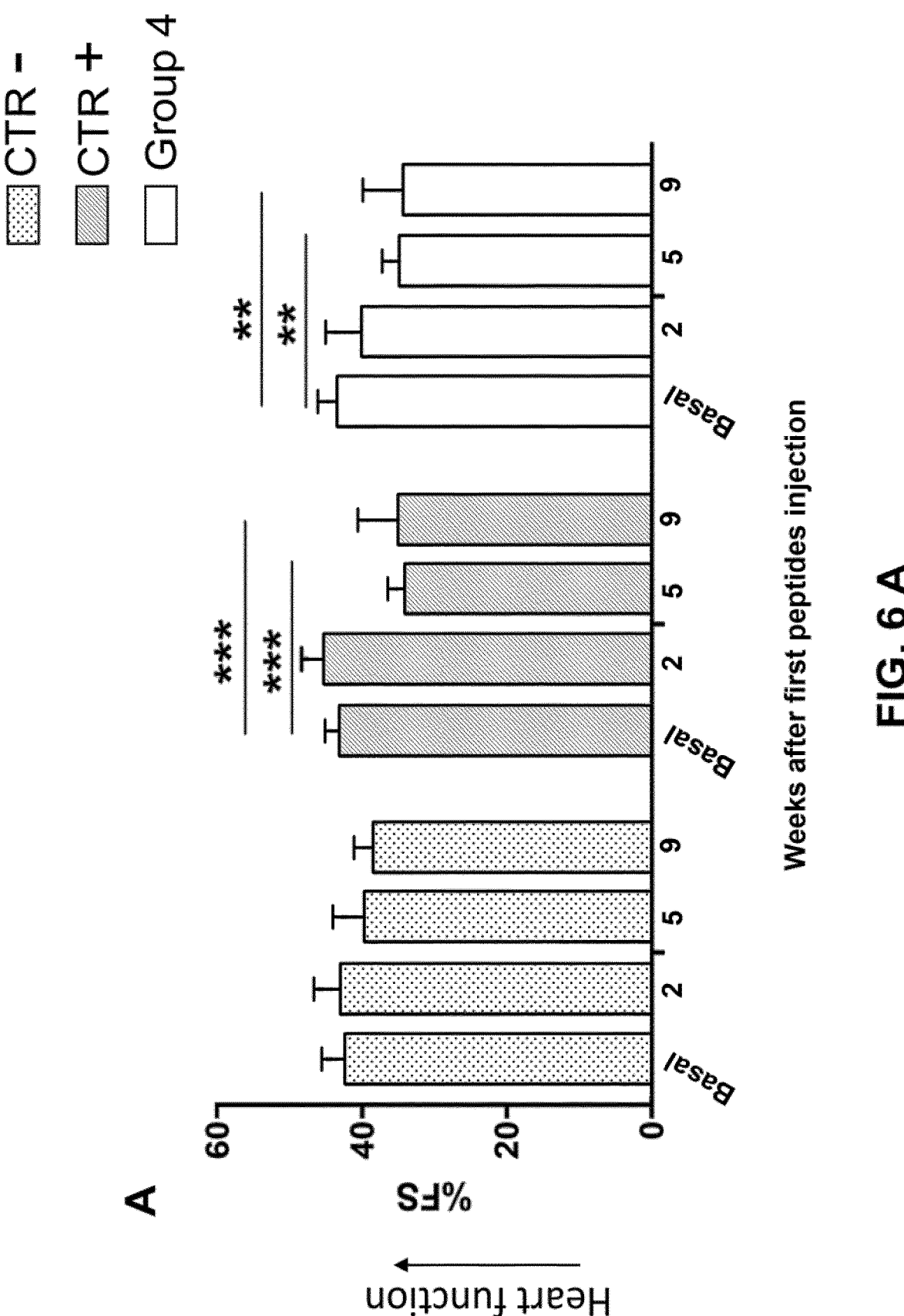
Figure 6:
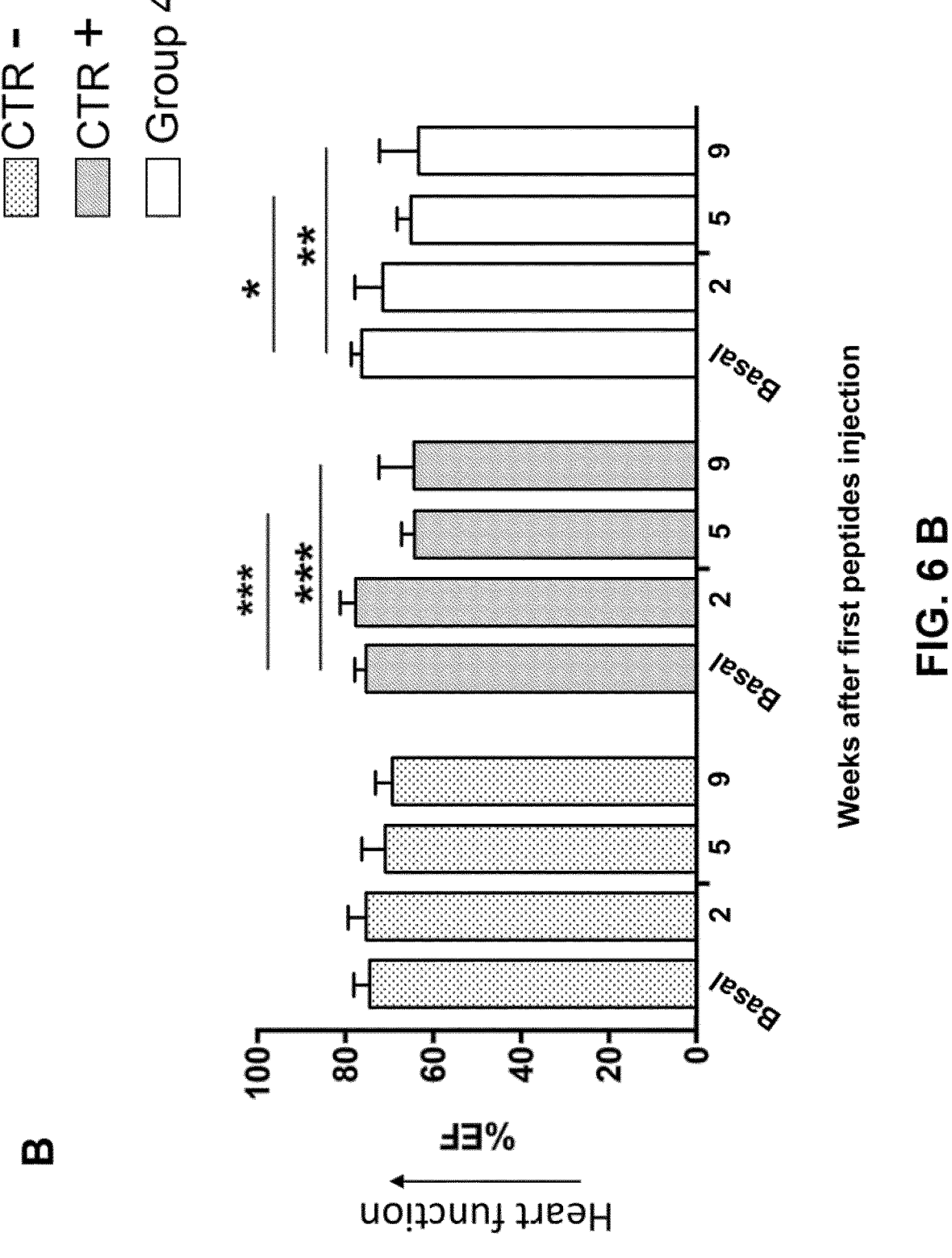

FIG. 6A-B graphically illustrate data showing immuni-
zation experiments of healthy mice with peptides derived
from beta-adrenergic receptor and from 14-3-3, Snrpd1, and
Atp5o lead to cardiac dysfunction; and as shown in the bar graphs of FIG. 6A-B, mice immunized with peptides derived from beta-adrenergic receptor (CTR+) and from 14-3-3, Snrpd1, and Atp5o proteins displayed a significant reduction of cardiac functionality, measured via echocardiography analysis at 2, 5 and 9 weeks after the first subcutaneous injection, %FS heart function FIG. 6A, and %EF heart function FIG. 6B, as discussed in detail in Example 4, below.

FIG. 7 graphically illustrates data showing the results of echocardiography analysis of cardiac functionality parameters %FS (left image) and %EF (right image) of C57BL6/J mice immunized with the peptide of SEQ ID NO. 1 (14-3-3 protein), the peptide of SEQ ID NO. 5 (Snrpd1 protein), or the peptide of SEQ ID NO. 14 (Atp5o protein), as discussed in detail in Example 5, below.

Figure 8:
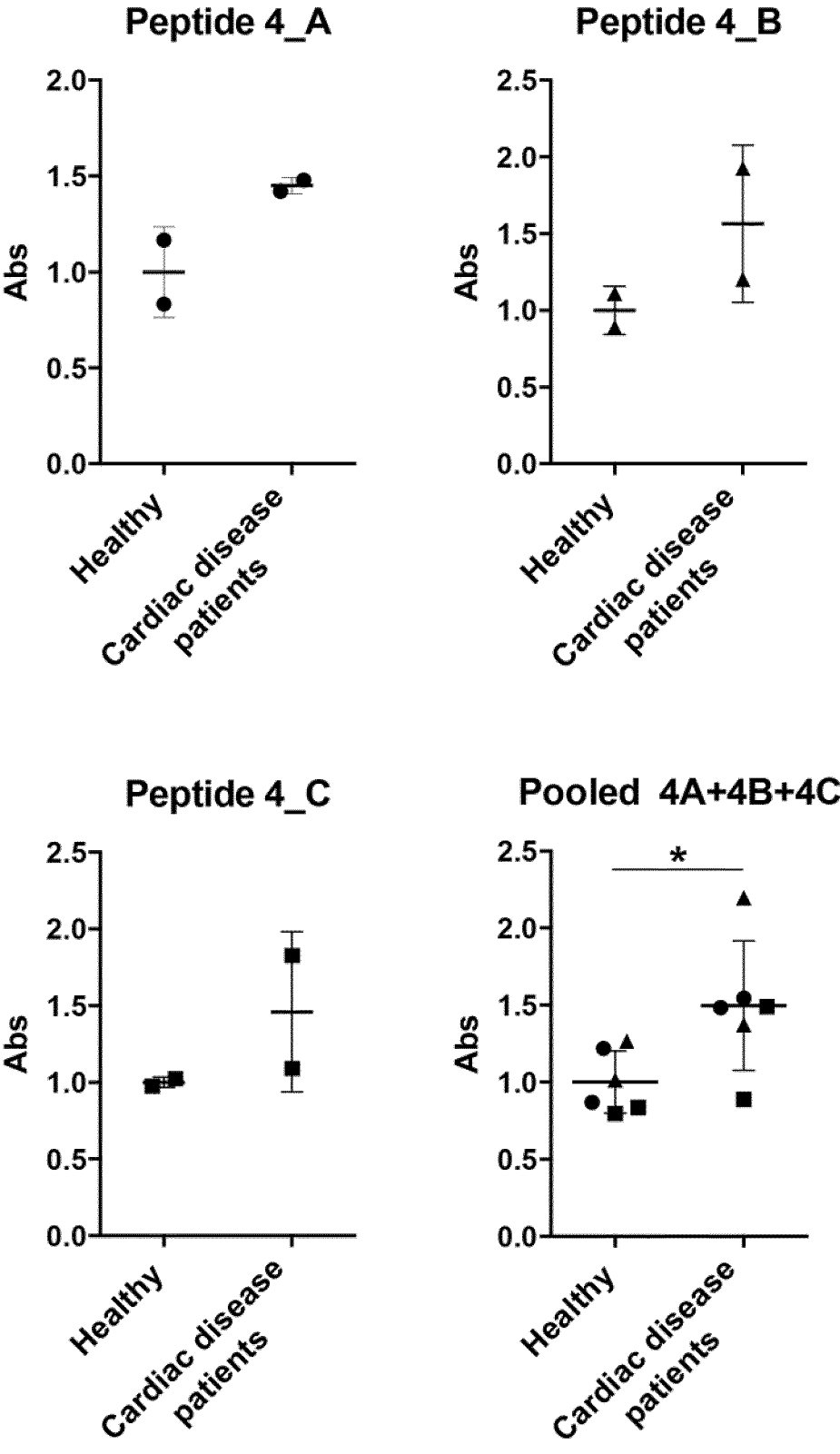

FIG. 8 graphically illustrates data showing the intensity of the colorimetric reaction was measured and the absorbance of samples (upper left image peptide 4A, upper right image peptide 4B, lower left image peptide 4C, lower right image pooled peptides) after blank subtraction was plotted, as discussed in detail in Example 6, below.

Figure 9:
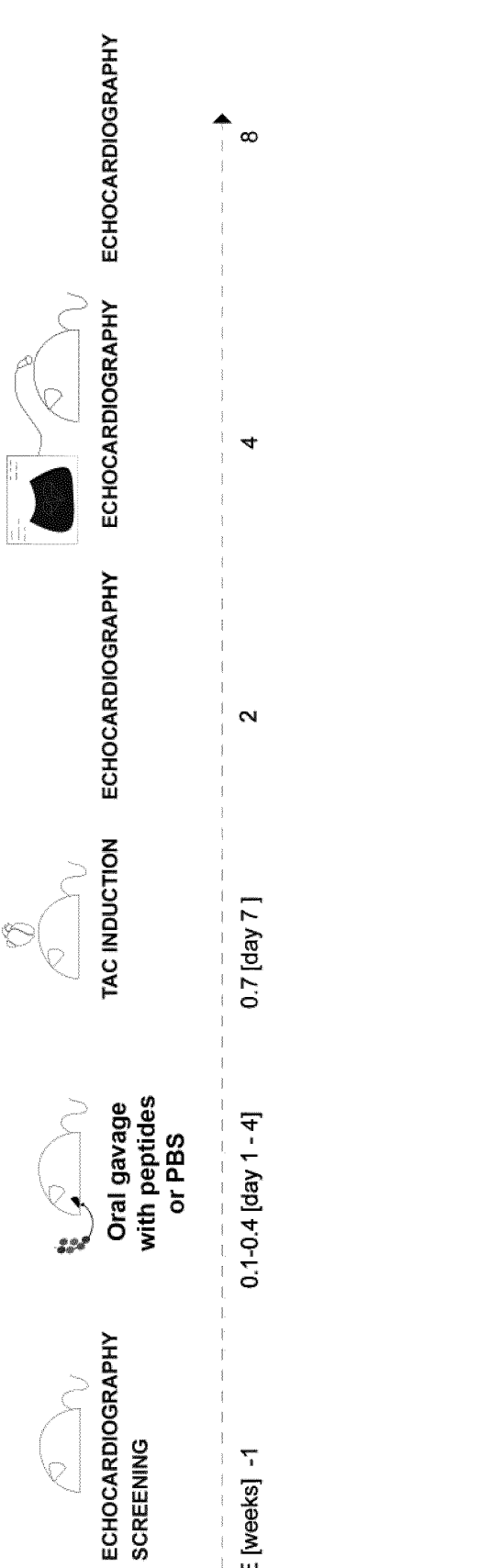

FIG. 9 schematically illustrates an exemplary protocol used to assess preventive protection potential of oral tolerance with the newly identified peptides from the development of Heart Failure; an oral tolerance protocol was used to induce cardio-specific tolerance for the peptides, followed by active induction of Heart Failure via TAC, as discussed in detail in Example 7, below.

Figure 10:
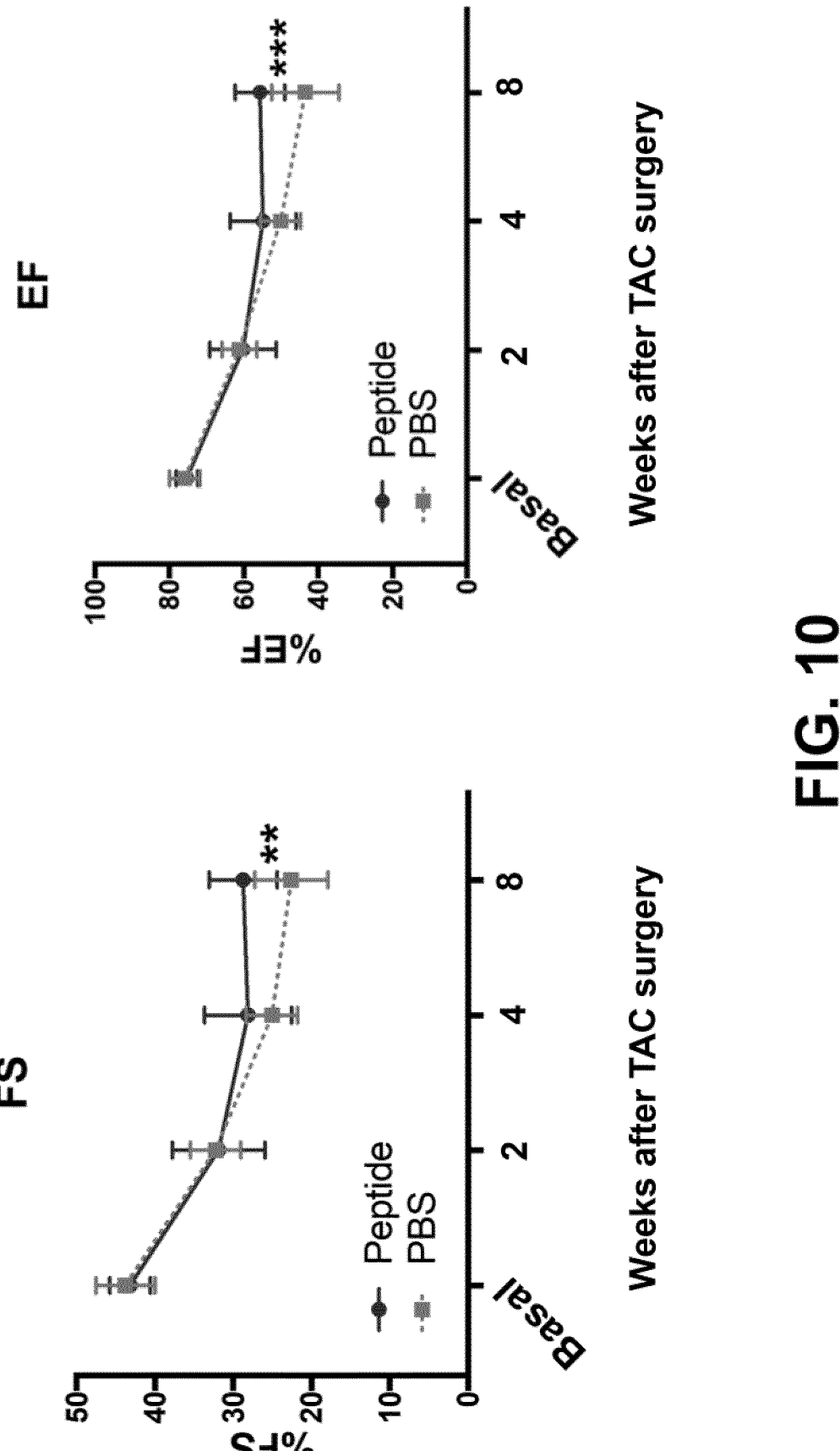

FIG. 10 graphically illustrates data showing the results of oral administration of peptides prevented cardiac dysfunction (%EF upper image, %FS lower image) in TAC-operated mice that orally received the identified peptides (peptides of SEQ ID NO. 1, 5 and 14) with the tolerization protocol as discussed in detail in Example 7, below.

Figure 11:
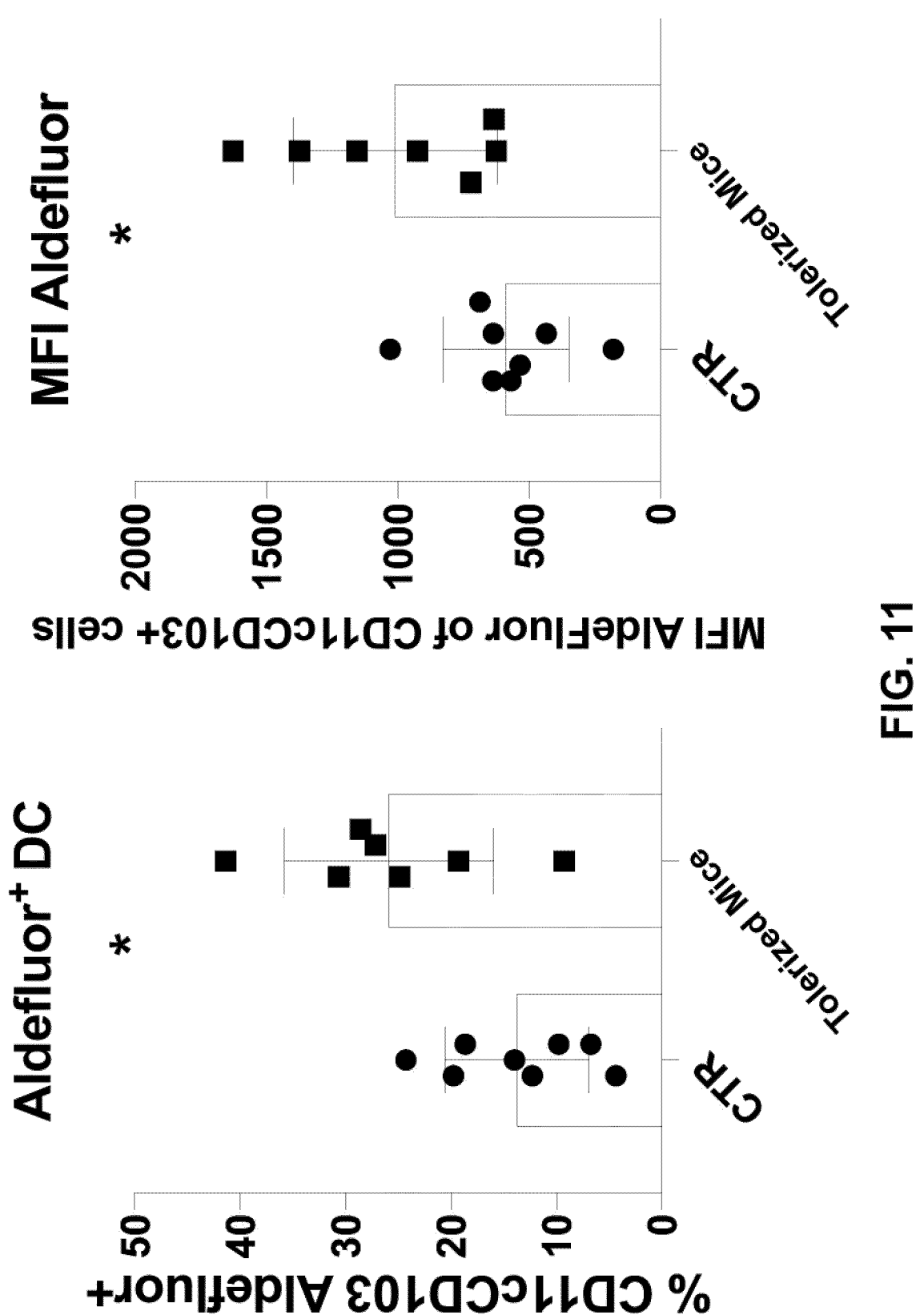

FIG. 11 graphically illustrates data showing aldehyde dehydrogenase (ALDH) production of retinoic acid from the DC as measured via aldefluor fluorescent dye (MRI aldefluor upper image, aldefluor+DC lower image), measuring with a FACS analysis of DC isolated from MLN, and showing that mice fed with the peptides of SEQ ID NO. 1, 5 and 14 showed a significant increase in ALDH activity, as discussed in detail in Example 7, below.

DETAILED DESCRIPTION

Figure 1:
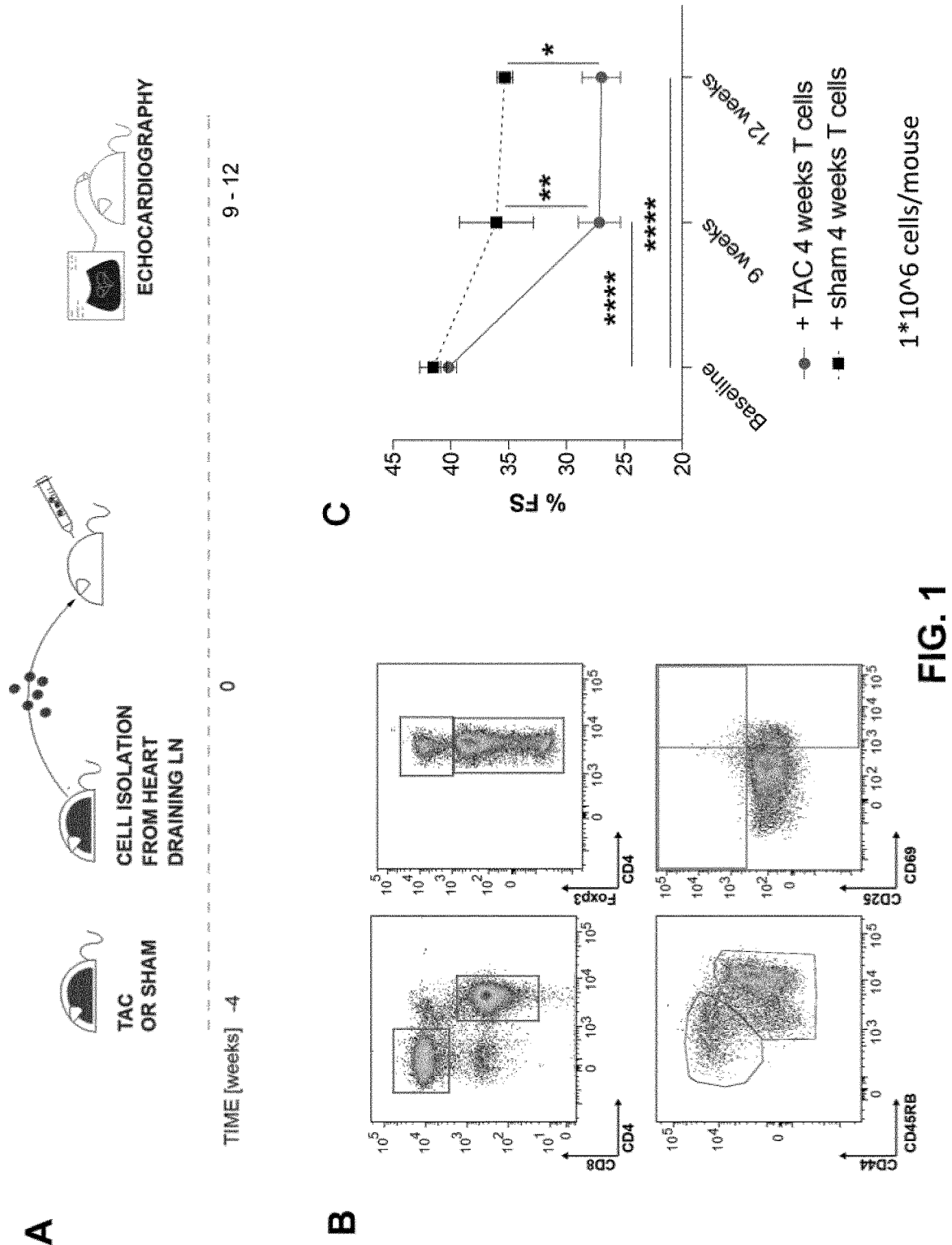
FIG. 1A schematically illustrates the transfer via intrave-
nous injection of T cells taken from cardiopathic mice
subjected to Transverse Aortic Constriction (TAC) to induce
HF, into healthy recipient mice lead to the development of
significant heart dysfunction in the latter, thus indicating the
T-cell dependence of the mechanism of HF progression.
FIG. 1B graphically illustrates data showing that T cells
isolated from lymph nodes included cytotoxic CD8+, CD4+
conventional naïve T cells and CD4+conventional effector T
cells, and regulatory T cells.
FIG. 1C graphically illustrates data showing that mice
that received cells from TAC-operated mice showed a significant decrease of heart
functionality measured as %FS, compared to mice receiving
T cells from control (sham-operated) mice, signifying a
reduction in heart functionality.

As it will be illustrated in more detail in the experimental section that follows, the present inventors have elucidated a primary role of adaptive immunity in the onset and progression of HF, even when the cause for this disease is not an immune defect. More particularly, the inventors have found out that T cell activation is not only necessary to induce heart disease, as previously shown in Kallikourdis, M, et al. (2017), "T cell costimulation blockade blunts pressure overload-induced heart failure", Nat Commun, 8 14680, but that such activation is also sufficient to induce disease progression. As shown in FIG. 1, the transfer via intravenous injection of T cells taken from cardiopathic mice subjected to Transverse Aortic Constriction (TAC) to induce HF, into healthy recipient mice lead to the development of significant heart dysfunction in the latter, thus indicating the T-cell dependence of the mechanism of HF progression.

Typically, the identification of antigens recognized by T cells is a costly and technically challenging task, as the standard procedure requires the steps of identifying the T Cell Receptor (TCR) sequence of the T cells involved in the disease, cloning and expressing the sequence of each of the two independent TCR chains so that they fold together, and scanning the generated TCRs against peptide libraries. Moreover, as the TCR recognizes only peptides processed for and expressed on Major Histocompatibility (MHC) molecules, which are highly polymorphic and change from person to person, the TCR-peptide screen may produce results that are limited in their validity to small genetically similar populations, thus with limited applicability.

In order to overcome the drawbacks and limitation of the methods of the prior art, the present invention now provides a new method of identifying peptide antigens that drive the T cell responses in adaptive immunity involved in the onset and progression of a non-autoimmune disease, particularly in the chronicity of a non-autoimmune disease.

The method of the invention is based on the surprising finding made by the inventors that the antigen specificity of IgG-switched antibodies may be used as a proxy for the antigen specificity of T cells that were required to enable B cells to produce these antibodies, in the context of a T cell-dependent non-autoimmune disease.

Antibodies against a specific antigen, produced by B cells that have interacted with said antigen, switch their heavy chain class (from IgM or IgD, to IgG or IgA or IgE) only if the B cells interact, i.e. receive "help", with a T cell recognizing the same specific antigen. Both T cells and B cells have variable antigen receptors, each unique in every T or B cell, capable of recognizing any antigen. Upon interacting with a T cell recognizing the same antigen, antibody-producing B cells can switch their antibody heavy chains from IgM or IgD to IgG, or IgA or IgE. Hence, IgG-switched antibodies guarantee that the antigen-specificity of the producing B cell matches that of an activated T cell.

Therefore, a first aspect of the invention is a method for identifying a peptide antigen which is relevant to a human or veterinary non-autoimmune disease involving T cell activation, said method comprising the following steps:

(i) contacting a first biological fluid sample containing IgG immunoglobulins from a first non-human animal affected by the non-autoimmune disease with a microarray comprising a plurality of isolated or synthesized peptide antigens, each peptide having a predetermined location in the microarray and comprising an amino acid sequence of a protein from the non-human animal;

(ii) detecting the binding of one or more of the IgG immunoglobulins present in the first sample with one or more of the peptide antigens in the microarray to provide a first IgG-bound peptide profile;

(iii) comparing the first IgG-bound peptide profile to a second IgG-bound peptide profile generated by contacting a microarray as defined in step (i) with a second biological fluid sample containing IgG immunoglobulins from a second non-human animal, wherein the second non-human animal is not affected by the non-autoimmune disease and wherein the first and second non-human animals belong to the same species and are congenic animals;

(iv) identifying the one or more IgG-bound peptides which are present in the first IgG-binding profile and are not present in the second IgG binding profile;

(v) querying a database of animal protein sequences using the amino acid sequence of each IgG-bound peptide identified in step (iv) as the query in order to select one or more animal proteins comprising a peptide sequence which has an amino acid sequence identity to the amino acid sequence of each of the queried peptides comprised between 67% and 100%, wherein the animal protein sequences are from an animal belonging to a species which is different from the first and second non-human animals of step (iii);

(vi) identifying as peptide antigens relevant to the non-autoimmune disease the peptide sequences which have from 67% to 100% amino acid sequence identity selected in step (v) and which are comprised in an animal protein expressed in a tissue affected by the non-autoimmune disease.

According to the invention, the peptide antigen identified with the method of the invention, hereinafter designated a discovery method, is relevant to a non-autoimmune disease involving T cell activation, which means that the peptide antigen is sufficient to induce said non-autoimmune disease or may be involved in the progression of said non-autoimmune disease in a human being or in an animal.

The discovery method of the invention makes use of a microarray comprising a plurality of isolated or synthesized antigenic peptides comprising an amino acid sequence of a protein from a non-human animal, for example of a murine protein.

By way of example, the amino acid sequences of said plurality of antigenic peptides may be from tissue-specific proteins of a non-human animal, such as e.g. mouse cardiac tissue-specific proteins or mouse nervous tissue-specific proteins, or from the proteome set of proteins of a non-human animal, such as e.g. the mouse proteome.

In one embodiment, the microarray employed in the discovery method of the invention may be a planar microarray, wherein the isolated or synthesized antigenic peptides are immobilized onto a solid support, at discrete individual locations. Alternatively, the microarray may be a bead-based microarray, wherein the isolated or synthesized antigenic peptides are bound to color-coded or size-coded microspheres.

According to the discovery method of the invention, the peptide microarray is assayed with a first and a second biological fluid sample containing IgG immunoglobulins, said first and second biological fluid sample being from a first non-human animal affected by a non-autoimmune disease and from a second non-human animal not affected by said non-autoimmune disease, respectively. Following the microarray assay, differentially IgG-bound antigenic peptides are identified.

A key feature of the discovery method of the invention is that the first and second non-human animals belong to the same species and are congenic, i.e. genetically identical. Such a key feature provides for any difference in the IgG antibody repertoire of these animals, and in the corresponding profile of IgG-bound peptides in the microarray, being ascribed to the non-autoimmune disease which affects the first non-human animal and does not affect the second non-human animal.

In a preferred embodiment, the first and second non-human animals are mice.

In a more preferred embodiment, the first non-human animal is a mouse model of the non-autoimmune disease, preferably a mouse model of a cardiovascular disease, more preferably a Transverse Aortic Constriction (TAC) model.

As known in the art, TAC in the mouse is a commonly used experimental model for pressure overload-induced cardiac hypertrophy and heart failure.

Other non-limiting examples of mouse models of disease are chronic heart failure after myocardial infarction or genetically-induced models of dilated cardiomyopathy, age-related Heart Failure models (aged mice), Myocardial Infarction models, HFpEF mouse models, hypertension models leading to HF (induced by AngII or L-NAME administration).

In the discovery method of the invention, the amino acid sequence of each IgG-bound peptide identified as above described is used as a query sequence and compared with a database of animal protein sequences, said animal being of a different species than the first and second non-human animals.

The discovery method of the invention is further characterized in that an animal protein database is queried with the amino acid sequence of each IgG-bound peptide identified as above described. The results of the database query are selected according as to whether the identified animal protein comprises a peptide sequence which has an amino acid sequence identity to the amino acid sequence of each of the queried peptides comprised between 67% and 100%.

Preferably, the amino acid sequence identity is of at least 67%, at least 70%, at least 75%, at least 80%, at least 85%, at least 90%, at least 95%, at least 96%, at least 97, at least 98%, or at least 99%.

As used herein, the term "percent (%) amino acid sequence identity" with respect to a reference polypeptide sequence refers to the percentage of amino acids in a candidate sequence that are identical to the amino acids in the reference polypeptide sequence, after aligning the sequences and introducing gaps, if necessary, to achieve the maximum percent sequence identity. Alignment for purposes of determining percent amino acid sequence identity can be achieved in various ways that are within the capabilities of one of skill in the art, for example, using publicly available computer software such as BLAST, BLAST-2, or Megalign software. Those skilled in the art can determine appropriate parameters for aligning sequences, including any algorithms needed to achieve maximal alignment over the full length of the sequences being compared. For example, percent sequence identity values may be generated using the sequence comparison computer program BLAST.

As a further step of the discovery method of the invention, peptide antigens relevant to the non-autoimmune disease are identified as having an amino acid sequence comprised in an animal protein expressed in a tissue affected by the non-autoimmune disease.

In one embodiment, the animal is a human being, a dog or a cat.

Any type of biological fluid sample suitable for assaying IgG immunoglobulin content can be used for carrying out the discovery method of the invention, preferably blood samples and derivatives thereof, such as serum and plasma.

In a preferred embodiment, the detection of the binding of one or more of the IgG immunoglobulins present in the first and/or second biological fluid sample with one or more of the antigenic peptides in the microarray is achieved by means of a secondary antibody. Typically, the secondary antibody is directed towards the IgG immunoglobulin that is part of the immunocomplex formed between said IgG and the peptide, and is generated in an animal species that is different from the first and second non-human animals from whom the first and second biological fluid samples were taken.

Preferably, the secondary antibody used in the discovery method of the invention is an anti-IgG antibody, more preferably is an anti-IgG antibody labeled with a detectable label preferably selected from a radioactive isotope, a fluorophore, an enzyme, a chemiluminescent compound, an affinity label such as for example avidin or biotin.

Although the present experimental studies have been carried out using a mouse model of heart failure, it should be understood that the discovery method of the invention is directly applicable to the identification of peptide antigens relevant to other non-autoimmune diseases, particularly chronic non-autoimmune diseases likely to be T cell mediated. By way of example, but without limitation, the non-autoimmune disease may be a cardiac disease, a vascular disease, atherosclerosis, vascular stenosis, a metabolic disease (diabetes not type 1, metabolic syndrome), obesity, a neurodegenerative and neurological disease (Amyotrophic Lateral Sclerosis-ALS, Alzheimer's Disease, Dementia, Age-related Dementia, Mild Cognitive Decline, Parkinson's Disease) or an old-age-related disease.

In a preferred embodiment, heart failure is hemodynamically induced heart failure i.e. caused by hemodynamic stress on the cardiomyocytes, which includes increased workload due to post-myocardial infarction, increased pre-load or afterload due to valvular disease or arterial pressure increase or intrinsic, therefore inherited, defects of the cardiomyocyte.

In a still further embodiment, the discovery method of the invention may be employed as a tool for the management of multimorbidity.

As above described, multimorbidity is a clinical situation wherein a patient suffers simultaneously from more than one of the following groups of ailments: cardiovascular, neurological, oncological and metabolic disease.

According to the invention, peptide antigens may be identified which are relevant to a large range of non-autoimmune diseases involving T cell activation, such as e.g. cardiovascular, neurological, oncological and metabolic diseases, and such antigens may be used to provide a real-time assessment of propensity/early diagnosis of emerging adaptive immune responses targeting different tissues.

Thanks to the method of the invention a first sub-clinical sign of morbidity affecting these tissues may be provided, thereby enabling cross-discipline diagnosis and rapid referral to specialist with a focus on the newly-affected tissue, pre-empting the progression of multimorbidity.

Advantageously, the discovery method of the invention may be repeatedly applied until no more novel peptides are identified, thereby reaching saturation. Indeed, in most immune responses where the target is not rapidly mutating (i.e. not a virus or a tumor) only a small number of immunodominant antigens drive the response. Thus, a few runs of the discovery method of the invention will enable saturation in the identification of novel hits, for example, the identification of the majority of the antigens driving the HF-promoting adaptive response.

Thanks to the unique and advantageous features of the discovery method of the invention as defined above, the present inventors have identified novel peptides which act as drivers of adaptive immune responses to cardiac stress, particularly of the T cell responses that mediate heart failure (HF).

As is further explained in detail below, the inventors have assayed serum samples collected from congenic TAC-operated (hereinafter referred to as TAC) and sham-operated (hereinafter referred to as sham) control mice on a mouse microarray comprising known random oligopeptides. The profiles of IgG-bound peptides generated by microarray analysis were computationally filtered in a differential analysis for IgG-bound peptides present in the TAC-assayed and not in the sham-assayed microarray. The results of this analysis were subjected to a further filtering step so as to select only peptide antigens having high homology to human proteins expressed in the cardiovascular tissue.

To validate the results of the above-described approach, the inventors have conducted a functional study by immunizing healthy mice with the selected peptide antigens in the presence of adjuvant, without applying any cardiovascular stress. As is shown in FIGS. 6A and 6B, mouse immunization surprisingly led to reduced heart function as assessed by measuring the fractional shortening (FS) and the ejection fraction (EF) in the treated animals.

Hence, the studies conducted by the present inventors revealed for the first time that the identified novel peptides are per se sufficient to induce heart failure in an animal and are active mediators of disease progression, thereby representing ideal diagnostic and therapeutic markers. Further supporting the previously described experimental results, the present inventors checked the diagnostic value of the novel peptides in an ELISA immunoassay, by assaying the presence of IgG antibodies recognizing these peptides in human sera from patients affected by heart failure (HF) and healthy controls. The results from the ELISA test, illustrated by the scatter plots in FIG. 8, demonstrate that measuring the titer of IgG antibodies against the novel peptides, produced by T cell-dependent B cells, enables to differentiate HF patients from healthy controls.

In light of the above, a second aspect of the invention is an isolated peptide consisting of an amino acid sequence selected from the group consisting of:

SEQ ID NOs. 1, 2, 3 and 4 of a human 14-3-3 protein; SEQ ID NO. 5 of human small nuclear ribonucleoprotein Sm D1 (SNRPD1); SEQ ID NO. 6 of human ATP synthase subunit O, mitochondrial precursor (ATP5O); SEQ ID NO. 7 of human toll-like receptor 5 precursor (TLR5), and any combination thereof;

or an isolated peptide consisting of an amino acid sequence selected from the group consisting of:

SEQ ID NOs. 1, 2, 3 and 4 of canine 14-3-3 protein; SEQ ID NO. 8 of canine monocarboxylate transporter 3 and 4 proteins (MCT3 and MCT4); SEQ ID NO. 5 of canine SNRPD1; SEQ ID NO. 9 of canine ATP5O; SEQ ID NO. 10 of canine dihydropyrimidinase (DHP) protein, and any combination thereof;

or an isolated peptide consisting of an amino acid sequence selected from the group consisting of:

SEQ ID NOs. 1, 2, 3 and 4 of feline 14-3-3 protein; SEQ ID NO. 8 of feline MCT3 and MCT4 proteins; SEQ ID NO. 11 of feline vomeronasal 1 receptor felCatV1R6 protein; SEQ ID NO. 12 of feline transmembrane emp24 domain-containing protein 6; SEQ ID NO. 5 of feline SNRPD1; SEQ ID NO. 13 of feline ATP5O; SEQ ID NO. 10 of feline DHP protein, and any combination thereof.

According to the invention, the isolated peptide of the invention is cardiac-specific in that it consists of an amino acid sequence of a protein expressed in human, canine or feline cardiac tissue, though not excluding its possible expression also in other tissues.

The term "14-3-3 protein" as used in the present description refers to the different isoforms of human, dog and cat 14-3-3 protein including human isoforms: 14-3-3 protein epsilon, 14-3-3 protein epsilon isoform X1, 14-3-3 protein epsilon isoform X2, 14-3-3 protein beta/alpha, 14-3-3 protein theta, 14-3-3 protein zeta/delta, 14-3-3 protein eta, 14-3-3 protein gamma, 14-3-3 protein sigma; dog isoforms: 14-3-3 protein epsilon isoform X1, 14-3-3 protein epsilon isoform X2, 14-3-3 protein epsilon isoform X3, 14-3-3 protein epsilon isoform X4, 14-3-3 protein theta-like, 14-3-3 protein theta, 14-3-3 protein zeta/delta, 14-3-3 protein beta/ alpha, 14-3-3 protein eta, 14-3-3 protein gamma, 14-3-3 protein sigma; and cat isoforms: 14-3-3 protein epsilon isoform X1, 14-3-3 protein epsilon isoform X2, 14-3-3 protein epsilon isoform X3, 14-3-3 protein theta, 14-3-3 protein zeta/delta, 14-3-3 protein beta/alpha, 14-3-3 protein eta, 14-3-3 protein gamma, 14-3-3 protein sigma.

The term "monocarboxylate transporter 3 (MCT3) or 4 (MCT4) proteins" as used in the present description refers to the different isoforms of human, dog and cat MCT3 and MCT4 proteins, respectively, including feline MCT4 isoform X2 and isoform X21.

The term "transmembrane emp24 domain-containing protein 6" as used in the present description refers to the different isoforms of human, dog and cat transmembrane emp24 domain-containing protein 6, including feline transmembrane emp24 domain-containing protein 6 isoform X1 and isoform X2.

The term "small nuclear ribonucleoprotein Sm D1 (SNRPD1)" as used in the present description refers to the different isoforms of human, dog and cat SNRPD1, including feline SNRPD1 isoform X1 and isoform X2.

The term "dihydropyrimidinase protein" as used in the present description refers to the different isoforms of human, dog and cat dihydropyrimidinase protein, including feline dihydropyrimidinase isoform X1 and isoform X2.

According to the invention, it is envisaged that any possible combination of the isolated peptides as above defined is encompassed within the present invention.

A preferred embodiment according to the invention is at least one peptide of human 14-3-3 protein selected from the group consisting of SEQ ID NOs. 1, 2, 3 and 4, in combination with a peptide consisting of SEQ ID NO. 5 of human SNRPD1 protein and a peptide consisting of SEQ ID NO. 6 of human ATP50 protein.

Another preferred embodiment according to the invention is at least two peptides of human 14-3-3 protein selected from the group consisting of SEQ ID NOs. 1, 2, 3 and 4, in combination with a peptide consisting of SEQ ID NO. 5 of human SNRPD1 protein and a peptide consisting of SEQ ID NO. 6 of human ATP50 protein. The at least two peptides of human 14-3-3 protein are, for example, (a) a peptide of SEQ ID NO. 1 and a peptide of SEQ ID NO. 2, (b) a peptide of SEQ ID NO. 1 and a peptide of SEQ ID NO. 3, (c) a peptide of SEQ ID NO. 1 and a peptide of SEQ ID NO. 4, (d) a peptide of SEQ ID NO. 2 and a peptide of SEQ ID NO. 3, (e) a peptide of SEQ ID NO. 2 and a peptide of SEQ ID NO. 4, or (f) a peptide of SEQ ID NO. 3 and a peptide of SEQ ID NO. 4.

Another preferred embodiment according to the invention is at least three peptides of human 14-3-3 protein selected from the group consisting of SEQ ID NOs. 1, 2, 3 and 4, in combination with a peptide consisting of SEQ ID NO. 5 of human SNRPD1 protein and a peptide consisting of SEQ ID NO. 6 of human ATP50 protein. The at least three peptides of human 14-3-3 protein are, for example, (g) a peptide of SEQ ID NO. 1, a peptide of SEQ ID NO. 2 and a peptide of SEQ ID NO. 3, (h) a peptide of SEQ ID NO. 1, a peptide of SEQ ID NO. 2 and a peptide of SEQ ID NO. 4, (i) a peptide of SEQ ID NO. 1, a peptide of SEQ ID NO. 3 and a peptide of SEQ ID NO. 4, or (j) a peptide of SEQ ID NO. 2, a peptide of SEQ ID NO. 3 and a peptide of SEQ ID NO. 4.

A still another preferred embodiment according to the invention is at least four peptides consisting of SEQ ID NOs. 1, 2, 3 and 4 of human 14-3-3 protein, respectively, in combination with a peptide consisting of SEQ ID NO. 5 of human SNRPD1 protein and a peptide consisting of SEQ ID NO. 6 of human ATP50 protein.

Optionally, in the above-illustrated embodiments according to the invention, the combination of peptides may further comprise a peptide consisting of SEQ ID NO. 7 of human TLR5 protein.

A third aspect of the present invention is an in vitro method for the diagnosis and/or for predicting the risk for developing heart failure (HF) in a human subject, said method comprising the steps of: (i) contacting a biological fluid sample containing IgG immunoglobulins derived from a human subject affected by HF or suspected of being at risk for developing HF, with one or more isolated antigenic peptides from one or more human proteins selected from the group consisting of 14-3-3 protein epsilon (SEQ ID NO. 18), 14-3-3 protein epsilon isoform X1 (SEQ ID NO. 19), 14-3-3 protein epsilon isoform X2 (SEQ ID NO. 20), 14-3-3 protein beta/alpha (SEQ ID NO. 21), 14-3-3 protein theta (SEQ ID NO. 22), 14-3-3 protein zeta/delta (SEQ ID NO. 23), 14-3-3 protein eta (SEQ ID NO. 24), 14-3-3 protein gamma (SEQ ID NO. 25), 14-3-3 protein sigma (SEQ ID NO. 26), small nuclear ribonucleoprotein Sm D1 isoform 1 (SEQ ID NO. 27), ATP synthase subunit O, mitochondrial precursor (SEQ ID NO. 28), toll-like receptor 5 precursor (SEQ ID NO. 29), and any combination thereof, wherein the one or more isolated antigenic peptides are from 6 to 50 amino acids in length; (ii) detecting the formation of one or more immunocomplexes between the IgG immunoglobulins in the biological fluid sample and the one or more isolated antigenic peptides, the formation of the one or more immunocomplexes being indicative of the human subject being affected by HF or being at risk for developing HF.

In a preferred embodiment, the one or more isolated antigenic peptides consist of an amino acid sequence selected from the group consisting of SEQ ID NOs. 1, 2, 3 and 4 of a human 14-3-3 protein; SEQ ID NO. 5 of human small nuclear ribonucleoprotein Sm D1 (SNRPD1); SEQ ID NO. 6 of human ATP synthase subunit O, mitochondrial precursor (ATP5O); SEQ ID NO. 7 of human toll-like receptor 5 precursor (TLR5), and any combination thereof.

In a more preferred embodiment, the method of the invention employs at least one peptide of human 14-3-3 protein selected from the group consisting of SEQ ID NOs. 1, 2, 3 and 4, in combination with a peptide consisting of SEQ ID NO. 5 of human SNRPD1 protein and a peptide consisting of SEQ ID NO. 6 of human ATP50 protein.

In another preferred embodiment, the method of the invention employs at least two peptides of human 14-3-3 protein selected from the group consisting of SEQ ID NOs. 1, 2, 3 and 4, in combination with a peptide consisting of SEQ ID NO. 5 of human SNRPD1 protein and a peptide consisting of SEQ ID NO. 6 of human ATP50 protein. The at least two peptides of human 14-3-3 protein are, for example, (a) a peptide of SEQ ID NO. 1 and a peptide of SEQ ID NO. 2, (b) a peptide of SEQ ID NO. 1 and a peptide of SEQ ID NO. 3, (c) a peptide of SEQ ID NO. 1 and a peptide of SEQ ID NO. 4, (d) a peptide of SEQ ID NO. 2 and a peptide of SEQ ID NO. 3, (e) a peptide of SEQ ID NO. 2 and a peptide of SEQ ID NO. 4, or (f) a peptide of SEQ ID NO. 3 and a peptide of SEQ ID NO. 4.

In another preferred embodiment, the method of the invention employs at least three peptides of human 14-3-3 protein selected from the group consisting of SEQ ID NOs. 1, 2, 3 and 4, in combination with a peptide consisting of SEQ ID NO. 5 of human SNRPD1 protein and a peptide consisting of SEQ ID NO. 6 of human ATP50 protein. The at least three peptides of human 14-3-3 protein are, for example, (g) a peptide of SEQ ID NO. 1, a peptide of SEQ ID NO. 2 and a peptide of SEQ ID NO. 3, (h) a peptide of SEQ ID NO. 1, a peptide of SEQ ID NO. 2 and a peptide of SEQ ID NO. 4, (i) a peptide of SEQ ID NO. 1, a peptide of SEQ ID NO. 3 and a peptide of SEQ ID NO. 4, or (j) a peptide of SEQ ID NO. 2, a peptide of SEQ ID NO. 3 and a peptide of SEQ ID NO. 4.

In a still another preferred embodiment, the method of the invention employs at least four peptides consisting of SEQ ID NOs. 1, 2, 3 and 4 of human 14-3-3 protein, respectively, in combination with a peptide consisting of SEQ ID NO. 5 of human SNRPD1 protein and a peptide consisting of SEQ ID NO. 6 of human ATP5O protein.

Optionally, in the above-illustrated embodiments according to the method of the invention, the combination of peptides may further comprise a peptide consisting of SEQ ID NO. 7 of human TLR5 protein.

In cases where the immune response against the diseased cardiovascular tissue exists without having yet led to clinically-observable symptoms, the detection of IgG antibodies in the in vitro method of the invention via the identified novel antigens provides a valuable indication of the propensity of the subject under examination to develop clinically-identifiable disease symptoms. If the heart disease has already developed clinically-identifiable symptoms, the detection in the method of the invention of IgG antibodies against the identified novel antigens enables the diagnosis of the specific heart disease.

The present invention is not limited to human diagnosis and finds veterinary applications as well.

Accordingly, in another aspect, the method of the invention is an in vitro method for the diagnosis and/or prognosis of heart failure (HF) and/or for predicting the risk for developing HF in a dog, wherein the isolated antigenic peptides are from one or more canine proteins selected from the group consisting of 14-3-3 protein epsilon isoform X1 (SEQ ID NO. 30), 14-3-3 protein epsilon isoform X2 (SEQ ID NO. 31), 14-3-3 protein epsilon isoform X3 (SEQ ID NO. 32), 14-3-3 protein epsilon isoform X4 (SEQ ID NO. 33), 14-3-3 protein theta-like (SEQ ID NO. 34), 14-3-3 protein theta (SEQ ID NO. 35), 14-3-3 protein zeta/delta (SEQ ID NO. 36), 14-3-3 protein beta/alpha (SEQ ID NO. 37), 14-3-3 protein eta (SEQ ID NO. 38), 14-3-3 protein gamma (SEQ ID NO. 39), 14-3-3 protein sigma (SEQ ID NO. 40), monocarboxylate transporter 3 and 4 proteins (SEQ ID NOs. 41 and 42), small nuclear ribonucleoprotein Sm D1 (SEQ ID NO. 43), ATP synthase subunit O, mitochondrial precursor (SEQ ID NO. 44), dihydropyrimidinase protein (SEQ ID NO. 45), and any combination thereof, wherein the one or more isolated antigenic peptides are from 6 to 50 amino acids in length.

In a preferred embodiment, the one or more isolated antigenic peptides consist of an amino acid sequence selected from the group consisting of SEQ ID NOs. 1, 2, 3 and 4 of canine 14-3-3 protein; SEQ ID NO. 8 of canine monocarboxylate transporter 3 and 4 proteins (MCT3 and MCT4); SEQ ID NO. 5 of canine SNRPD1; SEQ ID NO. 9 of canine ATP5O; SEQ ID NO. 10 of canine dihydropyrimidinase (DHP) protein, and any combination thereof.

In a preferred embodiment, this aspect of the invention may be relevant to Heart Failure from Dilated Cardiomyopathy arising due to genetic mutations in dog strains including but not limited to Doberman Pinscher, Great Dane, Boxer, Cocker Spaniel.

In a still another aspect, the method of the invention is an in vitro method for the diagnosis and/or prognosis of heart failure (HF) and/or for predicting the risk for developing HF in a cat, wherein the isolated antigenic peptides are from one or more feline proteins selected from the group consisting of 14-3-3 protein epsilon isoform X1 (SEQ ID NO. 46), 14-3-3 protein epsilon isoform X2 (SEQ ID NO. 47), 14-3-3 protein epsilon isoform X3 (SEQ ID NO. 48), 14-3-3 protein theta (SEQ ID NO. 49), 14-3-3 protein zeta/delta (SEQ ID NO. 50), 14-3-3 protein beta/alpha (SEQ ID NO. 51), 14-3-3 protein eta (SEQ ID NO. 52), 14-3-3 protein gamma (SEQ ID NO. 53), 14-3-3 protein sigma (SEQ ID NO. 54), monocarboxylate transporter 3 protein (SEQ ID NO. 55), monocarboxylate transporter 4 proteins isoform X2 (SEQ ID NO. 56) and isoform X21 (SEQ ID NO. 57), vomeronasal 1 receptor felCatV1R6 protein (SEQ ID NO. 58), transmembrane emp24 domain-containing protein 6, isoform X1 (SEQ ID NO. 59), transmembrane emp24 domain-containing protein 6, isoform X2 (SEQ ID NO. 60), small nuclear ribonucleoprotein Sm D1, isoform X1 (SEQ ID NO. 61), small nuclear ribonucleoprotein Sm D1, isoform X2 (SEQ ID NO. 62), ATP synthase subunit O, mitochondrial precursor (SEQ ID NO. 63), dihydropyrimidinase protein, isoform X1 (SEQ ID NO. 64), dihydropyrimidinase protein, isoform X2 (SEQ ID NO. 65) and any combination thereof, wherein the one or more isolated antigenic peptides are from 6 to 50 amino acids in length.

In a preferred embodiment, the one or more isolated antigenic peptides consist of an amino acid sequence selected from the group consisting of SEQ ID NOs. 1, 2, 3 and 4 of feline 14-3-3 protein; SEQ ID NO. 8 of feline MCT3 and MCT4 proteins; SEQ ID NO. 11 of feline vomeronasal 1 receptor felCatV1R6 protein; SEQ ID NO. 12 of feline transmembrane emp24 domain-containing protein 6; SEQ ID NO. 5 of feline SNRPD1; SEQ ID NO. 13 of feline ATP5O; SEQ ID NO. 10 of feline DHP protein, and any combination thereof.

In a preferred embodiment, this aspect of the invention may be relevant to Heart Failure from Dilated Cardiomyopathy arising due to genetic mutations in cat strains including but not limited to Burmese, Abyssinian, and Siamese.

In a preferred embodiment, this aspect of the invention may be relevant to Heart Failure from Hypertrophic Cardiomyopathy arising due to genetic mutations in cat strains including but not limited to Maine Coon, Ragdoll, British Shorthair, Sphynx, Chartreux and Persian.

According to the in vitro methods of the invention, the one or more isolated antigenic peptides are from 6 to 50 amino acids in length, preferably from 7, 8, 9, 10, 15, 20, 25, 30, 35, 40, 45 to 50 amino acids in length.

Among the most largely used methods for identifying and quantifying an antibody specific against an antigen in a biological sample, the immunological procedures are the method of choice. Hence, in a preferred embodiment, the in vitro method of the invention is an immunoassay.

In a more preferred embodiment, the in vitro method of the invention is an Enzyme-Linked Immunosorbent Assay, known as ELISA. In this assay an immunocomplex is formed between the one or more antigenic peptides immobilized on a solid phase, for example the surface of a microtitre plate or a bead, and the IgG antibodies present in a biological fluid sample from the patient, such as for example a serum or a plasma sample.

The formation of IgG antibody/antigenic peptide complexes may then be detected using any suitable method. In one preferred embodiment, a labelled secondary anti-IgG immunoglobulin antibody is used. Suitable labels for use in the present invention include for example fluorescent compounds, chemiluminescent compounds, radioactive compounds, enzymes and enzyme substrates, and molecules suitable for colorimetric detection.

Obviously, the use of any type of immunoassay format, the selection of which falls within the skills of the ordinary person of skill in the art, is within the scope of the present invention. Preferably, the biological fluid sample is selected from the group consisting of whole blood, serum, plasma, synovial fluid, follicular fluid and intraocular fluid. The biological fluid sample may optionally include further components, such as for example: diluents, preservatives, stabilizing agents and/or buffers. If needed, dilutions of the biological fluid sample are prepared using any suitable diluent buffer known in the art.

In one embodiment of the in vitro method of the invention, a quantitative assessment may be performed of the levels of the cardiovascular antigen-specific IgG antibodies in the patient against standards of "true" healthy controls as well as healthy controls with matching age and gender. According to the invention, the readout of such assessment provides an indication of the propensity/risk in a subject for developing cardiovascular disease with clinically-identifiable symptoms. In cases where an aged "healthy" individual has a non-zero cardiac-specific antibody titer, the non-zero signal, as quantified in the method of the invention against "true negatives" represents nonetheless a proxy of propensity to cardiotoxic immune responses and thus cardiovascular disease.

In one embodiment, the in vitro method of the invention is suitable for the real-time assessment of cardiotoxicity in tumor immunotherapy.

Checkpoint blockade immunotherapy (CBI) (e.g. via antiPD1, antiCTLA4) is a novel, highly successful means of therapy of advanced hematologic and solid tumors, that is being increasingly applied in the clinic (Barbee, M S, et al. (2015), "Current status and future directions of the immune checkpoint inhibitors ipilimumab, pembrolizumab, and nivolumab in oncology", Ann Pharmacother, 49 (8), 907-37). Cardiotoxic responses are mediated by the T cell-driven mechanism. Thus, the in vitro method according to the invention may advantageously enable the prediction and/or detection and quantification of T-cell responses that target cardiovascular tissues when the patient has still sub-clinical cardiac symptoms. Whilst the cardiotoxic responses affects a small, though increasing, percentage of patients, they become rapidly lethal once they appear, hence their early detection is life-saving.

In another embodiment, the in vitro method of the invention provides for the diagnosis of potential risks associated with the introduction of novel biological drugs or immunotherapeutic drugs or vaccines.

As an increasing number of immune-modifying drugs, monoclonal antibodies, and vaccines are being introduced in the clinic for trial and eventual utilization, there is an increasing risk for the induction of off-target inflammation. Advantageously, the in vitro method of the invention enables a real-time assessment of such responses targeting the heart during the clinical testing phase of novel reagents in development, as well as during approved clinical practice for those reagents with an increased risk profile and/or for patients whose characteristics present increased risk for off-target toxicity.

In a further embodiment, the in vitro method of the invention is suitable to be applied for heart transplantation monitoring, as the detected cardiac antigen-specific IgG antibodies may represent a real-time proxy of rejection of the transplanted heart.

The means suitable for performing the in vitro method of the invention are assembled into a kit in order to facilitate the use thereof.

Therefore, a further aspect of the invention is a kit for the diagnosis and/or for predicting the risk for developing heart failure (HF) in a human being, in a dog or in a cat, as defined in appended claims 9, 10 and 11.

In a preferred embodiment, the one or more isolated antigenic peptides in the kit of the invention consist of an amino acid sequence selected from the group consisting of SEQ ID NOs. 1, 2, 3 and 4 of a human 14-3-3 protein; SEQ ID NO. 5 of human small nuclear ribonucleoprotein Sm D1 (SNRPD1); SEQ ID NO. 6 of human ATP synthase subunit O, mitochondrial precursor (ATP5O); SEQ ID NO. 7 of human toll-like receptor 5 precursor (TLR5), and any combination thereof.

In a more preferred embodiment, the one or more isolated antigenic peptides in the kit of the invention consist of at least one peptide of human 14-3-3 protein selected from the group consisting of SEQ ID NOs. 1, 2, 3 and 4, in combination with a peptide consisting of SEQ ID NO. 5 of human SNRPD1 protein and a peptide consisting of SEQ ID NO. 6 of human ATP5O protein.

In another preferred embodiment, the one or more isolated antigenic peptides in the kit of the invention consist of at least two peptides of human 14-3-3 protein selected from the group consisting of SEQ ID NOs. 1, 2, 3 and 4, in combination with a peptide consisting of SEQ ID NO. 5 of human SNRPD1 protein and a peptide consisting of SEQ ID NO. 6 of human ATP5O protein. The at least two peptides of human 14-3-3 protein are, for example, (a) a peptide of SEQ ID NO. 1 and a peptide of SEQ ID NO. 2, (b) a peptide of SEQ ID NO. 1 and a peptide of SEQ ID NO. 3, (c) a peptide of SEQ ID NO. 1 and a peptide of SEQ ID NO. 4, (d) a peptide of SEQ ID NO. 2 and a peptide of SEQ ID NO. 3, (e) a peptide of SEQ ID NO. 2 and a peptide of SEQ ID NO. 4, or (f) a peptide of SEQ ID NO. 3 and a peptide of SEQ ID NO. 4.

In another preferred embodiment, the one or more isolated antigenic peptides in the kit of the invention consist of at least three peptides of human 14-3-3 protein selected from the group consisting of SEQ ID NOs. 1, 2, 3 and 4, in combination with a peptide consisting of SEQ ID NO. 5 of human SNRPD1 protein and a peptide consisting of SEQ ID NO. 6 of human ATP5O protein. The at least three peptides of human 14-3-3 protein are, for example, (g) a peptide of SEQ ID NO. 1, a peptide of SEQ ID NO. 2 and a peptide of SEQ ID NO. 3, (h) a peptide of SEQ ID NO. 1, a peptide of SEQ ID NO. 2 and a peptide of SEQ ID NO. 4, (i) a peptide of SEQ ID NO. 1, a peptide of SEQ ID NO. 3 and a peptide of SEQ ID NO. 4, or (j) a peptide of SEQ ID NO. 2, a peptide of SEQ ID NO. 3 and a peptide of SEQ ID NO. 4.

In a still another preferred embodiment, the one or more isolated antigenic peptides in the kit of the invention consist of at least four peptides consisting of SEQ ID NOs. 1, 2, 3 and 4 of human 14-3-3 protein, respectively, in combination with a peptide consisting of SEQ ID NO. 5 of human SNRPD1 protein and a peptide consisting of SEQ ID NO. 6 of human ATP5O protein.

Optionally, in the above-illustrated embodiments according to the invention, the combination of peptides in the kit of the invention may further comprise a peptide consisting of SEQ ID NO. 7 of human TLR5 protein.

In another preferred embodiment, the one or more isolated antigenic peptides in the kit of the invention consist of an amino acid sequence selected from the group consisting of SEQ ID NOs. 1, 2, 3 and 4 of canine 14-3-3 protein; SEQ ID NO. 8 of canine monocarboxylate transporter 3 and 4 proteins (MCT3 and MCT4); SEQ ID NO. 5 of canine SNRPD1; SEQ ID NO. 9 of canine ATP5O; SEQ ID NO. 10 of canine dihydropyrimidinase (DHP) protein, and any combination thereof.

In a still another preferred embodiment, the one or more isolated antigenic peptides in the kit of the invention consist of an amino acid sequence selected from the group consisting of SEQ ID NOs. 1, 2, 3 and 4 of feline 14-3-3 protein; SEQ ID NO. 8 of feline MCT3 and MCT4 proteins; SEQ ID NO. 11 of feline vomeronasal 1 receptor felCatV1R6 protein; SEQ ID NO. 12 of feline transmembrane emp24 domain-containing protein 6; SEQ ID NO. 5 of feline SNRPD1; SEQ ID NO. 13 of feline ATP5O; SEQ ID NO. 10 of feline DHP protein, and any combination thereof.

In the kit of the invention, the one or more antigenic peptides are immobilized on a solid support. Non-limiting examples of suitable solid supports are the wells of a microtitre plate, the surface of a microparticle such as a latex, polystyrene, silica, chelating sepharose or magnetic beads, membranes, strips or chips.

Further, the kits of the invention contain detection means as described above in connection with the in vitro diagnostic methods.

Further experimental studies carried out by the present inventors, which are illustrated in detail in the experimental section that follows, revealed that healthy mice fed with the peptide antigens of the invention, when subjected to Transverse Aortic Constriction (TAC), experienced less severe cardiac disease in comparison with control animals treated with phosphate-buffered saline only. Surprisingly, such findings show that the peptide antigens of the invention are capable of inducing oral tolerance when administered to an animal, which leads to a preventive protection from the severity of heart failure.

Hence, the isolated peptides of the invention, alone or in combination with each other, are particularly suitable for use in orally administered treatment and/or prevention of heart disease.

Accordingly, a further aspect of the invention is the isolated peptide as above defined for use in the therapeutic treatment of heart failure and/or in the prevention of heart failure in a subject in need thereof, said treatment comprising oral administration of the peptide to the subject, thereby inducing oral tolerance to said peptide.

In the context of the present description, the term "oral tolerance" is intended to mean an active process by which the immune system does not respond with an inflammatory reaction to an orally administered antigen. More particularly, the human body tolerates antigens in the gastro-intestinal tract, most likely as a necessary requirement for maintaining gut flora and digesting food.

The oral tolerance process is considered to occur via the induction of induced immunosuppressive Treg (iTreg) cells that may respond to these antigens (Larché, M (2014), "Mechanisms of peptide immunotherapy in allergic airways disease", Ann Am Thorac Soc, 11 Suppl 5 S292-6; Chen, X, et al. (2017), "Oral administration of visceral adipose tissue antigens ameliorates metabolic disorders in mice and elevates visceral adipose tissue-resident CD4(+)CD25(+) Foxp3(+) regulatory T cells", Vaccine).

Without wishing to be bound by any theory, the inventors believe that oral tolerance induction to the peptide antigens of the invention driving the adaptive response that mediate heart failure disease may lead to the generation of antigen-specific immunosuppressive Treg and iTreg cells. These cells act by suppressing any adaptive immune response mediated by pro-inflammatory T cells and B cells leading to heart failure disease, at the time when the deleterious response is initiated.

The method of the invention can prevent the onset of disease or reduce its severity. In the preventative context, the method can delay or prevent the onset of one or more symptoms of heart failure. In the treatment context, the method can delay or prevent the progression of one or more symptoms of heart failure.

The subject in need of the treatment with the peptide of the invention can be a human patient or a non-human patient. In certain embodiments, the non-human patient can be a non-human mammal, for example a dog or a cat. Several strains of domestic dogs and cats suffer from congenital cardiac defects leading to premature onset cardiac dysfunction.

A still further aspect of the invention is a pharmaceutical composition comprising at least one isolated peptide antigen of the invention, or any combination thereof as above defined in connection with preferred embodiments of the invention, as well as a pharmaceutically acceptable carrier, vehicle or diluent. The selection of the carrier, vehicle or diluent as well as of any other excipient required for the preparation of the desired pharmaceutical dosage form falls within the ability of the person skilled in the art.

The above defined pharmaceutical composition is preferably a tolerizing vaccine suitable to be administered via the oral route. As known in the art, a tolerizing vaccine is capable of inducing in a subject an antigen-specific immune tolerance.

Preferably, the tolerizing vaccine does not comprise any adjuvant, i.e. any substance capable to specifically trigger antigenicity and inflammation.

Oral formulations generally include an inert diluent or an edible carrier. They can be enclosed in gelatin capsules or compressed into tablets. For the purpose of oral therapeutic administration, the active compound can be incorporated with excipients and used in the form of tablets, troches, or capsules.

A still further aspect of the invention is a food, feed or drink product comprising at least one isolated peptide as above defined or any combination thereof as above defined in connection with preferred embodiments of the invention. The food, feed or drink product of the invention may be classified as medical food, food supplement or other classification, and can be any food or drink whose preparation does not alter the integrity of the peptide composition.

The following experimental section is provided purely by way of illustration and is not intended to limit the scope of the invention as defined in the appended claims.

EXAMPLE 1: TRANSFER OF T CELLS ARE
SUFFICIENT TO TRANSFER HEART FAILURE
(HF) FROM CARDIOPATHIC TO HEALTHY
MICE

In order to assess whether T cells are not only necessary but also sufficient to induce heart failure (HF), the present inventors followed the experimental approach depicted in FIG. 1A. Such approach involved transferring T cells from mice that had undergone transverse aortic constriction (TAC)-operation to induce HF (or sham-operation controls) into healthy recipient mice, and examining whether this transfer was sufficient to transfer the disease. Briefly, T cells isolated from heart-draining lymph nodes (LN) of C57BL6/J 8 week-old male mice 4 weeks after TAC- or sham-surgery were transferred into healthy mouse recipients. Recipient C57BL6/J 8 week-old male mice received 1*10⁶ cells via intravenous injection.

Cells isolated from heart draining lymph nodes were stained via FACS-analysis in order to examine the population of T cells isolated from heart-draining lymph nodes and injected into healthy recipients. As shown in FIG. 1B, T cells isolated from lymph nodes included cytotoxic CD8+, CD4+ conventional naïve T cells and CD4+ conventional effector T cells, and regulatory T cells Cardiac function of the recipient mice was assessed by echocardiography performed at baseline (before receiving T cells), and 9 and 12 weeks after cell transfer. Fractional shortening (% FS), measured via echocardiography, is an indicator of the left ventricle functionality and it represents the percentage of shortening of the left ventricular diameter between end-diastole and end-systole. Mice that received cells from TAC-operated mice showed a significant decrease of heart functionality measured as % FS, compared to mice receiving T cells from control (sham-operated) mice, signifying a reduction in heart functionality (FIG. 1C). Data were plotted as mean±SEM; solid line represents mice that received cells from TAC-operated mice, dotted line represents mice that received cells from sham-operated mice, (n=6-7) Two-way ANOVA, Bonferroni post-test. * p<0.05.

EXAMPLE 2: ANTIGEN DISCOVERY STRATEGY

Serum samples were collected from 5 sham-operated mice or 5 TAC-operated mice 4 weeks after sham or TAC surgery. The sera were pooled into two samples, respectively (1 TAC and 1 sham). The pooled serum samples were assayed on a commercial mouse autoantigen and random antigen-discovery array (FIG. 2). The bound antibodies were then detected by anti-IgG reagents. The IgG antibody signal was quantified for each hit and the sequence of each recognized peptide (i.e. the sequence of the random oligopeptide spotted on the array) was reported for further analysis, along with the corresponding signal strength. By detecting only IgG antibodies, the inventors narrowed the analysis to the IgG-switched antibodies, which had received T cell help. Importantly, the mice used in the experiment were all congenic, i.e. genetically identical.

EXAMPLE 3: PIPELINE FOR ANTIGEN DISCOVERY. BIOINFORMATIC ANALYSIS STRATEGY FOR THE DIFFERENTIAL ANALYSIS OF THE ARRAY READOUT

With the aim of identifying peptide antigens driving T cells involved in HF pathology, the present inventors set up the discovery strategy as illustrated in FIG. 3.

To perform a differential analysis of the array readout, the inventors ordered each random oligopeptide on the basis of differential ability to produce a hit (TAC IgG binding signal—positive ("up") signals) when tested with TAC pooled serum and no hit when tested with sham pooled serum (sham IgG binding signal—negative "down" signals).

In detail, epitopes recognized by antibodies were selected with a user-defined threshold of x>10 (x=the average and corrected fluorescence intensity changes between Sham mouse serum and TAC mouse serum). The identified oligopeptides (i.e. epitopes) were used to predict potential antigenic proteins using the PSI-BLAST (Position-Specific Iterative Basic Local Alignment Search Tool) from the National Center for Biotechnology Information, which is a protein sequence similarity search program, and the RefSeq non-redundant proteins database (organism *Mus musculus* (taxid: 10090)). PSI-BLAST parameters were set as default. Candidate proteins corresponding to each identified epitope were selected in according to an E-value<0.01.

In order to guarantee that identified proteins were relevant for human disease, the hits were filtered so as to select only those proteins for high homology to human proteins. The list of proteins or protein domains with "up" and no "down" hits was tested for sequence identity (at protein level) to human. The homology with human was evaluated performing PSI-BLAST against the RefSeq non-redundant protein database (organism Human (taxid: 9606)). Proteins with a percentage of alignment higher than 67% were selected. Then, cardiac enrichment of each protein was evaluated using Human Protein Atlas database (https://www.proteinatlas.org/).

Peptides identified as end-results of the above-described process are listed in the Table of FIG. 4. The table contains the following information: name of the mouse gene encoding for the whole protein, amino acid FASTA sequence of the entire protein of origin (sequence not fully visible in the graph), start and end amino acid number of the identified peptides within each protein of origin, amino acid sequence of the identified peptide, peptide length, number of source peptides spotted on the array generating each peptide hit, percentage of homology of the peptide with the homologous human protein.

The three peptides composing Group 3 are derived from mouse beta-1 adrenergic receptor protein (SEQ ID NO. 66), and consist of the amino acid sequences designated as SEQ ID NO. 15 (SAPLSQQWTAGMGLLLALIVLL), SEQ ID NO. 16 (KALKTLGIIMGVFTLCWL), and SEQ ID NO. 17 (HRDLVPDRLFVFFNWL), respectively. The beta-1 adrenergic receptor is known to be an autoantigen driving responses in autoimmune myocarditis (Caforio, A L, et al. (2002), "Circulating cardiac autoantibodies in dilated cardiomyopathy and myocarditis: pathogenetic and clinical significance", Eur J Heart Fail, 4 411-17; Basavalingappa, R H, et al. (2017), "β1-Adrenergic Receptor Contains Multiple IAk and IEk Binding Epitopes That Induce T Cell Responses with Varying Degrees of Autoimmune Myocarditis in A/J Mice", Front Immunol, 8 1567). As it is known that peptides from this protein can lead to autoimmune response targeting the heart, group 3 functioned as an internal positive control in the discovery method of the invention, validating the functionality of the process.

As shown in FIG. 4, Group 4 includes a peptide consisting of amino acid sequence SEQ ID NO. 1, which derives from mouse 14-3-3 protein (SEQ ID NO. 70), a peptide consisting of amino acid sequence SEQ ID NO. 5, which derives from mouse Snrpd1 protein (SEQ ID NO. 79), and a peptide consisting of amino acid sequence SEQ ID NO. 14, which derives from mouse Atp50 protein (SEQ ID NO. 80).

EXAMPLE 4: IMMUNIZATION PROTOCOL FOR ASSESSING THE CARDIO-SPECIFIC IMMUNOGENICITY OF THE PEPTIDES

In order to validate the functional relevance of identified antigens recognized by T cells driving HF, the inventors conducted the experiments as described below and schematically represented in FIG. 5.

Briefly, C57BL6/J 8-week-old male mice were screened, via echocardiography, at baseline for heart functionality and randomly divided into three experimental groups. Mice belonging to the negative control group (CTR−, only CFA) were injected subcutaneously (immunized) with 100 µl Complete Freud's Adjuvant (CFA) at day 0 and boosted with 100 μl of Incomplete Freud's Adjuvant (IFA) on day 21, without any antigen. Mice belonging to group 3 (CTR+) were injected subcutaneously (immunized) with 100 μg of each of the three peptides derived from beta-adrenergic receptor (SEQ ID NOs. 15-17) emulsified in Complete Freud's Adjuvant (CFA) at day 0 and boosted with 100 μg of the three peptides emulsified in Incomplete Freud's Adjuvant (IFA) on day 21. Mice belonging to group 4 (Group 4) were injected subcutaneously (immunized) with 100 μg of each of the three peptides of SEQ ID NOs. 1, 5 and 14, derived from murine 14-3-3, Snrpd1 and, Atp5o proteins, emulsified in Complete Freud's Adjuvant (CFA) at day 0 and boosted with 100 μg of each of the three peptides emulsfied in Incomplete Freud's Adjuvant (IFA) on day 21. On day 0 and day 2, all the mice were intraperitoneally injected with 200 ng of Pertussis Toxin (PTX), as per standard immunization protocols. Heart functionality of all mice was analyzed via echocardiography at 2, 5 and 9 weeks after the first subcutaneous injection.

The immunization experiments of healthy mice with peptides derived from beta-adrenergic receptor and from 14-3-3, Snrpd1, and Atp5o lead to cardiac dysfunction. As shown in the bar graphs of FIGS. 6A and 6B, mice immunized with peptides derived from beta-adrenergic receptor (CTR+) and from 14-3-3, Snrpd1, and Atp5o proteins (Group 4) displayed a significant reduction of cardiac functionality, measured via echocardiography analysis at 2, 5 and 9 weeks after the first subcutaneous injection. Left ventricle functionality was measured as % FS (FIG. 6A) and Ejection Fraction (% EF) (FIG. 6B), which measure the volumetric capacity of the left ventricle to pump blood. Data were plotted as mean±SEM, (n=4-6). Two-way ANOVA and Tukey's multiple comparison test. * $p<0.05$, ** $p<0.01$.

EXAMPLE 5: IMMUNIZATION OF HEALTHY MICE WITH SINGLE PEPTIDES DERIVED FROM 14-3-3, SNRPD1, AND ATP5O INDUCES CARDIAC DYSFUNCTION

C57BL6/J 8-week-old male mice were screened at baseline for heart functionality, via echocardiography, and randomly divided into 5 experimental groups. Mice belonging to control group (CTR–, only CFA) were injected subcutaneously (immunized, but without antigen: negative control) with 100 μl Complete Freud's Adjuvant (CFA) at day 0 and boosted with 100 μl of Incomplete Freud's Adjuvant (IFA) on day 21. Mice belonging to group 3 (CTR+) were injected subcutaneously (immunized, known antigen: positive control) with 100 μg of each of the three peptides (SEQ ID NOs. 15-17) derived from beta-adrenergic receptor and listed in the Table of FIG. 4, emulsified in Complete Freud's Adjuvant (CFA) at day 0 and boosted with 100 μg of the three peptides emulsified in Incomplete Freud's Adjuvant (IFA) on day 21. Mice belonging to group 4_A (Peptide 4_A) were injected subcutaneously (immunized) with 100 μg of the peptide of SEQ ID NO. 1, derived from 14-3-3 protein, emulsified in Complete Freud's Adjuvant (CFA) at day 0 and boosted with 100 μg of each of the three peptides emulsified in Incomplete Freud's Adjuvant (IFA) on day 21. Mice belonging to group 4_B (Peptide 4_B) were injected subcutaneously (immunized) with 100 μg of the peptide of SEQ ID NO. 5, derived from Snrpd1 protein, emulsified in Complete Freud's Adjuvant (CFA) at day 0 and boosted with 100 μg of each of the three peptides emulsified in Incomplete Freud's Adjuvant (IFA) on day 21. Mice belonging to group 4_C (Peptide 4_C) were injected subcutaneously (immunized) with 100 μg of the peptide of SEQ ID NO. 14, derived from Atp5o protein, emulsified in Complete Freud's Adjuvant (CFA) at day 0 and boosted with 100 g of each of the three peptides emulsified in Incomplete Freud's Adjuvant (IFA) on day 21. On day 0 and day 2, all the mice were intraperitoneally injected with 200 ng of Pertussis Toxin. Heart functionality of all mice was analyzed via echocardiography at 2, 5 and 9 weeks after the first subcutaneous injection. In FIG. 7, the results of echocardiography analysis of cardiac functionality parameters % FS and % EF of C57BL6/J mice immunized with the peptide of SEQ ID NO. 1 (14-3-3 protein), the peptide of SEQ ID NO. 5 (Snrpd1 protein), or the peptide of SEQ ID NO. 14 (Atp5o protein) are shown. Mice immunized with peptides derived from beta-adrenergic receptor and from 14-3-3, Snrpd1, and Atp5o proteins showed a significantly reduced % FS and % EF. Data are plotted as mean±SEM, (n=4-6). Two-way ANOVA and Tukey's multiple comparison test with matching subjects. * $p<0.05$,  $p<0.01$, * $p<0.001$.

EXAMPLE 6: VALIDATION OF FUNCTIONAL RELEVANCE OF IDENTIFIED ANTIGENS RECOGNIZED BY T CELLS DRIVING HF

The present inventors conducted dedicated experiments in order to assess whether human Heart Failure patients develop IgG responses against the newly-identified antigens, and thus whether the T cell-dependent antibody response to the antigens can be used to differentially identify HF patients.

ELISA assays were performed using as capture molecules the peptides of SEQ ID NO. 1 (peptide 4_A), SEQ ID NO. 5 (peptide 4_B), and SEQ ID NO. 14 (peptide 4_C), either alone or in combination. A total of 100 ng of either the peptide 4_A, peptide 4_B, or peptide 4_C, or of these peptides in combination was coated on 96-well plates overnight and blocking of non-specific binding was performed. Healthy or heart failure patient human serum samples were then applied and incubated for 1 hour. Anti-human IgG-HRP was used to detect the bound IgG antibodies present in the serum. Addition of TMB (3,3',5,5'-tetramethylbenzidine) to the wells created a colorimetric reaction, which is proportional to the presence of bound antibodies. The intensity of the colorimetric reaction was measured and the absorbance of each sample, after blank subtraction, was plotted (FIG. 8). Data were plotted as mean±SEM, (n=2); unpaired t-test. * $p<0.05$.

The results of the ELISA assays described above show that the peptides according to the invention, either alone or in combination, enabled the detection of a significant difference between HF patients and healthy controls.

EXAMPLE 7: APPLICATION OF IDENTIFIED ANTIGENS RECOGNIZED BY T CELLS DRIVING HF IN PREVENTIVE THERAPY EXPERIMENT

To assess preventive protection potential of oral tolerance with the newly identified peptides from the development of Heart Failure, the inventors pursued an oral tolerance protocol to induce cardio-specific tolerance for the peptides, followed by active induction of Heart Failure via TAC. A schematic representation of the protocol pursued by the inventors is shown in FIG. 9.

Briefly, C57BL6/J 8-week-old male mice were screened at baseline via echocardiography. Each mouse was orally fed with 0.8 mg of each peptide from group 4: the peptide of SEQ ID NO. 1 (14-3-3 protein), the peptide of SEQ ID NO. 5 (Snrpd1 protein), and the peptide of SEQ ID NO. 14 (Atp5o protein) (i.e. 0.8 mg per day of each peptide, thus 2.4 mg/day in total), diluted in 600 μl of Phosphate Buffered-Saline (PBS) or plain PBS (as control) via oral feeding (oral gavage) for 4 days in a row. Three days after the end of this procedure, on day 7, the mice underwent TAC surgery, to experimentally induce Heart Failure. Echocardiographies were performed on both groups of mice to monitor their cardiac functionality at 2, 4 and 8 weeks after TAC-surgery. As shown in FIG. 10, oral administration of peptides prevented cardiac dysfunction in TAC-operated mice. Mice that orally received the identified peptides (peptides of SEQ ID NO. 1, 5 and 14) with the tolerization protocol depicted above, showed significantly better cardiac functionality (measured as % FS and % EF, solid line) 8 weeks after surgery compared to mice treated with PBS alone (dotted line). Data were plotted as mean±SEM, (n=8-11). Two-way ANOVA and Tukey's multiple comparison test with matching subjects.  $p < 0.01$, *$p < 0.001$.

Moreover, the present inventors found that oral administration of peptides induces oral tolerance towards the fed peptides via retinoic acid production, known to promote the generation of induced immunosuppressive regulatory T cells. Briefly, eight weeks after oral tolerance induction in TAC-operated mice, mesenteric lymph nodes (MLN) were collected and dendritic cells (DC) were isolated for FACS analysis. Aldehyde dehydrogenase (ALDH) production of retinoic acid from the DC was measured via Aldefluor Fluorescent dye. FACS analysis of DC isolated from MLN of mice fed with the peptides of SEQ ID NO. 1, 5 and 14 showed a significant increase in ALDH activity (FIG. 11), which is a proxy for retinoic acid production. Retinoic acid produced by tolerogenic DC contributes to Regulatory T cell (Treg) generation, essential for tolerance induction. The bar graphs in FIG. 11 illustrate that both percentage of ALDH positive DC and the mean fluorescence intensity (MFI), induced by the presence of the fluorescent dye, in mice orally fed with the peptides compared to mice fed with PBS alone showed a significant increase. Data are plotted as mean±SEM, (n=7-8). Unpaired t-test. * $p < 0.05$.

---

The invention claimed is:

1. A method for treating a cardiovascular disease in an individual in need thereof, the method comprising:

(a) providing a pharmaceutical composition comprising a peptide consisting of a sequence as set forth in SEQ ID NO. 1;

(b) administering to the individual in need thereof the pharmaceutical composition of (a).

2. The method of claim 1, wherein the cardiovascular disease is a heart failure.

3. The method of claim 1, wherein the pharmaceutical composition further comprises a pharmaceutically acceptable carrier, vehicle, excipient and/or diluent.

4. The method of claim 1, wherein the pharmaceutical composition is administered to the individual in need thereof orally.

5. The method of claim 1, wherein the pharmaceutical composition does not comprise an adjuvant.

6. The method of claim 1, wherein the pharmaceutical composition is formulated as a food, a feed or a drink product.

7. The method of claim 2, wherein the heart failure is not resulting from an autoimmune myocarditis.

8. The method of claim 1, wherein the pharmaceutical composition further comprises a peptide consisting of a sequence as set forth in SEQ ID NO:5, and a peptide consisting of a sequence as set forth in SEQ ID NO: 6.

9. The method of claim 1, wherein the pharmaceutical composition further comprises a peptide consisting of a sequence as set forth in SEQ ID NO:5, and a peptide consisting of a sequence as set forth in SEQ ID NO: 14.

10. The method of claim 1, further comprising administering a peptide consisting of a sequence as set forth in SEQ ID NO:5, and a peptide consisting of a sequence as set forth in SEQ ID NO:6.

11. The method of claim 1, further comprising administering a peptide consisting of a sequence as set forth in SEQ ID NO:5, and a peptide consisting of a sequence as set forth in SEQ ID NO:14.

* * * * *

SEQUENCE LISTING

```
<160>  NUMBER OF SEQ ID NOS: 80

<210>  SEQ ID NO 1
<211>  LENGTH: 15
<212>  TYPE: PRT
<213>  ORGANISM: Homo sapiens

<400>  SEQUENCE: 1

Leu Gly Leu Ala Leu Asn Phe Ser Val Phe Tyr Tyr Glu Ile Leu
1               5                   10                  15

<210>  SEQ ID NO 2
<211>  LENGTH: 14
<212>  TYPE: PRT
<213>  ORGANISM: Homo sapiens

<400>  SEQUENCE: 2

Leu Gly Leu Ala Leu Asn Phe Ser Val Phe Tyr Tyr Glu Ile
1               5                   10

<210>  SEQ ID NO 3
<211>  LENGTH: 14
<212>  TYPE: PRT
<213>  ORGANISM: Homo sapiens

<400>  SEQUENCE: 3

Leu Gly Leu Ala Leu Asn Tyr Ser Val Phe Tyr Tyr Glu Ile
1               5                   10

<210>  SEQ ID NO 4
<211>  LENGTH: 14
<212>  TYPE: PRT
<213>  ORGANISM: Homo sapiens

<400>  SEQUENCE: 4

Leu Gly Leu Ala Leu Asn Phe Ser Val Phe His Tyr Glu Ile
1               5                   10

<210>  SEQ ID NO 5
<211>  LENGTH: 25
<212>  TYPE: PRT
<213>  ORGANISM: Homo sapiens
```

-continued

```
<400> SEQUENCE: 5

Glu Pro Val Gln Leu Glu Thr Leu Ser Ile Arg Gly Asn Asn Ile Arg
1               5                   10                  15

Tyr Phe Ile Leu Pro Asp Ser Leu Pro
            20                  25

<210> SEQ ID NO 6
<211> LENGTH: 15
<212> TYPE: PRT
<213> ORGANISM: Homo sapiens

<400> SEQUENCE: 6

Leu Thr Thr Asn Leu Ile Asn Leu Leu Ala Glu Asn Gly Arg Leu
1               5                   10                  15

<210> SEQ ID NO 7
<211> LENGTH: 13
<212> TYPE: PRT
<213> ORGANISM: Homo sapiens

<400> SEQUENCE: 7

Leu Thr Ala Asn Leu Ile His Leu Ser Glu Asn Arg Leu
1               5                   10

<210> SEQ ID NO 8
<211> LENGTH: 7
<212> TYPE: PRT
<213> ORGANISM: Canis lupus familiaris

<400> SEQUENCE: 8

Leu Gly Leu Ala Leu Asn Phe
1               5

<210> SEQ ID NO 9
<211> LENGTH: 14
<212> TYPE: PRT
<213> ORGANISM: Canis lupus familiaris

<400> SEQUENCE: 9

Thr Ser Asn Leu Ile Asn Leu Leu Ala Glu Asn Gly Arg Leu
1               5                   10

<210> SEQ ID NO 10
<211> LENGTH: 8
<212> TYPE: PRT
<213> ORGANISM: Canis lupus familiaris

<400> SEQUENCE: 10

Leu Met Asn Leu Leu Ala Asn Gly
1               5

<210> SEQ ID NO 11
<211> LENGTH: 9
<212> TYPE: PRT
<213> ORGANISM: Felis catus

<400> SEQUENCE: 11

Leu Gly Asn Phe Ser Val Phe Tyr Tyr
1               5

<210> SEQ ID NO 12
<211> LENGTH: 7
<212> TYPE: PRT
<213> ORGANISM: Felis catus
```

<400> SEQUENCE: 12

Leu Asn Phe Gly Val Phe Tyr
1               5

<210> SEQ ID NO 13
<211> LENGTH: 15
<212> TYPE: PRT
<213> ORGANISM: Felis catus

<400> SEQUENCE: 13

Leu Thr Cys Asn Leu Ile Asn Leu Leu Ala Glu Asn Gly Arg Leu
1               5                   10                  15

<210> SEQ ID NO 14
<211> LENGTH: 15
<212> TYPE: PRT
<213> ORGANISM: Mus musculus

<400> SEQUENCE: 14

Leu Thr Ala Asn Leu Met Asn Leu Leu Ala Glu Asn Gly Arg Leu
1               5                   10                  15

<210> SEQ ID NO 15
<211> LENGTH: 22
<212> TYPE: PRT
<213> ORGANISM: Mus musculus

<400> SEQUENCE: 15

Ser Ala Pro Leu Ser Gln Gln Trp Thr Ala Gly Met Gly Leu Leu Leu
1               5                   10                  15

Ala Leu Ile Val Leu Leu
            20

<210> SEQ ID NO 16
<211> LENGTH: 18
<212> TYPE: PRT
<213> ORGANISM: Mus musculus

<400> SEQUENCE: 16

Lys Ala Leu Lys Thr Leu Gly Ile Ile Met Gly Val Phe Thr Leu Cys
1               5                   10                  15

Trp Leu

<210> SEQ ID NO 17
<211> LENGTH: 16
<212> TYPE: PRT
<213> ORGANISM: Mus musculus

<400> SEQUENCE: 17

His Arg Asp Leu Val Pro Asp Arg Leu Phe Val Phe Phe Asn Trp Leu
1               5                   10                  15

<210> SEQ ID NO 18
<211> LENGTH: 255
<212> TYPE: PRT
<213> ORGANISM: Homo sapiens

<400> SEQUENCE: 18

Met Asp Asp Arg Glu Asp Leu Val Tyr Gln Ala Lys Leu Ala Glu Gln
1               5                   10                  15

Ala Glu Arg Tyr Asp Glu Met Val Glu Ser Met Lys Lys Val Ala Gly
            20                  25                  30

-continued

```
Met Asp Val Glu Leu Thr Val Glu Glu Arg Asn Leu Leu Ser Val Ala
        35                  40                  45

Tyr Lys Asn Val Ile Gly Ala Arg Arg Ala Ser Trp Arg Ile Ile Ser
    50                  55                  60

Ser Ile Glu Gln Lys Glu Glu Asn Lys Gly Gly Glu Asp Lys Leu Lys
65                  70                  75                  80

Met Ile Arg Glu Tyr Arg Gln Met Val Glu Thr Glu Leu Lys Leu Ile
                85                  90                  95

Cys Cys Asp Ile Leu Asp Val Leu Asp Lys His Leu Ile Pro Ala Ala
                100                 105                 110

Asn Thr Gly Glu Ser Lys Val Phe Tyr Tyr Lys Met Lys Gly Asp Tyr
                115                 120                 125

His Arg Tyr Leu Ala Glu Phe Ala Thr Gly Asn Asp Arg Lys Glu Ala
        130                 135                 140

Ala Glu Asn Ser Leu Val Ala Tyr Lys Ala Ala Ser Asp Ile Ala Met
145                 150                 155                 160

Thr Glu Leu Pro Pro Thr His Pro Ile Arg Leu Gly Leu Ala Leu Asn
                165                 170                 175

Phe Ser Val Phe Tyr Tyr Glu Ile Leu Asn Ser Pro Asp Arg Ala Cys
                180                 185                 190

Arg Leu Ala Lys Ala Ala Phe Asp Asp Ala Ile Ala Glu Leu Asp Thr
                195                 200                 205

Leu Ser Glu Glu Ser Tyr Lys Asp Ser Thr Leu Ile Met Gln Leu Leu
        210                 215                 220

Arg Asp Asn Leu Thr Leu Trp Thr Ser Asp Met Gln Gly Asp Gly Glu
225                 230                 235                 240

Glu Gln Asn Lys Glu Ala Leu Gln Asp Val Glu Asp Glu Asn Gln
                245                 250                 255
```

```
<210> SEQ ID NO 19
<211> LENGTH: 240
<212> TYPE: PRT
<213> ORGANISM: Homo sapiens

<400> SEQUENCE: 19
```

```
Met Asp Asp Arg Glu Asp Leu Val Tyr Gln Ala Lys Leu Ala Glu Gln
1                   5                   10                  15

Ala Glu Arg Tyr Asp Glu Met Val Glu Ser Met Lys Lys Val Ala Gly
                20                  25                  30

Met Asp Val Glu Leu Thr Val Glu Glu Arg Asn Leu Leu Ser Val Ala
        35                  40                  45

Tyr Lys Asn Val Ile Gly Ala Arg Arg Ala Ser Trp Arg Ile Ile Ser
    50                  55                  60

Ser Ile Glu Gln Lys Glu Glu Asn Lys Gly Gly Glu Asp Lys Leu Lys
65                  70                  75                  80

Met Ile Arg Glu Tyr Arg Gln Met Val Glu Thr Glu Leu Lys Leu Ile
                85                  90                  95

Cys Cys Asp Ile Leu Asp Val Leu Asp Lys His Leu Ile Pro Ala Ala
                100                 105                 110

Asn Thr Gly Glu Ser Lys Val Phe Tyr Tyr Lys Met Lys Gly Asp Tyr
                115                 120                 125

His Arg Tyr Leu Ala Glu Phe Ala Thr Gly Asn Asp Arg Lys Glu Ala
        130                 135                 140

Ala Glu Asn Ser Leu Val Ala Tyr Lys Ala Ala Ser Asp Ile Ala Met
```

-continued

```
145                 150                 155                 160

Thr Glu Leu Pro Pro Thr His Pro Ile Arg Leu Gly Leu Ala Leu Asn
                165                 170                 175

Phe Ser Val Phe Tyr Tyr Glu Ile Leu Asn Ser Pro Asp Arg Ala Cys
                180                 185                 190

Arg Leu Ala Lys Ala Ala Phe Asp Asp Ala Ile Ala Glu Leu Asp Thr
                195                 200                 205

Leu Ser Glu Gly Ser Tyr Lys Asp Ser Thr Leu Ile Met Gln Leu Leu
        210                 215                 220

Arg Asp Asn Leu Thr Leu Trp Thr Ser Asp Met Gln Gly Asp Asp Ser
225                 230                 235                 240

<210> SEQ ID NO 20
<211> LENGTH: 218
<212> TYPE: PRT
<213> ORGANISM: Homo sapiens

<400> SEQUENCE: 20

Met Val Glu Ser Met Lys Lys Val Ala Gly Met Asp Val Glu Leu Thr
1               5                   10                  15

Val Glu Glu Arg Asn Leu Leu Ser Val Ala Tyr Lys Asn Val Ile Gly
                20                  25                  30

Ala Arg Arg Ala Ser Trp Arg Ile Ile Ser Ser Ile Glu Gln Lys Glu
        35                  40                  45

Glu Asn Lys Gly Gly Glu Asp Lys Leu Lys Met Ile Arg Glu Tyr Arg
        50                  55                  60

Gln Met Val Glu Thr Glu Leu Lys Leu Ile Cys Cys Asp Ile Leu Asp
65                  70                  75                  80

Val Leu Asp Lys His Leu Ile Pro Ala Ala Asn Thr Gly Glu Ser Lys
                85                  90                  95

Val Phe Tyr Tyr Lys Met Lys Gly Asp Tyr His Arg Tyr Leu Ala Glu
                100                 105                 110

Phe Ala Thr Gly Asn Asp Arg Lys Glu Ala Ala Glu Asn Ser Leu Val
        115                 120                 125

Ala Tyr Lys Ala Ala Ser Asp Ile Ala Met Thr Glu Leu Pro Pro Thr
        130                 135                 140

His Pro Ile Arg Leu Gly Leu Ala Leu Asn Phe Ser Val Phe Tyr Tyr
145                 150                 155                 160

Glu Ile Leu Asn Ser Pro Asp Arg Ala Cys Arg Leu Ala Lys Ala Ala
                165                 170                 175

Phe Asp Asp Ala Ile Ala Glu Leu Asp Thr Leu Ser Glu Glu Ser Tyr
                180                 185                 190

Lys Asp Ser Thr Leu Ile Met Gln Leu Leu Arg Asp Asn Leu Thr Leu
        195                 200                 205

Trp Thr Ser Asp Met Gln Gly Asp Asp Ser
        210                 215

<210> SEQ ID NO 21
<211> LENGTH: 244
<212> TYPE: PRT
<213> ORGANISM: Homo sapiens

<400> SEQUENCE: 21

Met Thr Met Asp Lys Ser Glu Leu Val Gln Lys Ala Lys Leu Ala Glu
1               5                   10                  15

Gln Ala Glu Arg Tyr Asp Asp Met Ala Ala Ala Met Lys Ala Val Thr
```

-continued

```
                 20                 25                 30

Glu Gln Gly His Glu Leu Ser Asn Glu Glu Arg Asn Leu Leu Ser Val
            35                 40                 45

Ala Tyr Lys Asn Val Val Gly Ala Arg Arg Ser Ser Trp Arg Val Ile
        50                 55                 60

Ser Ser Ile Glu Gln Lys Thr Glu Arg Asn Glu Lys Lys Gln Gln Met
65                 70                 75                 80

Gly Lys Glu Tyr Arg Glu Lys Ile Glu Ala Glu Leu Gln Asp Ile Cys
                85                 90                 95

Asn Asp Val Leu Glu Leu Leu Asp Lys Tyr Leu Ile Pro Asn Ala Thr
            100                105                110

Gln Pro Glu Ser Lys Val Phe Tyr Leu Lys Met Lys Gly Asp Tyr Phe
        115                120                125

Arg Tyr Leu Ser Glu Val Ala Ser Gly Asp Asn Lys Gln Thr Thr Val
        130                135                140

Ser Asn Ser Gln Gln Ala Tyr Gln Glu Ala Phe Glu Ile Ser Lys Lys
145                150                155                160

Glu Met Gln Pro Thr His Pro Ile Arg Leu Gly Leu Ala Leu Asn Phe
                165                170                175

Ser Val Phe Tyr Tyr Glu Ile Leu Asn Ser Pro Glu Lys Ala Cys Ser
            180                185                190

Leu Ala Lys Thr Ala Phe Asp Glu Ala Ile Ala Glu Leu Asp Thr Leu
        195                200                205

Asn Glu Glu Ser Tyr Lys Asp Ser Thr Leu Ile Met Gln Leu Leu Arg
        210                215                220

Asp Asn Leu Thr Leu Trp Thr Ser Glu Asn Gln Gly Asp Glu Gly Asp
225                230                235                240

Ala Gly Glu Gly
```

<210> SEQ ID NO 22
<211> LENGTH: 245
<212> TYPE: PRT
<213> ORGANISM: Homo sapiens

<400> SEQUENCE: 22

```
Met Glu Lys Thr Glu Leu Ile Gln Lys Ala Lys Leu Ala Glu Gln Ala
1                  5                 10                 15

Glu Arg Tyr Asp Asp Met Ala Thr Cys Met Lys Ala Val Thr Glu Gln
                20                 25                 30

Gly Ala Glu Leu Ser Asn Glu Glu Arg Asn Leu Leu Ser Val Ala Tyr
            35                 40                 45

Lys Asn Val Val Gly Gly Arg Arg Ser Ala Trp Arg Val Ile Ser Ser
        50                 55                 60

Ile Glu Gln Lys Thr Asp Thr Ser Asp Lys Lys Leu Gln Leu Ile Lys
65                 70                 75                 80

Asp Tyr Arg Glu Lys Val Glu Ser Glu Leu Arg Ser Ile Cys Thr Thr
                85                 90                 95

Val Leu Glu Leu Leu Asp Lys Tyr Leu Ile Ala Asn Ala Thr Asn Pro
            100                105                110

Glu Ser Lys Val Phe Tyr Leu Lys Met Lys Gly Asp Tyr Phe Arg Tyr
        115                120                125

Leu Ala Glu Val Ala Cys Gly Asp Asp Arg Lys Gln Thr Ile Asp Asn
        130                135                140

Ser Gln Gly Ala Tyr Gln Glu Ala Phe Asp Ile Ser Lys Lys Glu Met
```

-continued

```
145             150             155             160

Gln Pro Thr His Pro Ile Arg Leu Gly Leu Ala Leu Asn Phe Ser Val
                165             170             175

Phe Tyr Tyr Glu Ile Leu Asn Asn Pro Glu Leu Ala Cys Thr Leu Ala
                180             185             190

Lys Thr Ala Phe Asp Glu Ala Ile Ala Glu Leu Asp Thr Leu Asn Glu
                195             200             205

Asp Ser Tyr Lys Asp Ser Thr Leu Ile Met Gln Leu Leu Arg Asp Asn
        210             215             220

Leu Thr Leu Trp Thr Ser Asp Ser Ala Gly Glu Glu Cys Asp Ala Ala
225             230             235             240

Glu Gly Ala Glu Asn
                245
```

```
<210> SEQ ID NO 23
<211> LENGTH: 253
<212> TYPE: PRT
<213> ORGANISM: Homo sapiens

<400> SEQUENCE: 23

Met Asp Lys Asn Glu Leu Val Gln Lys Ala Lys Leu Ala Glu Gln Ala
1               5               10              15

Glu Arg Tyr Asp Asp Met Ala Ala Cys Met Lys Ser Val Thr Glu Gln
                20              25              30

Gly Ala Glu Leu Ser Asn Glu Glu Arg Asn Leu Leu Ser Val Ala Tyr
        35              40              45

Lys Asn Val Val Gly Ala Arg Arg Ser Ser Trp Arg Val Val Ser Ser
        50              55              60

Ile Glu Gln Lys Thr Glu Gly Ala Glu Lys Lys Gln Gln Met Ala Arg
65              70              75              80

Glu Tyr Arg Glu Lys Ile Glu Thr Glu Leu Arg Asp Ile Cys Asn Asp
                85              90              95

Val Leu Ser Leu Leu Glu Lys Phe Leu Ile Pro Asn Ala Ser Gln Ala
                100             105             110

Glu Ser Lys Val Phe Tyr Leu Lys Met Lys Gly Asp Tyr Tyr Arg Tyr
        115             120             125

Leu Ala Glu Val Ala Ala Gly Asp Asp Lys Lys Gly Ile Val Asp Gln
        130             135             140

Ser Gln Gln Ala Tyr Gln Glu Ala Phe Glu Ile Ser Lys Lys Glu Met
145             150             155             160

Gln Pro Thr His Pro Ile Arg Leu Gly Leu Ala Leu Asn Phe Ser Val
                165             170             175

Phe Tyr Tyr Glu Ile Leu Asn Ser Pro Glu Lys Ala Cys Ser Leu Ala
                180             185             190

Lys Thr Ala Phe Asp Glu Ala Ile Ala Glu Leu Asp Thr Leu Ser Glu
                195             200             205

Glu Ser Tyr Lys Asp Ser Thr Leu Ile Met Gln Leu Leu Arg Asp Asn
        210             215             220

Leu Thr Leu Trp Thr Ser Asp Thr Gln Gly Asp Glu Ala Glu Ala Gly
225             230             235             240

Glu Gly Gly Glu Asn Ser Asp Met Gln Gly Asp Asp Ser
                245             250
```

```
<210> SEQ ID NO 24
<211> LENGTH: 246
```

```
<212> TYPE: PRT
<213> ORGANISM: Homo sapiens

<400> SEQUENCE: 24

Met Gly Asp Arg Glu Gln Leu Leu Gln Arg Ala Arg Leu Ala Glu Gln
1               5                   10                  15

Ala Glu Arg Tyr Asp Asp Met Ala Ser Ala Met Lys Ala Val Thr Glu
                20                  25                  30

Leu Asn Glu Pro Leu Ser Asn Glu Asp Arg Asn Leu Leu Ser Val Ala
            35                  40                  45

Tyr Lys Asn Val Val Gly Ala Arg Arg Ser Ser Trp Arg Val Ile Ser
        50                  55                  60

Ser Ile Glu Gln Lys Thr Met Ala Asp Gly Asn Glu Lys Lys Leu Glu
65                  70                  75                  80

Lys Val Lys Ala Tyr Arg Glu Lys Ile Glu Lys Glu Leu Glu Thr Val
                85                  90                  95

Cys Asn Asp Val Leu Ser Leu Leu Asp Lys Phe Leu Ile Lys Asn Cys
                100                 105                 110

Asn Asp Phe Gln Tyr Glu Ser Lys Val Phe Tyr Leu Lys Met Lys Gly
            115                 120                 125

Asp Tyr Tyr Arg Tyr Leu Ala Glu Val Ala Ser Gly Glu Lys Lys Asn
        130                 135                 140

Ser Val Val Glu Ala Ser Glu Ala Ala Tyr Lys Glu Ala Phe Glu Ile
145                 150                 155                 160

Ser Lys Glu Gln Met Gln Pro Thr His Pro Ile Arg Leu Gly Leu Ala
                165                 170                 175

Leu Asn Phe Ser Val Phe Tyr Tyr Glu Ile Gln Asn Ala Pro Glu Gln
                180                 185                 190

Ala Cys Leu Leu Ala Lys Gln Ala Phe Asp Asp Ala Ile Ala Glu Leu
            195                 200                 205

Asp Thr Leu Asn Glu Asp Ser Tyr Lys Asp Ser Thr Leu Ile Met Gln
        210                 215                 220

Leu Leu Arg Asp Asn Leu Thr Leu Trp Thr Ser Asp Gln Gln Asp Glu
225                 230                 235                 240

Glu Ala Gly Glu Gly Asn
                245

<210> SEQ ID NO 25
<211> LENGTH: 247
<212> TYPE: PRT
<213> ORGANISM: Homo sapiens

<400> SEQUENCE: 25

Met Val Asp Arg Glu Gln Leu Val Gln Lys Ala Arg Leu Ala Glu Gln
1               5                   10                  15

Ala Glu Arg Tyr Asp Asp Met Ala Ala Ala Met Lys Asn Val Thr Glu
                20                  25                  30

Leu Asn Glu Pro Leu Ser Asn Glu Glu Arg Asn Leu Leu Ser Val Ala
            35                  40                  45

Tyr Lys Asn Val Val Gly Ala Arg Arg Ser Ser Trp Arg Val Ile Ser
        50                  55                  60

Ser Ile Glu Gln Lys Thr Ser Ala Asp Gly Asn Glu Lys Lys Ile Glu
65                  70                  75                  80

Met Val Arg Ala Tyr Arg Glu Lys Ile Glu Lys Glu Leu Glu Ala Val
                85                  90                  95
```

-continued

```
Cys Gln Asp Val Leu Ser Leu Leu Asp Asn Tyr Leu Ile Lys Asn Cys
            100                 105                 110

Ser Glu Thr Gln Tyr Glu Ser Lys Val Phe Tyr Leu Lys Met Lys Gly
        115                 120                 125

Asp Tyr Tyr Arg Tyr Leu Ala Glu Val Ala Thr Gly Glu Lys Arg Ala
    130                 135                 140

Thr Val Val Glu Ser Ser Glu Lys Ala Tyr Ser Glu Ala His Glu Ile
145                 150                 155                 160

Ser Lys Glu His Met Gln Pro Thr His Pro Ile Arg Leu Gly Leu Ala
                165                 170                 175

Leu Asn Tyr Ser Val Phe Tyr Tyr Glu Ile Gln Asn Ala Pro Glu Gln
            180                 185                 190

Ala Cys His Leu Ala Lys Thr Ala Phe Asp Asp Ala Ile Ala Glu Leu
        195                 200                 205

Asp Thr Leu Asn Glu Asp Ser Tyr Lys Asp Ser Thr Leu Ile Met Gln
    210                 215                 220

Leu Leu Arg Asp Asn Leu Thr Leu Trp Thr Ser Asp Gln Gln Asp Asp
225                 230                 235                 240

Asp Gly Gly Glu Gly Asn Asn
                245
```

```
<210> SEQ ID NO 26
<211> LENGTH: 248
<212> TYPE: PRT
<213> ORGANISM: Homo sapiens

<400> SEQUENCE: 26

Met Glu Arg Ala Ser Leu Ile Gln Lys Ala Lys Leu Ala Glu Gln Ala
1               5                   10                  15

Glu Arg Tyr Glu Asp Met Ala Ala Phe Met Lys Gly Ala Val Glu Lys
            20                  25                  30

Gly Glu Glu Leu Ser Cys Glu Glu Arg Asn Leu Leu Ser Val Ala Tyr
        35                  40                  45

Lys Asn Val Val Gly Gly Gln Arg Ala Ala Trp Arg Val Leu Ser Ser
    50                  55                  60

Ile Glu Gln Lys Ser Asn Glu Glu Gly Ser Glu Glu Lys Gly Pro Glu
65                  70                  75                  80

Val Arg Glu Tyr Arg Glu Lys Val Glu Thr Glu Leu Gln Gly Val Cys
                85                  90                  95

Asp Thr Val Leu Gly Leu Leu Asp Ser His Leu Ile Lys Glu Ala Gly
            100                 105                 110

Asp Ala Glu Ser Arg Val Phe Tyr Leu Lys Met Lys Gly Asp Tyr Tyr
        115                 120                 125

Arg Tyr Leu Ala Glu Val Ala Thr Gly Asp Asp Lys Lys Arg Ile Ile
    130                 135                 140

Asp Ser Ala Arg Ser Ala Tyr Gln Glu Ala Met Asp Ile Ser Lys Lys
145                 150                 155                 160

Glu Met Pro Pro Thr Asn Pro Ile Arg Leu Gly Leu Ala Leu Asn Phe
                165                 170                 175

Ser Val Phe His Tyr Glu Ile Ala Asn Ser Pro Glu Glu Ala Ile Ser
            180                 185                 190

Leu Ala Lys Thr Thr Phe Asp Glu Ala Met Ala Asp Leu His Thr Leu
        195                 200                 205

Ser Glu Asp Ser Tyr Lys Asp Ser Thr Leu Ile Met Gln Leu Leu Arg
    210                 215                 220
```

-continued

```
Asp Asn Leu Thr Leu Trp Thr Ala Asp Asn Ala Gly Glu Glu Gly Gly
225                 230                 235                 240

Glu Ala Pro Gln Glu Pro Gln Ser
                245

<210> SEQ ID NO 27
<211> LENGTH: 119
<212> TYPE: PRT
<213> ORGANISM: Homo sapiens

<400> SEQUENCE: 27

Met Lys Leu Val Arg Phe Leu Met Lys Leu Ser His Glu Thr Val Thr
1               5                   10                  15

Ile Glu Leu Lys Asn Gly Thr Gln Val His Gly Thr Ile Thr Gly Val
                20                  25                  30

Asp Val Ser Met Asn Thr His Leu Lys Ala Val Lys Met Thr Leu Lys
                35                  40                  45

Asn Arg Glu Pro Val Gln Leu Glu Thr Leu Ser Ile Arg Gly Asn Asn
        50                  55                  60

Ile Arg Tyr Phe Ile Leu Pro Asp Ser Leu Pro Leu Asp Thr Leu Leu
65                  70                  75                  80

Val Asp Val Glu Pro Lys Val Lys Ser Lys Lys Arg Glu Ala Val Ala
                85                  90                  95

Gly Arg Gly Arg Gly Arg Gly Arg Gly Arg Gly Arg Gly Arg Gly Arg
                100                 105                 110

Gly Arg Gly Gly Pro Arg Arg
        115

<210> SEQ ID NO 28
<211> LENGTH: 213
<212> TYPE: PRT
<213> ORGANISM: Homo sapiens

<400> SEQUENCE: 28

Met Ala Ala Pro Ala Val Ser Gly Leu Ser Arg Gln Val Arg Cys Phe
1               5                   10                  15

Ser Thr Ser Val Val Arg Pro Phe Ala Lys Leu Val Arg Pro Pro Val
                20                  25                  30

Gln Val Tyr Gly Ile Glu Gly Arg Tyr Ala Thr Ala Leu Tyr Ser Ala
                35                  40                  45

Ala Ser Lys Gln Asn Lys Leu Glu Gln Val Glu Lys Glu Leu Leu Arg
        50                  55                  60

Val Ala Gln Ile Leu Lys Glu Pro Lys Val Ala Ala Ser Val Leu Asn
65                  70                  75                  80

Pro Tyr Val Lys Arg Ser Ile Lys Val Lys Ser Leu Asn Asp Ile Thr
                85                  90                  95

Ala Lys Glu Arg Phe Ser Pro Leu Thr Thr Asn Leu Ile Asn Leu Leu
                100                 105                 110

Ala Glu Asn Gly Arg Leu Ser Asn Thr Gln Gly Val Val Ser Ala Phe
        115                 120                 125

Ser Thr Met Met Ser Val His Arg Gly Glu Val Pro Cys Thr Val Thr
        130                 135                 140

Ser Ala Ser Pro Leu Glu Glu Ala Thr Leu Ser Glu Leu Lys Thr Val
145                 150                 155                 160

Leu Lys Ser Phe Leu Ser Gln Gly Gln Val Leu Lys Leu Glu Ala Lys
                165                 170                 175
```

```
Thr Asp Pro Ser Ile Leu Gly Gly Met Ile Val Arg Ile Gly Glu Lys
        180                 185                 190

Tyr Val Asp Met Ser Val Lys Thr Lys Ile Gln Lys Leu Gly Arg Ala
        195                 200                 205

Met Arg Glu Ile Val
    210
```

<210> SEQ ID NO 29
<211> LENGTH: 858
<212> TYPE: PRT
<213> ORGANISM: Homo sapiens

<400> SEQUENCE: 29

```
Met Gly Asp His Leu Asp Leu Leu Gly Val Val Leu Met Ala Gly
1               5               10                  15

Pro Val Phe Gly Ile Pro Ser Cys Ser Phe Asp Gly Arg Ile Ala Phe
            20              25                  30

Tyr Arg Phe Cys Asn Leu Thr Gln Val Pro Gln Val Leu Asn Thr Thr
        35                  40                  45

Glu Arg Leu Leu Leu Ser Phe Asn Tyr Ile Arg Thr Val Thr Ala Ser
    50                  55                  60

Ser Phe Pro Phe Leu Glu Gln Leu Gln Leu Leu Glu Leu Gly Ser Gln
65                  70                  75                  80

Tyr Thr Pro Leu Thr Ile Asp Lys Glu Ala Phe Arg Asn Leu Pro Asn
                85                  90                  95

Leu Arg Ile Leu Asp Leu Gly Ser Ser Lys Ile Tyr Phe Leu His Pro
            100                 105                 110

Asp Ala Phe Gln Gly Leu Phe His Leu Phe Glu Leu Arg Leu Tyr Phe
        115                 120                 125

Cys Gly Leu Ser Asp Ala Val Leu Lys Asp Gly Tyr Phe Arg Asn Leu
    130                 135                 140

Lys Ala Leu Thr Arg Leu Asp Leu Ser Lys Asn Gln Ile Arg Ser Leu
145                 150                 155                 160

Tyr Leu His Pro Ser Phe Gly Lys Leu Asn Ser Leu Lys Ser Ile Asp
                165                 170                 175

Phe Ser Ser Asn Gln Ile Phe Leu Val Cys Glu His Glu Leu Glu Pro
            180                 185                 190

Leu Gln Gly Lys Thr Leu Ser Phe Phe Ser Leu Ala Ala Asn Ser Leu
        195                 200                 205

Tyr Ser Arg Val Ser Val Asp Trp Gly Lys Cys Met Asn Pro Phe Arg
    210                 215                 220

Asn Met Val Leu Glu Ile Leu Asp Val Ser Gly Asn Gly Trp Thr Val
225                 230                 235                 240

Asp Ile Thr Gly Asn Phe Ser Asn Ala Ile Ser Lys Ser Gln Ala Phe
                245                 250                 255

Ser Leu Ile Leu Ala His His Ile Met Gly Ala Gly Phe Gly Phe His
            260                 265                 270

Asn Ile Lys Asp Pro Asp Gln Asn Thr Phe Ala Gly Leu Ala Arg Ser
        275                 280                 285

Ser Val Arg His Leu Asp Leu Ser His Gly Phe Val Phe Ser Leu Asn
    290                 295                 300

Ser Arg Val Phe Glu Thr Leu Lys Asp Leu Lys Val Leu Asn Leu Ala
305                 310                 315                 320

Tyr Asn Lys Ile Asn Lys Ile Ala Asp Glu Ala Phe Tyr Gly Leu Asp
```

-continued

```
                    325                 330                 335

Asn Leu Gln Val Leu Asn Leu Ser Tyr Asn Leu Leu Gly Glu Leu Tyr
                340                 345                 350

Ser Ser Asn Phe Tyr Gly Leu Pro Lys Val Ala Tyr Ile Asp Leu Gln
                355                 360                 365

Lys Asn His Ile Ala Ile Ile Gln Asp Gln Thr Phe Lys Phe Leu Glu
        370                 375                 380

Lys Leu Gln Thr Leu Asp Leu Arg Asp Asn Ala Leu Thr Thr Ile His
385                 390                 395                 400

Phe Ile Pro Ser Ile Pro Asp Ile Phe Leu Ser Gly Asn Lys Leu Val
                    405                 410                 415

Thr Leu Pro Lys Ile Asn Leu Thr Ala Asn Leu Ile His Leu Ser Glu
                420                 425                 430

Asn Arg Leu Glu Asn Leu Asp Ile Leu Tyr Phe Leu Leu Arg Val Pro
                435                 440                 445

His Leu Gln Ile Leu Ile Leu Asn Gln Asn Arg Phe Ser Ser Cys Ser
        450                 455                 460

Gly Asp Gln Thr Pro Ser Glu Asn Pro Ser Leu Glu Gln Leu Phe Leu
465                 470                 475                 480

Gly Glu Asn Met Leu Gln Leu Ala Trp Glu Thr Glu Leu Cys Trp Asp
                485                 490                 495

Val Phe Glu Gly Leu Ser His Leu Gln Val Leu Tyr Leu Asn His Asn
                500                 505                 510

Tyr Leu Asn Ser Leu Pro Pro Gly Val Phe Ser His Leu Thr Ala Leu
                515                 520                 525

Arg Gly Leu Ser Leu Asn Ser Asn Arg Leu Thr Val Leu Ser His Asn
        530                 535                 540

Asp Leu Pro Ala Asn Leu Glu Ile Leu Asp Ile Ser Arg Asn Gln Leu
545                 550                 555                 560

Leu Ala Pro Asn Pro Asp Val Phe Val Ser Leu Ser Val Leu Asp Ile
                565                 570                 575

Thr His Asn Lys Phe Ile Cys Glu Cys Glu Leu Ser Thr Phe Ile Asn
                580                 585                 590

Trp Leu Asn His Thr Asn Val Thr Ile Ala Gly Pro Pro Ala Asp Ile
        595                 600                 605

Tyr Cys Val Tyr Pro Asp Ser Phe Ser Gly Val Ser Leu Phe Ser Leu
        610                 615                 620

Ser Thr Glu Gly Cys Asp Glu Glu Glu Val Leu Lys Ser Leu Lys Phe
625                 630                 635                 640

Ser Leu Phe Ile Val Cys Thr Val Thr Leu Thr Leu Phe Leu Met Thr
                645                 650                 655

Ile Leu Thr Val Thr Lys Phe Arg Gly Phe Cys Phe Ile Cys Tyr Lys
                660                 665                 670

Thr Ala Gln Arg Leu Val Phe Lys Asp His Pro Gln Gly Thr Glu Pro
        675                 680                 685

Asp Met Tyr Lys Tyr Asp Ala Tyr Leu Cys Phe Ser Ser Lys Asp Phe
        690                 695                 700

Thr Trp Val Gln Asn Ala Leu Leu Lys His Leu Asp Thr Gln Tyr Ser
705                 710                 715                 720

Asp Gln Asn Arg Phe Asn Leu Cys Phe Glu Glu Arg Asp Phe Val Pro
                725                 730                 735

Gly Glu Asn Arg Ile Ala Asn Ile Gln Asp Ala Ile Trp Asn Ser Arg
                740                 745                 750
```

```
Lys Ile Val Cys Leu Val Ser Arg His Phe Leu Arg Asp Gly Trp Cys
        755                 760                 765

Leu Glu Ala Phe Ser Tyr Ala Gln Gly Arg Cys Leu Ser Asp Leu Asn
        770                 775                 780

Ser Ala Leu Ile Met Val Val Val Gly Ser Leu Ser Gln Tyr Gln Leu
785                 790                 795                 800

Met Lys His Gln Ser Ile Arg Gly Phe Val Gln Lys Gln Gln Tyr Leu
                805                 810                 815

Arg Trp Pro Glu Asp Phe Gln Asp Val Gly Trp Phe Leu His Lys Leu
                820                 825                 830

Ser Gln Gln Ile Leu Lys Lys Glu Lys Glu Lys Lys Asp Asn Asn
        835                 840                 845

Ile Pro Leu Gln Thr Val Ala Thr Ile Ser
        850                 855
```

```
<210> SEQ ID NO 30
<211> LENGTH: 262
<212> TYPE: PRT
<213> ORGANISM: Canis lupus familiaris

<400> SEQUENCE: 30

Met Asp Asp Arg Glu Asp Leu Val Tyr Gln Ala Lys Leu Ala Glu Gln
1                 5                   10                  15

Ala Glu Arg Tyr Asp Val Gln Met Ala Phe Cys Asp Glu Met Val Glu
                20                  25                  30

Ser Met Lys Lys Val Ala Gly Met Asp Val Glu Leu Thr Val Glu Glu
        35                  40                  45

Arg Asn Leu Leu Ser Val Ala Tyr Lys Asn Val Ile Gly Ala Arg Arg
        50                  55                  60

Ala Ser Trp Arg Ile Ile Ser Ser Ile Glu Gln Lys Glu Glu Asn Lys
65                  70                  75                  80

Gly Gly Glu Asp Lys Leu Lys Met Ile Arg Glu Tyr Arg Gln Met Val
                85                  90                  95

Glu Thr Glu Leu Lys Leu Ile Cys Cys Asp Ile Leu Asp Val Leu Asp
                100                 105                 110

Lys His Leu Ile Pro Ala Ala Asn Thr Gly Glu Ser Lys Val Phe Tyr
        115                 120                 125

Tyr Lys Met Lys Gly Asp Tyr His Arg Tyr Leu Ala Glu Phe Ala Thr
        130                 135                 140

Gly Asn Asp Arg Lys Glu Ala Ala Glu Asn Ser Leu Val Ala Tyr Lys
145                 150                 155                 160

Ala Ala Ser Asp Ile Ala Met Thr Glu Leu Pro Pro Thr His Pro Ile
                165                 170                 175

Arg Leu Gly Leu Ala Leu Asn Phe Ser Val Phe Tyr Tyr Glu Ile Leu
                180                 185                 190

Asn Ser Pro Asp Arg Ala Cys Arg Leu Ala Lys Ala Ala Phe Asp Asp
        195                 200                 205

Ala Ile Ala Glu Leu Asp Thr Leu Ser Glu Glu Ser Tyr Lys Asp Ser
        210                 215                 220

Thr Leu Ile Met Gln Leu Leu Arg Asp Asn Leu Thr Leu Trp Thr Ser
225                 230                 235                 240

Asp Met Gln Gly Asp Gly Glu Glu Gln Asn Lys Glu Ala Leu Gln Asp
                245                 250                 255

Val Glu Asp Glu Asn Gln
```

-continued

```
            260

<210> SEQ ID NO 31
<211> LENGTH: 255
<212> TYPE: PRT
<213> ORGANISM: Canis lupus familiaris

<400> SEQUENCE: 31

Met Asp Asp Arg Glu Asp Leu Val Tyr Gln Ala Lys Leu Ala Glu Gln
1               5                   10                  15

Ala Glu Arg Tyr Asp Glu Met Val Glu Ser Met Lys Lys Val Ala Gly
            20                  25                  30

Met Asp Val Glu Leu Thr Val Glu Glu Arg Asn Leu Leu Ser Val Ala
        35                  40                  45

Tyr Lys Asn Val Ile Gly Ala Arg Arg Ala Ser Trp Arg Ile Ile Ser
    50                  55                  60

Ser Ile Glu Gln Lys Glu Glu Asn Lys Gly Gly Glu Asp Lys Leu Lys
65                  70                  75                  80

Met Ile Arg Glu Tyr Arg Gln Met Val Glu Thr Glu Leu Lys Leu Ile
                85                  90                  95

Cys Cys Asp Ile Leu Asp Val Leu Asp Lys His Leu Ile Pro Ala Ala
            100                 105                 110

Asn Thr Gly Glu Ser Lys Val Phe Tyr Tyr Lys Met Lys Gly Asp Tyr
            115                 120                 125

His Arg Tyr Leu Ala Glu Phe Ala Thr Gly Asn Asp Arg Lys Glu Ala
        130                 135                 140

Ala Glu Asn Ser Leu Val Ala Tyr Lys Ala Ala Ser Asp Ile Ala Met
145                 150                 155                 160

Thr Glu Leu Pro Pro Thr His Pro Ile Arg Leu Gly Leu Ala Leu Asn
                165                 170                 175

Phe Ser Val Phe Tyr Tyr Glu Ile Leu Asn Ser Pro Asp Arg Ala Cys
                180                 185                 190

Arg Leu Ala Lys Ala Ala Phe Asp Asp Ala Ile Ala Glu Leu Asp Thr
            195                 200                 205

Leu Ser Glu Glu Ser Tyr Lys Asp Ser Thr Leu Ile Met Gln Leu Leu
        210                 215                 220

Arg Asp Asn Leu Thr Leu Trp Thr Ser Asp Met Gln Gly Asp Gly Glu
225                 230                 235                 240

Glu Gln Asn Lys Glu Ala Leu Gln Asp Val Glu Asp Glu Asn Gln
                245                 250                 255

<210> SEQ ID NO 32
<211> LENGTH: 224
<212> TYPE: PRT
<213> ORGANISM: Canis lupus familiaris

<400> SEQUENCE: 32

Met Ala Phe Cys Asp Glu Met Val Glu Ser Met Lys Lys Val Ala Gly
1               5                   10                  15

Met Asp Val Glu Leu Thr Val Glu Glu Arg Asn Leu Leu Ser Val Ala
            20                  25                  30

Tyr Lys Asn Val Ile Gly Ala Arg Arg Ala Ser Trp Arg Ile Ile Ser
        35                  40                  45

Ser Ile Glu Gln Lys Glu Glu Asn Lys Gly Gly Glu Asp Lys Leu Lys
    50                  55                  60

Met Ile Arg Glu Tyr Arg Gln Met Val Glu Thr Glu Leu Lys Leu Ile
```

```
65                    70                    75                    80

Cys Cys Asp Ile Leu Asp Val Leu Asp Lys His Leu Ile Pro Ala Ala
                85                    90                    95

Asn Thr Gly Glu Ser Lys Val Phe Tyr Tyr Lys Met Lys Gly Asp Tyr
                100                   105                   110

His Arg Tyr Leu Ala Glu Phe Ala Thr Gly Asn Asp Arg Lys Glu Ala
                115                   120                   125

Ala Glu Asn Ser Leu Val Ala Tyr Lys Ala Ala Ser Asp Ile Ala Met
                130                   135                   140

Thr Glu Leu Pro Pro Thr His Pro Ile Arg Leu Gly Leu Ala Leu Asn
145                   150                   155                   160

Phe Ser Val Phe Tyr Tyr Glu Ile Leu Asn Ser Pro Asp Arg Ala Cys
                    165                   170                   175

Arg Leu Ala Lys Ala Ala Phe Asp Asp Ala Ile Ala Glu Leu Asp Thr
                180                   185                   190

Leu Ser Glu Glu Ser Tyr Lys Asp Ser Thr Leu Ile Met Gln Leu Leu
                195                   200                   205

Arg Asp Asn Leu Thr Leu Trp Thr Ser Asp Met Gln Gly Asp Asp Ser
    210                   215                   220
```

```
<210> SEQ ID NO 33
<211> LENGTH: 267
<212> TYPE: PRT
<213> ORGANISM: Canis lupus familiaris

<400> SEQUENCE: 33

Met Ile Lys Tyr Leu Phe Ala Glu Ala Gly Lys Ile Leu Gln Asp Val
1                   5                     10                    15

Phe Ser Leu Pro Ser Cys Cys Ser Leu Leu Val Gln Met Ala Phe Cys
                20                    25                    30

Asp Glu Met Val Glu Ser Met Lys Lys Val Ala Gly Met Asp Val Glu
                35                    40                    45

Leu Thr Val Glu Glu Arg Asn Leu Leu Ser Val Ala Tyr Lys Asn Val
                50                    55                    60

Ile Gly Ala Arg Arg Ala Ser Trp Arg Ile Ile Ser Ser Ile Glu Gln
65                    70                    75                    80

Lys Glu Glu Asn Lys Gly Gly Glu Asp Lys Leu Lys Met Ile Arg Glu
                85                    90                    95

Tyr Arg Gln Met Val Glu Thr Glu Leu Lys Leu Ile Cys Cys Asp Ile
                100                   105                   110

Leu Asp Val Leu Asp Lys His Leu Ile Pro Ala Ala Asn Thr Gly Glu
                115                   120                   125

Ser Lys Val Phe Tyr Tyr Lys Met Lys Gly Asp Tyr His Arg Tyr Leu
                130                   135                   140

Ala Glu Phe Ala Thr Gly Asn Asp Arg Lys Glu Ala Ala Glu Asn Ser
145                   150                   155                   160

Leu Val Ala Tyr Lys Ala Ala Ser Asp Ile Ala Met Thr Glu Leu Pro
                    165                   170                   175

Pro Thr His Pro Ile Arg Leu Gly Leu Ala Leu Asn Phe Ser Val Phe
                180                   185                   190

Tyr Tyr Glu Ile Leu Asn Ser Pro Asp Arg Ala Cys Arg Leu Ala Lys
                195                   200                   205

Ala Ala Phe Asp Asp Ala Ile Ala Glu Leu Asp Thr Leu Ser Glu Glu
    210                   215                   220
```

Ser Tyr Lys Asp Ser Thr Leu Ile Met Gln Leu Leu Arg Asp Asn Leu
225                     230                     235                     240

Thr Leu Trp Thr Ser Asp Met Gln Gly Asp Gly Glu Glu Gln Asn Lys
                        245                     250                     255

Glu Ala Leu Gln Asp Val Glu Asp Glu Asn Gln
            260                     265

<210> SEQ ID NO 34
<211> LENGTH: 247
<212> TYPE: PRT
<213> ORGANISM: Canis lupus familiaris

<400> SEQUENCE: 34

Met Glu Lys Thr Glu Leu Ile Gln Lys Ala Lys Leu Ala Glu Gln Ala
1                   5                       10                      15

Glu Gln Ala Glu Arg Tyr Asp Asp Arg Ala Thr Cys Val Met Ala Gly
                20                      25                      30

Pro Glu Gln Gly Ala Glu Leu Ser Asn Glu Glu Arg Ser Leu Leu Ser
            35                      40                      45

Val Ala Tyr Lys Asn Val Val Gly Gly Arg Arg Ser Ala Trp Arg Val
        50                      55                      60

Ser Ser Ser Ile Glu Gln Lys Thr Asp Thr Ser Asp Lys Lys Leu Gln
65                      70                      75                      80

Leu Ile Lys Asp Cys Arg Glu Lys Val Glu Ser Glu Leu Arg Ser Ile
                85                      90                      95

Cys Thr Thr Thr Leu Glu Leu Leu Asp Lys Tyr Leu Thr Ala Asn Ala
                100                     105                     110

Thr Asn Pro Glu Ser Lys Val Phe Tyr Leu Lys Met Lys Gly Asp Tyr
            115                     120                     125

Phe Arg Tyr Leu Ala Glu Val Ala Arg Gly Asp Asp Arg Lys Gln Thr
        130                     135                     140

Ile Asp Asn Ser Gln Gly Ala Tyr Gln Glu Ala Phe Asp Ile Ser Lys
145                     150                     155                     160

Lys Glu Met Gln Pro Thr His Pro Ile Arg Leu Gly Leu Ala Leu Asn
                165                     170                     175

Phe Ser Val Phe Tyr Tyr Glu Ile Leu Asn Asn Pro Glu Leu Val Cys
            180                     185                     190

Thr Leu Ala Lys Thr Ala Phe Asp Glu Ala Ile Ala Glu Leu Gly Thr
            195                     200                     205

Leu Asn Glu Asp Ser Tyr Lys Asp Ser Thr Leu Ile Met Gln Leu Leu
        210                     215                     220

Arg Asp Asn Leu Thr Arg Thr Ser Asp Ser Ala Gly Glu Glu Cys Asp
225                     230                     235                     240

Ala Ala Glu Gly Ala Glu Asn
                245

<210> SEQ ID NO 35
<211> LENGTH: 245
<212> TYPE: PRT
<213> ORGANISM: Canis lupus familiaris

<400> SEQUENCE: 35

Met Glu Lys Thr Glu Leu Ile Gln Lys Ala Lys Leu Ala Glu Gln Ala
1                   5                       10                      15

Glu Arg Tyr Asp Asp Met Ala Thr Cys Met Lys Ala Val Thr Glu Gln
                20                      25                      30

```
Gly Ala Glu Leu Ser Asn Glu Glu Arg Asn Leu Leu Ser Val Ala Tyr
        35                  40                  45

Lys Asn Val Val Gly Gly Arg Arg Ser Ala Trp Arg Val Ile Ser Ser
    50                  55                  60

Ile Glu Gln Lys Thr Asp Thr Ser Asp Lys Lys Leu Gln Leu Ile Lys
65                  70                  75                  80

Asp Tyr Arg Glu Lys Val Glu Ser Glu Leu Arg Ser Ile Cys Thr Thr
                85                  90                  95

Val Leu Glu Leu Leu Asp Lys Tyr Leu Ile Ala Asn Ala Thr Asn Pro
            100                 105                 110

Glu Ser Lys Val Phe Tyr Leu Lys Met Lys Gly Asp Tyr Phe Arg Tyr
            115                 120                 125

Leu Ala Glu Val Ala Cys Gly Asp Asp Arg Lys Gln Thr Ile Asp Asn
        130                 135                 140

Ser Gln Gly Ala Tyr Gln Glu Ala Phe Asp Ile Ser Lys Lys Glu Met
145                 150                 155                 160

Gln Pro Thr His Pro Ile Arg Leu Gly Leu Ala Leu Asn Phe Ser Val
                165                 170                 175

Phe Tyr Tyr Glu Ile Leu Asn Asn Pro Glu Leu Ala Cys Thr Leu Ala
                180                 185                 190

Lys Thr Ala Phe Asp Glu Ala Ile Ala Glu Leu Asp Thr Leu Asn Glu
            195                 200                 205

Asp Ser Tyr Lys Asp Ser Thr Leu Ile Met Gln Leu Leu Arg Asp Asn
        210                 215                 220

Leu Thr Leu Trp Thr Ser Asp Ser Ala Gly Glu Glu Cys Asp Ala Ala
225                 230                 235                 240

Glu Gly Ala Glu Asn
                245

<210> SEQ ID NO 36
<211> LENGTH: 245
<212> TYPE: PRT
<213> ORGANISM: Canis lupus familiaris

<400> SEQUENCE: 36

Met Asp Lys Asn Glu Leu Val Gln Lys Ala Lys Leu Ala Glu Gln Ala
1               5                   10                  15

Glu Arg Tyr Asp Asp Met Ala Ala Cys Met Lys Ser Val Thr Glu Gln
            20                  25                  30

Gly Ala Glu Leu Ser Asn Glu Glu Arg Asn Leu Leu Ser Val Ala Tyr
        35                  40                  45

Lys Asn Val Val Gly Ala Arg Arg Ser Ser Trp Arg Val Val Ser Ser
    50                  55                  60

Ile Glu Gln Lys Thr Glu Gly Ala Glu Lys Lys Gln Gln Met Ala Arg
65                  70                  75                  80

Glu Tyr Arg Glu Lys Ile Glu Thr Glu Leu Arg Asp Ile Cys Asn Asp
                85                  90                  95

Val Leu Ser Leu Leu Glu Lys Phe Leu Ile Pro Asn Ala Ser Gln Ala
            100                 105                 110

Glu Ser Lys Val Phe Tyr Leu Lys Met Lys Gly Asp Tyr Tyr Arg Tyr
            115                 120                 125

Leu Ala Glu Val Ala Ala Gly Asp Asp Lys Lys Gly Ile Val Asp Gln
        130                 135                 140

Ser Gln Gln Ala Tyr Gln Glu Ala Phe Glu Ile Ser Lys Lys Glu Met
145                 150                 155                 160
```

-continued

```
Gln Pro Thr His Pro Ile Arg Leu Gly Leu Ala Leu Asn Phe Ser Val
            165                 170                 175

Phe Tyr Tyr Glu Ile Leu Asn Ser Pro Glu Lys Ala Cys Ser Leu Ala
            180                 185                 190

Lys Thr Ala Phe Asp Glu Ala Ile Ala Glu Leu Asp Thr Leu Ser Glu
        195                 200                 205

Glu Ser Tyr Lys Asp Ser Thr Leu Ile Met Gln Leu Leu Arg Asp Asn
    210                 215                 220

Leu Thr Leu Trp Thr Ser Asp Thr Gln Gly Asp Glu Ala Glu Ala Gly
225                 230                 235                 240

Glu Gly Gly Glu Asn
                245
```

```
<210> SEQ ID NO 37
<211> LENGTH: 244
<212> TYPE: PRT
<213> ORGANISM: Canis lupus familiaris

<400> SEQUENCE: 37
```

```
Met Asp Lys Ser Glu Leu Val Gln Lys Ala Lys Leu Ala Glu Gln Ala
1               5                   10                  15

Glu Arg Tyr Asp Asp Met Ala Ala Ala Met Lys Ala Val Thr Glu Gln
            20                  25                  30

Gly His Glu Leu Ser Asn Glu Glu Arg Asn Leu Leu Ser Val Ala Tyr
        35                  40                  45

Lys Asn Val Val Gly Ala Arg Arg Ser Ser Trp Arg Val Ile Ser Ser
    50                  55                  60

Ile Glu Gln Lys Thr Glu Arg Asn Glu Lys Lys Gln Gln Met Gly Lys
65                  70                  75                  80

Glu Tyr Arg Glu Lys Ile Glu Ala Glu Leu Gln Asp Ile Cys Asn Asp
                85                  90                  95

Val Leu Glu Leu Leu Asp Lys Tyr Leu Ile Pro Asn Ala Thr Gln Pro
            100                 105                 110

Glu Ser Lys Val Phe Tyr Leu Lys Met Lys Gly Asp Tyr Phe Arg Tyr
        115                 120                 125

Leu Ser Glu Val Ala Ser Gly Asp Asn Lys Gln Thr Thr Val Ser Asn
    130                 135                 140

Ser Gln Gln Ala Tyr Gln Glu Ala Phe Glu Ile Ser Lys Lys Glu Met
145                 150                 155                 160

Gln Pro Thr His Pro Ile Arg Leu Gly Leu Ala Leu Asn Phe Ser Val
            165                 170                 175

Phe Tyr Tyr Glu Ile Leu Asn Ser Pro Glu Lys Ala Cys Ser Leu Ala
            180                 185                 190

Lys Thr Ala Phe Asp Glu Ala Ile Ala Glu Leu Asp Thr Leu Asn Glu
        195                 200                 205

Glu Ser Tyr Lys Asp Ser Thr Leu Ile Met Gln Leu Leu Arg Asp Asn
    210                 215                 220

Leu Thr Leu Trp Thr Ser Glu Asn Gln Gly Asp Glu Gly Asp Ala Gly
225                 230                 235                 240

Glu Gly Glu Asn
```

```
<210> SEQ ID NO 38
<211> LENGTH: 246
<212> TYPE: PRT
<213> ORGANISM: Canis lupus familiaris
```

<400> SEQUENCE: 38

```
Met Gly Asp Arg Glu Gln Leu Leu Gln Arg Ala Arg Leu Ala Glu Gln
1               5                   10                  15

Ala Glu Arg Tyr Asp Asp Met Ala Ser Ala Met Lys Ala Val Thr Glu
                20                  25                  30

Leu Asn Glu Pro Leu Ser Asn Glu Asp Arg Asn Leu Leu Ser Val Ala
            35                  40                  45

Tyr Lys Asn Val Val Gly Ala Arg Arg Ser Ser Trp Arg Val Ile Ser
        50                  55                  60

Ser Ile Glu Gln Lys Thr Met Ala Asp Gly Asn Glu Lys Lys Leu Glu
65                  70                  75                  80

Lys Val Lys Ala Tyr Arg Glu Lys Ile Glu Lys Glu Leu Glu Thr Val
                85                  90                  95

Cys Asn Asp Val Leu Ala Leu Leu Asp Lys Phe Leu Ile Lys Asn Cys
                100                 105                 110

Asn Asp Phe Gln Tyr Glu Ser Lys Val Phe Tyr Leu Lys Met Lys Gly
            115                 120                 125

Asp Tyr Tyr Arg Tyr Leu Ala Glu Val Ala Ser Gly Glu Lys Lys Asn
        130                 135                 140

Ser Val Val Glu Ala Ser Glu Ala Ala Tyr Lys Glu Ala Phe Glu Ile
145                 150                 155                 160

Ser Lys Glu His Met Gln Pro Thr His Pro Ile Arg Leu Gly Leu Ala
                165                 170                 175

Leu Asn Phe Ser Val Phe Tyr Tyr Glu Ile Gln Asn Ala Pro Glu Gln
            180                 185                 190

Ala Cys Leu Leu Ala Lys Gln Ala Phe Asp Asp Ala Ile Ala Glu Leu
        195                 200                 205

Asp Thr Leu Asn Glu Asp Ser Tyr Lys Asp Ser Thr Leu Ile Met Gln
    210                 215                 220

Leu Leu Arg Asp Asn Leu Thr Leu Trp Thr Ser Asp Gln Gln Asp Glu
225                 230                 235                 240

Glu Ala Gly Glu Gly Asn
                245
```

<210> SEQ ID NO 39
<211> LENGTH: 232
<212> TYPE: PRT
<213> ORGANISM: Canis lupus familiaris

<400> SEQUENCE: 39

```
Met Ser Phe Cys Leu Ile Ser Ser Ser Gln Pro Glu Asn Lys Val Thr
1               5                   10                  15

Glu Leu Asn Glu Pro Leu Ser Asn Glu Glu Arg Asn Leu Leu Ser Val
                20                  25                  30

Ala Tyr Lys Asn Val Val Gly Ala Arg Arg Ser Ser Trp Arg Val Ile
        35                  40                  45

Ser Ser Ile Glu Gln Lys Thr Ser Ala Asp Gly Asn Glu Lys Lys Ile
        50                  55                  60

Glu Met Val Arg Ala Tyr Arg Glu Lys Ile Glu Lys Glu Leu Glu Ala
65                  70                  75                  80

Val Cys Gln Asp Val Leu Ser Leu Leu Asp Asn Tyr Leu Ile Lys Asn
                85                  90                  95

Cys Ser Glu Thr Gln Tyr Glu Ser Lys Val Phe Tyr Leu Lys Met Lys
                100                 105                 110
```

-continued

```
Gly Asp Tyr Tyr Arg Tyr Leu Ala Glu Val Ala Thr Gly Glu Lys Arg
        115                 120                 125

Ala Thr Val Val Glu Ser Ser Glu Lys Ala Tyr Ser Glu Ala His Glu
    130                 135                 140

Ile Ser Lys Glu His Met Gln Pro Thr His Pro Ile Arg Leu Gly Leu
145                 150                 155                 160

Ala Leu Asn Tyr Ser Val Phe Tyr Tyr Glu Ile Gln Asn Ala Pro Glu
                165                 170                 175

Gln Ala Cys His Leu Ala Lys Thr Ala Phe Asp Asp Ala Ile Ala Glu
            180                 185                 190

Leu Asp Thr Leu Asn Glu Asp Ser Tyr Lys Asp Ser Thr Leu Ile Met
        195                 200                 205

Gln Leu Leu Arg Asp Asn Leu Thr Leu Trp Thr Ser Asp Gln Gln Asp
    210                 215                 220

Asp Asp Gly Gly Glu Gly Asn Asn
225                 230

<210> SEQ ID NO 40
<211> LENGTH: 248
<212> TYPE: PRT
<213> ORGANISM: Canis lupus familiaris

<400> SEQUENCE: 40

Met Glu Arg Ala Ser Leu Ile Gln Lys Ala Lys Leu Ala Glu Gln Ala
1               5                   10                  15

Glu Arg Tyr Glu Asp Met Ala Ala Phe Met Lys Ser Ala Val Glu Lys
            20                  25                  30

Gly Glu Glu Leu Ser Cys Glu Glu Arg Asn Leu Leu Ser Val Ala Tyr
        35                  40                  45

Lys Asn Val Val Gly Gly Gln Arg Ala Ala Trp Arg Val Leu Ser Ser
    50                  55                  60

Ile Glu Gln Lys Gly Asn Glu Glu Ser Ser Glu Glu Lys Gly Pro Glu
65                  70                  75                  80

Val Arg Glu Tyr Arg Glu Lys Val Glu Thr Glu Leu Arg Gly Val Cys
                85                  90                  95

Asp Thr Val Leu Gly Leu Leu Asp Ser His Leu Ile Lys Glu Ala Gly
            100                 105                 110

Asp Ala Glu Ser Arg Val Phe Tyr Leu Lys Met Lys Gly Asp Tyr Tyr
        115                 120                 125

Arg Tyr Leu Ala Glu Val Ala Thr Gly Asp Asp Lys Lys Arg Ile Ile
    130                 135                 140

Asp Ser Ala Arg Ser Ala Tyr Gln Glu Ala Met Asp Ile Ser Lys Lys
145                 150                 155                 160

Glu Met Pro Pro Thr Asn Pro Ile Arg Leu Gly Leu Ala Leu Asn Phe
                165                 170                 175

Ser Val Phe His Tyr Glu Ile Ala Asn Ser Pro Glu Glu Ala Ile Ser
            180                 185                 190

Leu Ala Lys Thr Thr Phe Asp Glu Ala Met Ala Asp Leu His Thr Leu
        195                 200                 205

Ser Glu Asp Ser Tyr Lys Asp Ser Thr Leu Ile Met Gln Leu Leu Arg
    210                 215                 220

Asp Asn Leu Thr Leu Trp Thr Ala Asp Asn Ala Gly Glu Glu Gly Gly
225                 230                 235                 240

Glu Ala Pro Glu Glu Pro Gln Ser
```

```
            245

<210> SEQ ID NO 41
<211> LENGTH: 507
<212> TYPE: PRT
<213> ORGANISM: Canis lupus familiaris

<400> SEQUENCE: 41

Met Gly Ala Gly Gly Pro Arg Arg Gly Glu Gly Pro Pro Asp Gly Gly
1               5                   10                  15

Trp Gly Trp Ala Val Leu Gly Ala Cys Phe Val Val Thr Gly Phe Ala
                20                  25                  30

Tyr Gly Phe Pro Lys Ala Val Ser Val Phe Phe Arg Ala Leu Met Arg
            35                  40                  45

Asp Phe Gly Ala Gly Tyr Ser Asp Thr Ala Trp Val Ser Ser Ile Met
        50                  55                  60

Leu Ala Met Leu Tyr Gly Thr Gly Pro Val Ser Ser Ile Leu Val Thr
65                  70                  75                  80

Arg Phe Gly Cys Arg Pro Val Met Leu Val Gly Gly Leu Leu Ala Ser
                85                  90                  95

Ala Gly Met Val Leu Ala Ser Phe Ala Thr Arg Leu Leu Glu Leu Tyr
                100                 105                 110

Leu Thr Ala Gly Val Leu Thr Gly Leu Gly Leu Ala Leu Asn Phe Gln
            115                 120                 125

Pro Ser Leu Ile Met Leu Gly Leu Tyr Phe Glu Arg Arg Arg Pro Leu
        130                 135                 140

Ala Asn Gly Leu Ala Ala Ala Gly Ser Pro Val Phe Leu Ser Thr Leu
145                 150                 155                 160

Ser Pro Leu Gly Gln Gln Leu Leu Glu His Phe Gly Trp Arg Gly Gly
                165                 170                 175

Phe Leu Leu Leu Gly Gly Leu Leu Leu His Cys Cys Ala Cys Gly Ala
                180                 185                 190

Val Met Arg Pro Pro Pro Gly Pro Gly Pro Arg Pro Arg Arg Asp Ser
                195                 200                 205

Ala Asp Asp Pro Pro Ala Asp Ala Asp Ala Glu Ala Gly Ala Gly Ala
            210                 215                 220

Asp Ala Glu Arg Pro Gly Leu Arg Leu Arg Glu Ala Pro Pro Gly Gly
225                 230                 235                 240

Arg Pro Arg Arg Arg Leu Leu Asp Val Ala Val Cys Ala Asp Arg Ala
                245                 250                 255

Phe Ala Val Tyr Thr Val Thr Asn Phe Leu Met Ala Leu Gly Leu Phe
                260                 265                 270

Val Pro Ala Ile Leu Leu Val Trp Ala Lys Asp Ala Gly Val Pro Asp
                275                 280                 285

Ala Asp Ala Ala Phe Leu Leu Ser Val Val Gly Phe Val Asp Ile Val
            290                 295                 300

Ala Arg Pro Ala Cys Gly Ala Leu Ala Gly Leu Ala Arg Leu Arg Pro
305                 310                 315                 320

His Val Ala Tyr Leu Phe Ser Leu Ala Leu Val Ala Asn Gly Leu Thr
                325                 330                 335

Asp Leu Ser Ser Ala Arg Ala Arg Ser Tyr Gly Ala Leu Val Ala Phe
            340                 345                 350

Cys Val Ala Phe Gly Leu Ser Tyr Gly Met Val Gly Ala Leu Gln Phe
            355                 360                 365
```

-continued

```
Glu Val Leu Met Ala Ala Val Gly Ser Leu Arg Phe Pro Ser Ala Leu
    370             375             380

Gly Leu Val Leu Leu Val Glu Ala Val Ala Val Leu Ile Gly Pro Pro
385             390             395             400

Ser Ala Gly Arg Leu Val Asp Ala Leu Lys Asn Tyr Glu Ile Ile Phe
            405             410             415

Tyr Leu Ala Gly Ser Glu Val Ala Leu Ala Gly Ile Phe Met Ala Val
            420             425             430

Ala Thr Lys Cys Cys Leu Arg Arg Ser Arg Asp Thr Pro Pro Gly Gln
            435             440             445

Val Ala Glu Gly Gly Ala Ser Asp Thr Glu Asp Ala Glu Ala Glu Val
    450             455             460

Asp Ser Glu Ala Leu Pro Thr Gly Ala Glu Glu Pro Gly Ser Arg Glu
465             470             475             480

Pro Leu Glu Val Pro Ser Pro Gly Ala Arg Pro Ala Glu Ala Glu Val
            485             490             495

Glu Ala Gly Pro Gly Arg Asp Thr Lys Ser Val
            500             505

<210> SEQ ID NO 42
<211> LENGTH: 498
<212> TYPE: PRT
<213> ORGANISM: Canis lupus familiaris

<400> SEQUENCE: 42

Met Pro Pro Ala Val Gly Gly Pro Val Gly Tyr Thr Pro Pro Asp Gly
1               5               10              15

Gly Trp Gly Trp Ala Val Val Val Gly Ala Phe Ile Ser Ile Gly Phe
                20              25              30

Ser Tyr Ala Phe Pro Lys Ser Ile Thr Val Phe Phe Lys Glu Ile Glu
            35              40              45

Ser Ile Phe Ser Ala Thr Thr Ser Glu Val Ser Trp Ile Ser Ser Ile
    50              55              60

Met Leu Ala Val Met Tyr Gly Gly Pro Ile Ser Ser Ile Leu Val
65              70              75              80

Asn Lys Tyr Gly Ser Arg Pro Ile Met Ile Val Gly Gly Cys Leu Ser
            85              90              95

Gly Cys Gly Leu Ile Ala Ala Ser Phe Cys Asn Thr Val Gln Glu Leu
            100             105             110

Tyr Leu Cys Ile Gly Val Ile Gly Gly Leu Gly Leu Ala Phe Asn Leu
            115             120             125

Asn Pro Ala Leu Thr Met Ile Gly Lys Tyr Phe Tyr Lys Arg Arg Pro
    130             135             140

Leu Ala Asn Gly Leu Ala Met Ala Gly Ser Pro Val Phe Leu Ser Thr
145             150             155             160

Leu Ala Pro Leu Asn Gln Ala Phe Phe Gly Ile Phe Gly Trp Arg Gly
            165             170             175

Ser Phe Leu Ile Leu Gly Gly Leu Leu Leu Asn Cys Cys Val Ala Gly
            180             185             190

Ala Leu Met Arg Pro Ile Gly Pro Pro Pro Thr Ser Ala Gly Lys Asp
            195             200             205

Arg Ser Lys Glu Ser Leu Gln Glu Ala Glu Lys Ser Asp Glu Lys Lys
    210             215             220

Gly Gly Asp Ala Asn Thr Asp Leu Ile Gly Gly Asn Arg Lys Glu Glu
225             230             235             240
```

-continued

```
Lys Gly Ser Val Phe Gln Thr Ile Asn Lys Phe Leu Asp Leu Ser Leu
            245                 250                 255

Phe Thr His Arg Gly Phe Leu Leu Tyr Leu Ser Gly Asn Val Leu Met
            260                 265                 270

Phe Phe Gly Leu Phe Thr Pro Leu Val Phe Leu Ser Asn Tyr Gly Lys
            275                 280                 285

Ser Gln His Tyr Ser Ser Glu Lys Ser Ala Phe Leu Leu Ser Ile Leu
            290                 295                 300

Ala Phe Val Asp Met Val Ala Arg Pro Ser Met Gly Leu Val Ala Asn
305                 310                 315                 320

Thr Lys Trp Ile Arg Pro Arg Val Gln Tyr Phe Phe Ala Ala Ser Ile
                325                 330                 335

Val Ala Asn Gly Val Cys His Leu Leu Ala Pro Leu Ser Ser Ser Tyr
            340                 345                 350

Ile Gly Phe Cys Val Tyr Ala Gly Phe Phe Gly Phe Ala Phe Gly Trp
            355                 360                 365

Leu Ser Ser Val Leu Phe Glu Thr Leu Met Asp Leu Val Gly Pro Gln
            370                 375                 380

Arg Phe Ser Ser Ala Val Gly Leu Val Thr Ile Val Glu Cys Cys Pro
385                 390                 395                 400

Val Leu Leu Gly Pro Pro Leu Leu Gly Arg Leu Asn Asp Ile Tyr Gly
                405                 410                 415

Asp Tyr Lys Tyr Thr Tyr Trp Ala Cys Gly Val Ile Leu Ile Ile Ala
                420                 425                 430

Gly Ile Tyr Leu Phe Ile Gly Met Gly Ile Asn Tyr Gln Leu Val Ala
                435                 440                 445

Lys Glu Gln Lys Ala Glu Lys Gln Gln Lys Lys Glu Ser Lys Glu Glu
            450                 455                 460

Glu Thr Ser Val Asp Ala Ala Glu Lys Pro Lys Glu Tyr Ala Ser Glu
465                 470                 475                 480

Ser Ala Glu Gln Lys Asp Thr Glu Gly Ser Pro Lys Glu Glu Glu Ser
                485                 490                 495

Pro Val
```

```
<210> SEQ ID NO 43
<211> LENGTH: 119
<212> TYPE: PRT
<213> ORGANISM: Canis lupus familiaris

<400> SEQUENCE: 43

Met Lys Leu Val Arg Phe Leu Met Lys Leu Ser His Glu Thr Val Thr
1               5                   10                  15

Ile Glu Leu Lys Asn Gly Thr Gln Val His Gly Thr Ile Thr Gly Val
            20                  25                  30

Asp Val Ser Met Asn Thr His Leu Lys Ala Val Lys Met Thr Leu Lys
            35                  40                  45

Asn Arg Glu Pro Val Gln Leu Glu Thr Leu Ser Ile Arg Gly Asn Asn
        50                  55                  60

Ile Arg Tyr Phe Ile Leu Pro Asp Ser Leu Pro Leu Asp Thr Leu Leu
65                  70                  75                  80

Val Asp Val Glu Pro Lys Val Lys Ser Lys Lys Arg Glu Ala Val Ala
                85                  90                  95

Gly Arg Gly Arg Gly Arg Gly Arg Gly Arg Gly Arg Gly Arg Gly Arg
            100                 105                 110
```

```
Gly Arg Gly Gly Pro Arg Arg
        115

<210> SEQ ID NO 44
<211> LENGTH: 213
<212> TYPE: PRT
<213> ORGANISM: Canis lupus familiaris

<400> SEQUENCE: 44

Met Ala Ala Pro Ala Val Ser Gly Leu Ser Arg Gln Val Arg Cys Phe
1               5                   10                  15

Ser Thr Ser Val Val Arg Pro Phe Ser Lys Leu Val Arg Pro Pro Val
            20                  25                  30

Gln Ile Tyr Gly Ile Glu Gly Arg Tyr Ala Thr Ala Leu Tyr Ser Ala
        35                  40                  45

Ala Ser Lys Gln Asn Lys Leu Glu Gln Val Glu Lys Glu Leu Leu Arg
    50                  55                  60

Val Ala Gln Ile Leu Lys Glu Pro Lys Met Ala Ala Ser Ile Met Asn
65                  70                  75                  80

Pro Tyr Ile Lys Arg Ser Val Lys Val Lys Ser Leu Asn Asp Met Thr
                85                  90                  95

Ala Lys Glu Arg Phe Ser Pro Ile Thr Ser Asn Leu Ile Asn Leu Leu
            100                 105                 110

Ala Glu Asn Gly Arg Leu Asn Asn Thr Pro Gly Val Ile Ser Ala Phe
        115                 120                 125

Ser Thr Met Met Ser Val His Arg Gly Glu Val Pro Cys Thr Val Thr
    130                 135                 140

Thr Ala Ser Pro Leu Asp Glu Ala Thr Leu Thr Glu Leu Lys Thr Val
145                 150                 155                 160

Leu Lys Ser Phe Leu Ser Lys Gly Gln Val Leu Lys Leu Glu Val Lys
                165                 170                 175

Val Asp Pro Ser Ile Met Gly Gly Met Ile Val Arg Ile Gly Glu Lys
            180                 185                 190

Tyr Ala Asp Met Ser Ala Arg Thr Lys Ile Gln Lys Leu Ser Arg Ala
        195                 200                 205

Met Arg Glu Val Phe
    210

<210> SEQ ID NO 45
<211> LENGTH: 518
<212> TYPE: PRT
<213> ORGANISM: Canis lupus familiaris

<400> SEQUENCE: 45

Met Ala Ala Pro Ser Arg Leu Leu Ile Arg Gly Gly Arg Val Val Asn
1               5                   10                  15

Ala Asp Leu Ser Gln Ala Ala Asp Val Leu Val Glu Asp Gly Pro Met
            20                  25                  30

Arg Ala Leu Gly Arg His Leu Leu Pro Pro Gly Gly Ala Ala Gly Leu
        35                  40                  45

Arg Val Leu Asp Ala Ser Gly Lys Leu Val Leu Pro Gly Gly Ile Asp
    50                  55                  60

Thr His Thr His Met Gln Phe Pro Phe Met Gly Ser Arg Ser Val Asp
65                  70                  75                  80

Asp Phe Leu Gln Gly Thr Gln Ala Ala Leu Ala Gly Gly Thr Thr Met
                85                  90                  95
```

-continued

```
Ile Ile Asp Phe Ala Ile Pro Gln Lys Gly Gly Ser Leu Ile Gln Ala
            100                 105                 110

Phe Glu Thr Trp Arg Ser Trp Ala Asp Pro Lys Val Cys Cys Asp Tyr
        115                 120                 125

Ser Leu His Val Ala Val Thr Trp Trp Ser Asp Gln Val Lys Glu Glu
    130                 135                 140

Met Lys Ile Leu Thr Gln Asp Lys Gly Val Asn Ser Phe Lys Met Phe
145                 150                 155                 160

Met Ala Tyr Lys Asp Leu Tyr Met Val Arg Asp Glu Glu Leu Tyr Ala
                165                 170                 175

Ala Phe Ser Gln Cys Lys Glu Ile Gly Ala Ile Ala Leu Val His Ala
            180                 185                 190

Glu Asn Gly Asp Leu Ile Ala Glu Gly Ala Lys Lys Met Leu Ala Leu
            195                 200                 205

Gly Ile Thr Gly Pro Glu Gly His Glu Leu Cys Arg Pro Glu Ala Val
    210                 215                 220

Glu Ala Glu Ala Thr Leu Arg Ala Ile Thr Ile Ala Ser Ala Val Asn
225                 230                 235                 240

Cys Pro Leu Tyr Val Val His Val Met Ser Lys Ser Ala Ala Lys Val
                245                 250                 255

Ile Ala Asp Ala Arg Arg Asp Gly Lys Val Val Tyr Gly Glu Pro Ile
            260                 265                 270

Ala Ala Ser Leu Gly Thr Asp Gly Thr His Tyr Trp His Lys Glu Trp
            275                 280                 285

His His Ala Ala His His Val Met Gly Pro Pro Leu Arg Pro Asp Pro
    290                 295                 300

Ser Thr Pro Asp Phe Leu Met Asn Leu Leu Ala Asn Gly Asp Leu Thr
305                 310                 315                 320

Thr Thr Gly Thr Asp His Cys Thr Phe Asn Thr Cys Gln Lys Ala Leu
                325                 330                 335

Gly Lys Asp Asp Phe Thr Lys Ile Pro Asn Gly Val Asn Gly Val Glu
            340                 345                 350

Asp Arg Met Ser Val Ile Trp Glu Lys Gly Val His Ser Gly Lys Met
        355                 360                 365

Asp Glu Asn Arg Phe Val Ala Val Thr Ser Thr Asn Ala Ala Lys Val
    370                 375                 380

Phe Asn Leu Tyr Pro Arg Lys Gly Arg Ile Ala Val Gly Ser Asp Ala
385                 390                 395                 400

Asp Ile Val Ile Trp Asp Pro Lys Ala Thr Arg Thr Ile Ser Ala Lys
                405                 410                 415

Thr His His Gln Ala Val Asn Phe Asn Ile Phe Glu Gly Met Val Cys
            420                 425                 430

His Gly Val Pro Val Val Thr Ile Ser Arg Gly Lys Val Val Tyr Glu
        435                 440                 445

Ala Gly Val Phe Asn Val Thr Ala Gly Asp Gly Lys Phe Ile Pro Arg
    450                 455                 460

Lys Pro Phe Ala Glu Tyr Ile Tyr Lys Arg Ile Lys Gln Arg Asp Gln
465                 470                 475                 480

Thr Cys Thr Pro Ile Pro Val Glu Arg Lys Pro Tyr Lys Gly Glu Val
                485                 490                 495

Val Thr Val Lys Ser Arg Glu Thr Glu Glu Asp Ser Ala Ala Gly Met
            500                 505                 510
```

-continued

```
Arg Lys Gln Ala Gly Pro
        515

<210> SEQ ID NO 46
<211> LENGTH: 255
<212> TYPE: PRT
<213> ORGANISM: Felis catus

<400> SEQUENCE: 46

Met Asp Asp Arg Glu Asp Leu Val Tyr Gln Ala Lys Leu Ala Glu Gln
1               5                   10                  15

Ala Glu Arg Tyr Asp Glu Met Val Glu Ser Met Lys Lys Val Ala Gly
            20                  25                  30

Met Asp Val Glu Leu Thr Val Glu Glu Arg Asn Leu Leu Ser Val Ala
        35                  40                  45

Tyr Lys Asn Val Ile Gly Ala Arg Arg Ala Ser Trp Arg Ile Ile Ser
    50                  55                  60

Ser Ile Glu Gln Lys Glu Glu Asn Lys Gly Gly Glu Asp Lys Leu Lys
65                  70                  75                  80

Met Ile Arg Glu Tyr Arg Gln Met Val Glu Thr Glu Leu Lys Leu Ile
                85                  90                  95

Cys Cys Asp Ile Leu Asp Val Leu Asp Lys His Leu Ile Pro Ala Ala
            100                 105                 110

Asn Thr Gly Glu Ser Lys Val Phe Tyr Tyr Lys Met Lys Gly Asp Tyr
        115                 120                 125

His Arg Tyr Leu Ala Glu Phe Ala Thr Gly Asn Asp Arg Lys Glu Ala
    130                 135                 140

Ala Glu Asn Ser Leu Val Ala Tyr Lys Ala Ala Ser Asp Ile Ala Met
145                 150                 155                 160

Thr Glu Leu Pro Pro Thr His Pro Ile Arg Leu Gly Leu Ala Leu Asn
                165                 170                 175

Phe Ser Val Phe Tyr Tyr Glu Ile Leu Asn Ser Pro Asp Arg Ala Cys
            180                 185                 190

Arg Leu Ala Lys Ala Ala Phe Asp Asp Ala Ile Ala Glu Leu Asp Thr
        195                 200                 205

Leu Ser Glu Glu Ser Tyr Lys Asp Ser Thr Leu Ile Met Gln Leu Leu
    210                 215                 220

Arg Asp Asn Leu Thr Leu Trp Thr Ser Asp Met Gln Gly Asp Gly Glu
225                 230                 235                 240

Glu Gln Asn Lys Glu Ala Leu Gln Asp Val Glu Asp Glu Asn Gln
                245                 250                 255

<210> SEQ ID NO 47
<211> LENGTH: 255
<212> TYPE: PRT
<213> ORGANISM: Felis catus

<400> SEQUENCE: 47

Met Leu Gln Asp Val Leu Phe Ser Ser Cys Cys Ser Leu Leu Val Gln
1               5                   10                  15

Val Ala Phe His Asp Glu Met Val Glu Ser Met Lys Lys Val Ala Gly
            20                  25                  30

Met Asp Val Glu Leu Thr Val Glu Glu Arg Asn Leu Leu Ser Val Ala
        35                  40                  45

Tyr Lys Asn Val Ile Gly Ala Arg Arg Ala Ser Trp Arg Ile Ile Ser
    50                  55                  60
```

-continued

```
Ser Ile Glu Gln Lys Glu Glu Asn Lys Gly Gly Glu Asp Lys Leu Lys
65              70              75              80

Met Ile Arg Glu Tyr Arg Gln Met Val Glu Thr Glu Leu Lys Leu Ile
                85              90              95

Cys Cys Asp Ile Leu Asp Val Leu Asp Lys His Leu Ile Pro Ala Ala
            100             105             110

Asn Thr Gly Glu Ser Lys Val Phe Tyr Tyr Lys Met Lys Gly Asp Tyr
        115             120             125

His Arg Tyr Leu Ala Glu Phe Ala Thr Gly Asn Asp Arg Lys Glu Ala
        130             135             140

Ala Glu Asn Ser Leu Val Ala Tyr Lys Ala Ala Ser Asp Ile Ala Met
145             150             155             160

Thr Glu Leu Pro Pro Thr His Pro Ile Arg Leu Gly Leu Ala Leu Asn
                165             170             175

Phe Ser Val Phe Tyr Tyr Glu Ile Leu Asn Ser Pro Asp Arg Ala Cys
            180             185             190

Arg Leu Ala Lys Ala Ala Phe Asp Asp Ala Ile Ala Glu Leu Asp Thr
        195             200             205

Leu Ser Glu Glu Ser Tyr Lys Asp Ser Thr Leu Ile Met Gln Leu Leu
        210             215             220

Arg Asp Asn Leu Thr Leu Trp Thr Ser Asp Met Gln Gly Asp Gly Glu
225             230             235             240

Glu Gln Asn Lys Glu Ala Leu Gln Asp Val Glu Asp Glu Asn Gln
                245             250             255
```

<210> SEQ ID NO 48
<211> LENGTH: 240
<212> TYPE: PRT
<213> ORGANISM: Felis catus

<400> SEQUENCE: 48

```
Met Asp Asp Arg Glu Asp Leu Val Tyr Gln Ala Lys Leu Ala Glu Gln
1               5               10              15

Ala Glu Arg Tyr Asp Glu Met Val Glu Ser Met Lys Lys Val Ala Gly
            20              25              30

Met Asp Val Glu Leu Thr Val Glu Glu Arg Asn Leu Leu Ser Val Ala
        35              40              45

Tyr Lys Asn Val Ile Gly Ala Arg Arg Ala Ser Trp Arg Ile Ile Ser
    50              55              60

Ser Ile Glu Gln Lys Glu Glu Asn Lys Gly Gly Glu Asp Lys Leu Lys
65              70              75              80

Met Ile Arg Glu Tyr Arg Gln Met Val Glu Thr Glu Leu Lys Leu Ile
                85              90              95

Cys Cys Asp Ile Leu Asp Val Leu Asp Lys His Leu Ile Pro Ala Ala
            100             105             110

Asn Thr Gly Glu Ser Lys Val Phe Tyr Tyr Lys Met Lys Gly Asp Tyr
        115             120             125

His Arg Tyr Leu Ala Glu Phe Ala Thr Gly Asn Asp Arg Lys Glu Ala
        130             135             140

Ala Glu Asn Ser Leu Val Ala Tyr Lys Ala Ala Ser Asp Ile Ala Met
145             150             155             160

Thr Glu Leu Pro Pro Thr His Pro Ile Arg Leu Gly Leu Ala Leu Asn
                165             170             175

Phe Ser Val Phe Tyr Tyr Glu Ile Leu Asn Ser Pro Asp Arg Ala Cys
            180             185             190
```

-continued

```
Arg Leu Ala Lys Ala Ala Phe Asp Asp Ala Ile Ala Glu Leu Asp Thr
        195                 200                 205

Leu Ser Glu Glu Ser Tyr Lys Asp Ser Thr Leu Ile Met Gln Leu Leu
    210                 215                 220

Arg Asp Asn Leu Thr Leu Trp Thr Ser Asp Met Gln Gly Asp Asp Ser
225                 230                 235                 240

<210> SEQ ID NO 49
<211> LENGTH: 245
<212> TYPE: PRT
<213> ORGANISM: Felis catus

<400> SEQUENCE: 49

Met Glu Lys Thr Glu Leu Ile Gln Lys Ala Lys Leu Ala Glu Gln Ala
1               5                   10                  15

Glu Arg Tyr Asp Asp Met Ala Thr Cys Met Lys Ala Val Thr Glu Gln
            20                  25                  30

Gly Ala Glu Leu Ser Asn Glu Glu Arg Asn Leu Leu Ser Val Ala Tyr
        35                  40                  45

Lys Asn Val Val Gly Gly Arg Arg Ser Ala Trp Arg Val Ile Ser Ser
    50                  55                  60

Ile Glu Gln Lys Thr Asp Thr Ser Asp Lys Lys Leu Gln Leu Ile Lys
65                  70                  75                  80

Asp Tyr Arg Glu Lys Val Glu Ser Glu Leu Arg Ser Ile Cys Thr Thr
                85                  90                  95

Val Leu Glu Leu Leu Asp Lys Tyr Leu Ile Ala Asn Ala Thr Asn Pro
            100                 105                 110

Glu Ser Lys Val Phe Tyr Leu Lys Met Lys Gly Asp Tyr Phe Arg Tyr
        115                 120                 125

Leu Ala Glu Val Ala Cys Gly Asp Asp Arg Lys Gln Thr Ile Asp Asn
    130                 135                 140

Ser Gln Gly Ala Tyr Gln Glu Ala Phe Asp Ile Ser Lys Lys Glu Met
145                 150                 155                 160

Gln Pro Thr His Pro Ile Arg Leu Gly Leu Ala Leu Asn Phe Ser Val
                165                 170                 175

Phe Tyr Tyr Glu Ile Leu Asn Asn Pro Glu Leu Ala Cys Thr Leu Ala
            180                 185                 190

Lys Thr Ala Phe Asp Glu Ala Ile Ala Glu Leu Asp Thr Leu Asn Glu
        195                 200                 205

Asp Ser Tyr Lys Asp Ser Thr Leu Ile Met Gln Leu Leu Arg Asp Asn
    210                 215                 220

Leu Thr Leu Trp Thr Ser Asp Ser Ala Gly Glu Glu Cys Asp Ala Ala
225                 230                 235                 240

Glu Gly Ala Glu Asn
                245

<210> SEQ ID NO 50
<211> LENGTH: 245
<212> TYPE: PRT
<213> ORGANISM: Felis catus

<400> SEQUENCE: 50

Met Asp Lys Asn Glu Leu Val Gln Lys Ala Lys Leu Ala Glu Gln Ala
1               5                   10                  15

Glu Arg Tyr Asp Asp Met Ala Ala Cys Met Lys Ser Val Thr Glu Gln
            20                  25                  30
```

-continued

```
Gly Ala Glu Leu Ser Asn Glu Glu Arg Asn Leu Leu Ser Val Ala Tyr
        35                  40                  45

Lys Asn Val Val Gly Ala Arg Arg Ser Ser Trp Arg Val Val Ser Ser
    50                  55                  60

Ile Glu Gln Lys Thr Glu Gly Ala Glu Lys Lys Gln Gln Met Ala Arg
65                  70                  75                  80

Glu Tyr Arg Glu Lys Ile Glu Thr Glu Leu Arg Asp Ile Cys Asn Asp
                85                  90                  95

Val Leu Ser Leu Leu Glu Lys Phe Leu Ile Pro Asn Ala Ser Gln Ala
                100                 105                 110

Glu Ser Lys Val Phe Tyr Leu Lys Met Lys Gly Asp Tyr Tyr Arg Tyr
                115                 120                 125

Leu Ala Glu Val Ala Ala Gly Asp Asp Lys Lys Gly Ile Val Asp Gln
        130                 135                 140

Ser Gln Gln Ala Tyr Gln Glu Ala Phe Glu Ile Ser Lys Lys Glu Met
145                 150                 155                 160

Gln Pro Thr His Pro Ile Arg Leu Gly Leu Ala Leu Asn Phe Ser Val
                165                 170                 175

Phe Tyr Tyr Glu Ile Leu Asn Ser Pro Glu Lys Ala Cys Ser Leu Ala
                180                 185                 190

Lys Thr Ala Phe Asp Glu Ala Ile Ala Glu Leu Asp Thr Leu Ser Glu
        195                 200                 205

Glu Ser Tyr Lys Asp Ser Thr Leu Ile Met Gln Leu Leu Arg Asp Asn
        210                 215                 220

Leu Thr Leu Trp Thr Ser Asp Thr Gln Gly Asp Glu Ala Glu Ala Gly
225                 230                 235                 240

Glu Gly Gly Glu Asn
                245

<210> SEQ ID NO 51
<211> LENGTH: 244
<212> TYPE: PRT
<213> ORGANISM: Felis catus

<400> SEQUENCE: 51

Met Asp Lys Ser Glu Leu Val Gln Lys Ala Lys Leu Ala Glu Gln Ala
1                   5                   10                  15

Glu Arg Tyr Asp Asp Met Ala Ala Ala Met Lys Ala Val Thr Glu Gln
                20                  25                  30

Gly His Glu Leu Ser Asn Glu Glu Arg Asn Leu Leu Ser Val Ala Tyr
        35                  40                  45

Lys Asn Val Val Gly Ala Arg Arg Ser Ser Trp Arg Val Ile Ser Ser
    50                  55                  60

Ile Glu Gln Lys Thr Glu Arg Asn Glu Lys Lys Gln Gln Met Gly Lys
65                  70                  75                  80

Glu Tyr Arg Glu Lys Ile Glu Ala Glu Leu Gln Asp Ile Cys Asn Asp
                85                  90                  95

Val Leu Glu Leu Leu Asp Lys Tyr Leu Ile Pro Asn Ala Thr Gln Pro
                100                 105                 110

Glu Ser Lys Val Phe Tyr Leu Lys Met Lys Gly Asp Tyr Phe Arg Tyr
                115                 120                 125

Leu Ser Glu Val Ala Ser Gly Asp Asn Lys Gln Thr Thr Val Ser Asn
        130                 135                 140

Ser Gln Gln Ala Tyr Gln Glu Ala Phe Glu Ile Ser Lys Lys Glu Met
```

```
145             150             155             160

Gln Pro Thr His Pro Ile Arg Leu Gly Leu Ala Leu Asn Phe Ser Val
                165             170             175

Phe Tyr Tyr Glu Ile Leu Asn Ser Pro Glu Lys Ala Cys Ser Leu Ala
            180             185             190

Lys Thr Ala Phe Asp Glu Ala Ile Ala Glu Leu Asp Thr Leu Asn Glu
        195             200             205

Glu Ser Tyr Lys Asp Ser Thr Leu Ile Met Gln Leu Leu Arg Asp Asn
    210             215             220

Leu Thr Leu Trp Thr Ser Glu Asn Gln Gly Asp Glu Gly Asp Ala Gly
225             230             235             240

Glu Gly Glu Asn

<210> SEQ ID NO 52
<211> LENGTH: 246
<212> TYPE: PRT
<213> ORGANISM: Felis catus

<400> SEQUENCE: 52

Met Gly Asp Arg Glu Gln Leu Leu Gln Arg Ala Arg Leu Ala Glu Gln
1               5               10              15

Ala Glu Arg Tyr Asp Asp Met Ala Ser Ala Met Lys Ala Val Thr Glu
            20              25              30

Leu Asn Glu Pro Leu Ser Asn Glu Asp Arg Asn Leu Leu Ser Val Ala
        35              40              45

Tyr Lys Asn Val Val Gly Ala Arg Arg Ser Ser Trp Arg Val Ile Ser
    50              55              60

Ser Ile Glu Gln Lys Thr Met Ala Asp Gly Asn Glu Lys Lys Leu Glu
65              70              75              80

Lys Val Lys Ala Tyr Arg Glu Lys Ile Glu Lys Glu Leu Glu Thr Val
            85              90              95

Cys Asn Asp Val Leu Ala Leu Leu Asp Lys Phe Leu Ile Lys Asn Cys
            100             105             110

Asn Asp Phe Gln Tyr Glu Ser Lys Val Phe Tyr Leu Lys Met Lys Gly
        115             120             125

Asp Tyr Tyr Arg Tyr Leu Ala Glu Val Ala Ser Gly Glu Lys Lys Asn
    130             135             140

Ser Val Val Glu Ala Ser Glu Ala Ala Tyr Lys Glu Ala Phe Glu Ile
145             150             155             160

Ser Lys Glu His Met Gln Pro Thr His Pro Ile Arg Leu Gly Leu Ala
            165             170             175

Leu Asn Phe Ser Val Phe Tyr Tyr Glu Ile Gln Asn Ala Pro Glu Gln
            180             185             190

Ala Cys Leu Leu Ala Lys Gln Ala Phe Asp Asp Ala Ile Ala Glu Leu
        195             200             205

Asp Thr Leu Asn Glu Asp Ser Tyr Lys Asp Ser Thr Leu Ile Met Gln
    210             215             220

Leu Leu Arg Asp Asn Leu Thr Leu Trp Thr Ser Asp Gln Gln Asp Glu
225             230             235             240

Glu Ala Gly Glu Gly Asn
                245

<210> SEQ ID NO 53
<211> LENGTH: 247
<212> TYPE: PRT
```

```
<213> ORGANISM: Felis catus

<400> SEQUENCE: 53

Met Val Asp Arg Glu Gln Leu Val Gln Lys Ala Arg Leu Ala Glu Gln
1               5                   10                  15

Ala Glu Arg Tyr Asp Asp Met Ala Ala Ala Met Lys Asn Val Thr Glu
                20                  25                  30

Leu Asn Glu Pro Leu Ser Asn Glu Glu Arg Asn Leu Leu Ser Val Ala
            35                  40                  45

Tyr Lys Asn Val Val Gly Ala Arg Arg Ser Ser Trp Arg Val Ile Ser
        50                  55                  60

Ser Ile Glu Gln Lys Thr Ser Ala Asp Gly Asn Glu Lys Lys Ile Glu
65                  70                  75                  80

Met Val Arg Ala Tyr Arg Glu Lys Ile Glu Lys Glu Leu Glu Ala Val
                85                  90                  95

Cys Gln Asp Val Leu Ser Leu Leu Asp Asn Tyr Leu Ile Lys Asn Cys
            100                 105                 110

Ser Glu Thr Gln Tyr Glu Ser Lys Val Phe Tyr Leu Lys Met Lys Gly
        115                 120                 125

Asp Tyr Tyr Arg Tyr Leu Ala Glu Val Ala Thr Gly Glu Lys Arg Ala
    130                 135                 140

Thr Val Val Glu Ser Ser Glu Lys Ala Tyr Ser Glu Ala His Glu Ile
145                 150                 155                 160

Ser Lys Glu His Met Gln Pro Thr His Pro Ile Arg Leu Gly Leu Ala
                165                 170                 175

Leu Asn Tyr Ser Val Phe Tyr Tyr Glu Ile Gln Asn Ala Pro Glu Gln
                180                 185                 190

Ala Cys His Leu Ala Lys Thr Ala Phe Asp Asp Ala Ile Ala Glu Leu
            195                 200                 205

Asp Thr Leu Asn Glu Asp Ser Tyr Lys Asp Ser Thr Leu Ile Met Gln
        210                 215                 220

Leu Leu Arg Asp Asn Leu Thr Leu Trp Thr Ser Asp Gln Gln Asp Asp
225                 230                 235                 240

Asp Gly Gly Glu Gly Asn Asn
                245

<210> SEQ ID NO 54
<211> LENGTH: 248
<212> TYPE: PRT
<213> ORGANISM: Felis catus

<400> SEQUENCE: 54

Met Glu Arg Ala Ser Leu Ile Gln Lys Ala Lys Leu Ala Glu Gln Ala
1               5                   10                  15

Glu Arg Tyr Glu Asp Met Ala Ala Phe Met Lys Ser Ala Val Glu Lys
                20                  25                  30

Gly Glu Glu Leu Ser Cys Glu Glu Arg Asn Leu Leu Ser Val Ala Tyr
            35                  40                  45

Lys Asn Val Val Gly Gly Gln Arg Ala Ala Trp Arg Val Leu Ser Ser
        50                  55                  60

Ile Glu Gln Lys Gly Asn Glu Glu Ser Ser Glu Lys Gly Pro Glu
65                  70                  75                  80

Val Arg Glu Tyr Arg Glu Lys Val Glu Thr Glu Leu Arg Gly Val Cys
                85                  90                  95

Asp Thr Val Leu Gly Leu Leu Asp Thr His Leu Ile Lys Glu Ala Gly
```

-continued

```
                    100                 105                 110

Asp Ala Glu Ser Arg Val Phe Tyr Leu Lys Met Lys Gly Asp Tyr Tyr
            115                 120                 125

Arg Tyr Leu Ala Glu Val Ala Thr Gly Asp Asp Lys Lys Arg Ile Ile
        130                 135                 140

Asp Ser Ala Arg Ser Ala Tyr Gln Glu Ala Met Asp Ile Ser Lys Lys
145                 150                 155                 160

Glu Met Pro Pro Thr Asn Pro Ile Arg Leu Gly Leu Ala Leu Asn Phe
                165                 170                 175

Ser Val Phe His Tyr Glu Ile Ala Asn Ser Pro Glu Glu Ala Ile Ser
            180                 185                 190

Leu Ala Lys Thr Thr Phe Asp Glu Ala Met Ala Asp Leu His Thr Leu
        195                 200                 205

Ser Glu Asp Ser Tyr Lys Asp Ser Thr Leu Ile Met Gln Leu Leu Arg
    210                 215                 220

Asp Asn Leu Thr Leu Trp Thr Ala Asp Asn Ala Gly Glu Glu Gly Gly
225                 230                 235                 240

Glu Ala Pro Glu Glu Pro Gln Ser
                245
```

<210> SEQ ID NO 55
<211> LENGTH: 500
<212> TYPE: PRT
<213> ORGANISM: Felis catus

<400> SEQUENCE: 55

```
Met Gly Ala Gly Gly Pro Arg Arg Gly Ala Gly Pro Pro Asp Gly Gly
1               5                   10                  15

Trp Gly Trp Ala Val Leu Gly Ala Cys Phe Val Ile Thr Gly Phe Ala
            20                  25                  30

Tyr Gly Phe Pro Lys Ala Val Ser Val Phe Phe Arg Ala Leu Met Arg
        35                  40                  45

Asp Phe Gly Ala Gly Tyr Ser Asp Thr Ala Trp Val Ser Ser Ile Met
    50                  55                  60

Leu Ala Met Leu Tyr Gly Thr Gly Pro Val Ser Ser Ile Leu Val Thr
65                  70                  75                  80

Arg Phe Gly Cys Arg Pro Val Met Leu Val Gly Gly Leu Leu Ala Ser
            85                  90                  95

Ala Gly Met Val Leu Ala Ser Phe Ala Thr Arg Leu Leu Glu Leu Tyr
            100                 105                 110

Leu Thr Ala Gly Val Leu Thr Gly Leu Gly Leu Ala Leu Asn Phe Gln
        115                 120                 125

Pro Ser Leu Ile Met Leu Gly Leu Tyr Phe Glu Arg Arg Arg Pro Leu
        130                 135                 140

Ala Asn Gly Leu Ala Ala Ala Gly Ser Pro Val Phe Leu Ser Ala Leu
145                 150                 155                 160

Ser Pro Leu Gly Gln Gln Leu Leu Glu His Phe Gly Trp Arg Gly Gly
                165                 170                 175

Phe Leu Leu Leu Gly Gly Leu Leu Leu His Cys Cys Ala Cys Gly Ala
            180                 185                 190

Val Met Arg Pro Pro Pro Gly Pro Gly Pro Arg Pro Arg Gly Asp Ser
        195                 200                 205

Ala Glu Asp Ala Pro Gly Glu Ala Glu Ala Asp Arg Ala Gly Leu Arg
    210                 215                 220
```

-continued

Leu Arg Glu Ala Pro Pro Gly Gly Arg Thr Arg Arg Leu Leu Asp
225                 230                 235                 240

Val Ala Val Cys Ala Asp Arg Ala Phe Gly Val Tyr Ala Ile Thr Lys
                245                 250                 255

Phe Leu Met Ala Leu Gly Leu Phe Val Pro Ala Ile Leu Leu Val Asn
                260                 265                 270

Tyr Ala Lys Asp Ala Gly Val Pro Asp Ala Asp Ala Ala Phe Leu Leu
                275                 280                 285

Ser Ile Val Gly Phe Val Asp Ile Val Ala Arg Pro Ala Cys Gly Ala
                290                 295                 300

Leu Ala Gly Leu Ala Arg Leu Arg Pro His Val Ala Tyr Leu Phe Ser
305                 310                 315                 320

Leu Ala Leu Met Ala Asn Gly Leu Thr Asp Leu Ser Ser Ala Arg Ala
                325                 330                 335

Arg Ser Tyr Gly Ala Leu Val Ala Phe Cys Val Ala Phe Gly Leu Ser
                340                 345                 350

Tyr Gly Met Val Gly Ala Leu Gln Phe Glu Val Leu Met Ala Ala Val
                355                 360                 365

Gly Ser His Arg Phe Pro Ser Ala Leu Gly Leu Val Leu Leu Val Glu
        370                 375                 380

Ala Val Ala Val Leu Ile Gly Pro Pro Ser Ala Gly Arg Leu Val Asp
385                 390                 395                 400

Ala Leu Lys Asn Tyr Glu Ile Ile Phe Tyr Leu Ala Gly Ser Glu Val
                405                 410                 415

Ala Leu Ala Gly Ile Phe Met Ala Val Ala Thr Lys Cys Cys Leu Arg
                420                 425                 430

Arg Ser Lys Asp Thr Pro Pro Ser Gln Gly Ala Gln Gly Gly Ala Ser
                435                 440                 445

Asp Thr Glu Asp Ala Glu Ala Gln Glu Asp Ala Glu Ala Leu Pro Ala
        450                 455                 460

Gly Ala Glu Glu Pro Gly Ser Leu Gln Ala Leu Glu Ala Pro Ser Pro
465                 470                 475                 480

Gly Ala Gly Pro Gly Glu Pro Lys Ala Glu Ala Glu Ala Gly Val Asp
                485                 490                 495

Pro Glu Ser Val
        500

<210> SEQ ID NO 56
<211> LENGTH: 460
<212> TYPE: PRT
<213> ORGANISM: Felis catus

<400> SEQUENCE: 56

Met Gly Gly Ala Val Val Asp Glu Gly Pro Thr Gly Ile Lys Ala Pro
1               5                   10                  15

Asp Gly Gly Trp Gly Trp Ala Val Leu Phe Gly Cys Phe Val Ile Thr
                20                  25                  30

Gly Phe Ser Tyr Ala Phe Pro Lys Ala Val Ser Val Phe Phe Lys Glu
        35                  40                  45

Leu Met Arg Glu Phe Gly Ile Gly Tyr Ser Asp Thr Ala Trp Ile Ser
        50                  55                  60

Ser Ile Leu Leu Ala Met Leu Tyr Gly Thr Gly Pro Leu Cys Ser Val
65                  70                  75                  80

Cys Val Asn Arg Phe Gly Cys Arg Pro Val Met Leu Ala Gly Gly Leu
                85                  90                  95

-continued

```
Leu Ala Ser Leu Gly Met Val Ala Ala Ser Phe Cys Gly Ser Ile Ile
            100                 105                 110

Gln Leu Tyr Leu Thr Thr Gly Val Ile Thr Gly Leu Gly Leu Ala Leu
            115                 120                 125

Asn Phe Gln Pro Ser Leu Ile Met Leu Asn Arg Tyr Phe Asn Lys Arg
            130                 135                 140

Arg Pro Met Ala Asn Gly Leu Ala Ala Ala Gly Ser Pro Val Phe Leu
145                 150                 155                 160

Cys Ala Leu Ser Pro Leu Gly Gln Leu Leu Gln Asp His Tyr Gly Trp
                165                 170                 175

Arg Gly Gly Phe Leu Ile Leu Gly Gly Leu Leu Leu Asn Cys Cys Val
                180                 185                 190

Cys Ala Ala Leu Met Arg Pro Leu Glu Ala Ser Arg Pro Gly Ser Gly
                195                 200                 205

Pro Gly Pro Gln Arg Pro Ala Arg Arg Leu Leu Asp Leu Ser Val Phe
            210                 215                 220

Arg Asp Arg Gly Phe Val Ile Tyr Ala Ala Ala Ala Ser Ile Met Val
225                 230                 235                 240

Leu Gly Leu Phe Val Pro Pro Val Phe Val Val Ser Tyr Ala Lys Asp
                245                 250                 255

Leu Gly Val Pro Asp Thr Gln Ala Ala Phe Leu Leu Thr Val Leu Gly
                260                 265                 270

Phe Ile Asp Ile Phe Ala Arg Pro Ala Ala Gly Phe Ile Thr Gly Leu
            275                 280                 285

Lys Lys Val Arg Pro Tyr Ser Val Tyr Leu Phe Ser Phe Ser Met Phe
            290                 295                 300

Phe Asn Gly Phe Thr Asp Leu Thr Gly Ser Thr Ala Ser Asp Tyr Gly
305                 310                 315                 320

Gly Leu Val Val Phe Cys Ile Phe Phe Gly Ile Ser Tyr Gly Met Val
                325                 330                 335

Gly Ala Leu Gln Phe Glu Val Leu Met Ala Ile Val Gly Thr Gln Lys
            340                 345                 350

Phe Ser Ser Ala Ile Gly Leu Val Leu Leu Leu Glu Ala Ile Ala Val
            355                 360                 365

Leu Ile Gly Pro Pro Ser Gly Gly Lys Leu Leu Asp Ala Thr His Val
            370                 375                 380

Tyr Gln Tyr Val Phe Leu Leu Ala Gly Ala Glu Val Val Ala Ser Ser
385                 390                 395                 400

Leu Val Leu Val Leu Gly Asn Phe Phe Cys Ile Lys Lys Arg Pro Glu
                405                 410                 415

Ala Ala Val Glu Glu Gly Glu Arg His Lys Pro Pro Ala Asp Val Arg
                420                 425                 430

Val Asp Ser Arg Glu Val Glu His Phe Leu Lys Ala Glu Pro Glu Lys
            435                 440                 445

Asn Gly Glu Val Val His Thr Pro Glu Thr Ser Val
            450                 455                 460
```

<210> SEQ ID NO 57
<211> LENGTH: 480
<212> TYPE: PRT
<213> ORGANISM: Felis catus

<400> SEQUENCE: 57

```
Met Gly Gly Ala Val Val Asp Glu Gly Pro Thr Gly Ile Lys Ala Pro
```

-continued

```
1               5               10              15

Asp Gly Gly Trp Gly Trp Ala Val Leu Phe Gly Cys Phe Val Ile Thr
             20              25              30

Gly Phe Ser Tyr Ala Phe Pro Lys Ala Val Ser Val Phe Phe Lys Glu
             35              40              45

Leu Met Arg Glu Phe Gly Ile Gly Tyr Ser Asp Thr Ala Trp Ile Ser
   50              55              60

Ser Ile Leu Leu Ala Met Leu Tyr Gly Thr Gly Pro Leu Cys Ser Val
65              70              75              80

Cys Val Asn Arg Phe Gly Cys Arg Pro Val Met Leu Ala Gly Gly Leu
             85              90              95

Leu Ala Ser Leu Gly Met Val Ala Ala Ser Phe Cys Gly Ser Ile Ile
             100             105             110

Gln Leu Tyr Leu Thr Thr Gly Val Ile Thr Gly Glu Trp Gly Pro Ala
             115             120             125

Gly Ser Gly Ala Gly His Gly Thr Leu Thr Pro Gln Trp Pro Gly Leu
             130             135             140

Gly Leu Ala Leu Asn Phe Gln Pro Ser Leu Ile Met Leu Asn Arg Tyr
145             150             155             160

Phe Asn Lys Arg Arg Pro Met Ala Asn Gly Leu Ala Ala Ala Gly Ser
             165             170             175

Pro Val Phe Leu Cys Ala Leu Ser Pro Leu Gly Gln Leu Leu Gln Asp
             180             185             190

His Tyr Gly Trp Arg Gly Gly Phe Leu Ile Leu Gly Gly Leu Leu Leu
             195             200             205

Asn Cys Cys Val Cys Ala Ala Leu Met Arg Pro Leu Glu Ala Ser Arg
   210             215             220

Pro Gly Ser Gly Pro Gly Pro Gln Arg Pro Ala Arg Arg Leu Leu Asp
225             230             235             240

Leu Ser Val Phe Arg Asp Arg Gly Phe Val Ile Tyr Ala Ala Ala Ala
             245             250             255

Ser Ile Met Val Leu Gly Leu Phe Val Pro Pro Val Phe Val Val Ser
             260             265             270

Tyr Ala Lys Asp Leu Gly Val Pro Asp Thr Gln Ala Ala Phe Leu Leu
   275             280             285

Thr Val Leu Gly Phe Ile Asp Ile Phe Ala Arg Pro Ala Ala Gly Phe
   290             295             300

Ile Thr Gly Leu Lys Lys Val Arg Pro Tyr Ser Val Tyr Leu Phe Ser
305             310             315             320

Phe Ser Met Phe Phe Asn Gly Phe Thr Asp Leu Thr Gly Ser Thr Ala
             325             330             335

Ser Asp Tyr Gly Gly Leu Val Val Phe Cys Ile Phe Phe Gly Ile Ser
             340             345             350

Tyr Gly Met Val Gly Ala Leu Gln Phe Glu Val Leu Met Ala Ile Val
   355             360             365

Gly Thr Gln Lys Phe Ser Ser Ala Ile Gly Leu Val Leu Leu Leu Glu
   370             375             380

Ala Ile Ala Val Leu Ile Gly Pro Pro Ser Gly Gly Lys Leu Leu Asp
385             390             395             400

Ala Thr His Val Tyr Gln Tyr Val Phe Leu Leu Ala Gly Ala Glu Val
             405             410             415

Val Ala Ser Ser Leu Val Leu Val Leu Gly Asn Phe Phe Cys Ile Lys
             420             425             430
```

-continued

```
Lys Arg Pro Glu Ala Ala Val Glu Glu Gly Glu Arg His Lys Pro Pro
        435                 440                 445

Ala Asp Val Arg Val Asp Ser Arg Glu Val Glu His Phe Leu Lys Ala
    450                 455                 460

Glu Pro Glu Lys Asn Gly Glu Val Val His Thr Pro Glu Thr Ser Val
465                 470                 475                 480

<210> SEQ ID NO 58
<211> LENGTH: 327
<212> TYPE: PRT
<213> ORGANISM: Felis catus

<400> SEQUENCE: 58

Met Gln Glu Pro Gly Ser Glu Glu Glu Phe His Ser Leu Gly Phe Tyr
1               5                   10                  15

Arg Met Thr Thr Arg Asp Leu Thr Met Ala Met Ile Phe Phe Leu Gln
                20                  25                  30

Thr Thr Val Gly Ile Leu Gly Asn Phe Ser Val Phe Tyr Tyr Tyr Leu
        35                  40                  45

Phe Leu Tyr Leu Thr Gly Tyr Lys Leu Arg Cys Thr Asp Leu Ile Val
    50                  55                  60

Lys Tyr Leu Thr Val Ala Asn Leu Leu Val Ile Phe Ser Lys Gly Ile
65                  70                  75                  80

Pro Gln Thr Met Ala Ser Phe Gly Leu Pro His Phe Leu Asp Asp Phe
                85                  90                  95

Gly Cys Lys Leu Val Phe Phe Val His Arg Val Gly Arg Asp Val Ala
                100                 105                 110

Ile Gly Thr Thr Cys Leu Leu Thr Val Phe Gln Val Ile Met Ile Ser
            115                 120                 125

Pro Gly Asp Ser Arg Trp Ala Gln Leu Lys Ile Lys Ala Pro Lys Tyr
    130                 135                 140

Met Gly Thr Ser Asn Ile Phe Cys Trp Val Leu Asn Ile Val Arg Ser
145                 150                 155                 160

Ile Val Val Pro Phe His Leu Thr Asp Lys Arg Asn Asn Ile Asn Val
                165                 170                 175

Thr Lys Lys Ile Asp Gln Asp Tyr Cys Tyr Ala Ile Ser Ser Asp Lys
            180                 185                 190

Ile Ala Gln Ser Phe Tyr Val Pro Leu Leu Leu Ser His Asp Gly Phe
        195                 200                 205

Cys Leu Gly Leu Met Leu Trp Ala Ser Gly Ser Met Val Phe Ile Leu
    210                 215                 220

His Ser His Lys Gln Arg Val Gln Tyr Ile Arg Arg Asn Asn Leu Ser
225                 230                 235                 240

Pro Arg Ser Ser Pro Glu Ser Arg Ala Thr Arg Ser Ile Leu Val Leu
                245                 250                 255

Ala Phe Phe Phe Leu Ser Leu Trp Met Leu Ser Ser Ile Phe His Met
        260                 265                 270

Cys Phe Ser Val Phe Asn Asn Pro Ser Leu Trp Leu Arg Asn Thr Ser
        275                 280                 285

Thr Ile Leu Thr Met Cys Phe Pro Thr Leu Ser Pro Tyr Ile Leu Met
    290                 295                 300

Arg His Asp Pro Arg Val Ser Thr Leu Tyr Ser Ala Trp Ile Arg Lys
305                 310                 315                 320

Gln Asn Arg Leu Asn Leu Ser
```

-continued

```
                    325

<210> SEQ ID NO 59
<211> LENGTH: 241
<212> TYPE: PRT
<213> ORGANISM: Felis catus

<400> SEQUENCE: 59

Met Phe Pro Leu Leu Ser Gly Ala Gly Leu Val Val Leu Asn Leu Val
1               5                   10                  15

Thr Ser Ala Arg Ser Leu Lys Thr Glu Pro Phe Ile Gly Ser Gly Asp
            20                  25                  30

Gln Pro Leu Phe His Gly Ala Asp Arg Ser Asp Phe Ala Val Met Ile
            35                  40                  45

Pro Pro Gly Gly Thr Glu Cys Phe Trp Gln Phe Ala Tyr Gln Asn Gly
        50                  55                  60

Tyr Phe Tyr Phe Ser Tyr Glu Val Gln Arg Thr Leu Gly Met Ser His
65                  70                  75                  80

Asp Arg His Val Ala Ala Thr Ala His Thr Pro Gln Gly Phe Leu Ile
                85                  90                  95

Asp Ser Ser Gln Asp Val Arg Gly Gln Ile Asn Phe Ser Ile Lys Glu
            100                 105                 110

Thr Gly Phe Tyr Gln Leu Cys Leu Asn Asn Gln Gln Asn His Phe Gly
            115                 120                 125

Ser Val Gln Val Tyr Leu Asn Phe Gly Val Phe Tyr Glu Gly Pro Glu
        130                 135                 140

Met Asp His Lys Gln Lys Asn Glu Arg Lys Gln Leu Asn Asp Thr Leu
145                 150                 155                 160

Asp Ala Ile Glu Glu Ser Thr Gln Lys Met Gln Asn Asn Ile Phe His
                165                 170                 175

Met Trp Arg Tyr Tyr Asn Phe Ala Arg Met Arg Lys Met Ala Asp Phe
            180                 185                 190

Phe Leu Leu Gln Ser Asn Tyr Asn Tyr Val Asn Trp Trp Ser Thr Ala
            195                 200                 205

Gln Ser Phe Val Ile Val Leu Ser Gly Ile Leu Gln Leu Tyr Phe Leu
        210                 215                 220

Lys Arg Leu Phe Asn Val Pro Lys Val Thr Asp Thr Lys Lys Pro Arg
225                 230                 235                 240

Cys

<210> SEQ ID NO 60
<211> LENGTH: 239
<212> TYPE: PRT
<213> ORGANISM: Felis catus

<400> SEQUENCE: 60

Met Phe Pro Leu Leu Ser Gly Ala Gly Leu Val Val Leu Asn Leu Val
1               5                   10                  15

Thr Ser Ala Arg Ser Leu Lys Thr Glu Pro Phe Ile Gly Ser Gly Asp
            20                  25                  30

Gln Pro Leu Phe His Gly Ala Asp Arg Ser Asp Phe Ala Val Met Ile
            35                  40                  45

Pro Pro Gly Gly Thr Glu Cys Phe Trp Gln Phe Ala Tyr Gln Asn Gly
        50                  55                  60

Tyr Phe Tyr Phe Ser Tyr Glu Arg Thr Leu Gly Met Ser His Asp Arg
65                  70                  75                  80
```

```
His Val Ala Ala Thr Ala His Thr Pro Gln Gly Phe Leu Ile Asp Ser
                85                  90                  95

Ser Gln Asp Val Arg Gly Gln Ile Asn Phe Ser Ile Lys Glu Thr Gly
                100                 105                 110

Phe Tyr Gln Leu Cys Leu Asn Asn Gln Gln Asn His Phe Gly Ser Val
                115                 120                 125

Gln Val Tyr Leu Asn Phe Gly Val Phe Tyr Glu Gly Pro Glu Met Asp
        130                 135                 140

His Lys Gln Lys Asn Glu Arg Lys Gln Leu Asn Asp Thr Leu Asp Ala
145                 150                 155                 160

Ile Glu Glu Ser Thr Gln Lys Met Gln Asn Asn Ile Phe His Met Trp
                165                 170                 175

Arg Tyr Tyr Asn Phe Ala Arg Met Arg Lys Met Ala Asp Phe Phe Leu
                180                 185                 190

Leu Gln Ser Asn Tyr Asn Tyr Val Asn Trp Trp Ser Thr Ala Gln Ser
                195                 200                 205

Phe Val Ile Val Leu Ser Gly Ile Leu Gln Leu Tyr Phe Leu Lys Arg
        210                 215                 220

Leu Phe Asn Val Pro Lys Val Thr Asp Thr Lys Lys Pro Arg Cys
225                 230                 235
```

<210> SEQ ID NO 61
<211> LENGTH: 119
<212> TYPE: PRT
<213> ORGANISM: Felis catus

<400> SEQUENCE: 61

```
Met Lys Leu Val Arg Phe Leu Met Lys Leu Ser His Glu Thr Val Thr
1               5                   10                  15

Ile Glu Leu Lys Asn Gly Thr Gln Val His Gly Thr Ile Thr Gly Val
                20                  25                  30

Asp Val Ser Met Asn Thr His Leu Lys Ala Val Lys Met Thr Leu Lys
                35                  40                  45

Asn Arg Glu Pro Val Gln Leu Glu Thr Leu Ser Ile Arg Gly Asn Asn
        50                  55                  60

Ile Arg Tyr Phe Ile Leu Pro Asp Ser Leu Pro Leu Asp Thr Leu Leu
65                  70                  75                  80

Val Asp Val Glu Pro Lys Val Lys Ser Lys Lys Arg Glu Ala Val Ala
                85                  90                  95

Gly Arg Gly Arg Gly Arg Gly Arg Gly Arg Gly Arg Gly Arg Gly Arg
                100                 105                 110

Gly Arg Gly Gly Pro Arg Arg
        115
```

<210> SEQ ID NO 62
<211> LENGTH: 112
<212> TYPE: PRT
<213> ORGANISM: Felis catus

<400> SEQUENCE: 62

```
Met Lys Leu Ser His Glu Thr Val Thr Ile Glu Leu Lys Asn Gly Thr
1               5                   10                  15

Gln Val His Gly Thr Ile Thr Gly Val Asp Val Ser Met Asn Thr His
                20                  25                  30

Leu Lys Ala Val Lys Met Thr Leu Lys Asn Arg Glu Pro Val Gln Leu
                35                  40                  45
```

```
Glu Thr Leu Ser Ile Arg Gly Asn Asn Ile Arg Tyr Phe Ile Leu Pro
    50              55              60

Asp Ser Leu Pro Leu Asp Thr Leu Leu Val Asp Val Glu Pro Lys Val
65              70              75              80

Lys Ser Lys Lys Arg Glu Ala Val Ala Gly Arg Gly Arg Gly Arg Gly
                85              90              95

Arg Gly Arg Gly Arg Gly Arg Gly Arg Gly Arg Gly Gly Pro Arg Arg
                100             105             110
```

<210> SEQ ID NO 63
<211> LENGTH: 213
<212> TYPE: PRT
<213> ORGANISM: Felis catus

<400> SEQUENCE: 63

```
Met Ala Ser Ser Ala Val Ser Gly Leu Ser Arg Gln Val Arg Cys Phe
1               5               10              15

Ser Thr Ser Val Val Arg Pro Phe Ala Lys Leu Val Arg Pro Pro Val
                20              25              30

Gln Ile Tyr Gly Ile Glu Gly Arg Tyr Ala Thr Ala Leu Tyr Ser Ala
        35              40              45

Ala Ser Lys Gln Asn Lys Leu Glu Gln Val Glu Lys Glu Leu Leu Arg
    50              55              60

Val Ala Gln Ile Leu Lys Glu Pro Lys Met Ala Ala Ser Ile Met Asn
65              70              75              80

Pro Tyr Val Lys Arg Ser Val Lys Val Lys Ser Leu Asn Asp Met Thr
                85              90              95

Ala Lys Glu Arg Phe Ser Pro Leu Thr Cys Asn Leu Ile Asn Leu Leu
                100             105             110

Ala Glu Asn Gly Arg Leu Asn Asn Thr Pro Gly Val Val Ser Ala Phe
            115             120             125

Ser Thr Met Met Ser Val His Arg Gly Glu Val Pro Cys Thr Val Thr
    130             135             140

Thr Ala Ser Pro Leu Asp Glu Pro Thr Leu Ala Glu Leu Arg Thr Val
145             150             155             160

Leu Lys Ser Phe Leu Ser Lys Gly Gln Val Leu Lys Leu Glu Val Lys
                165             170             175

Ile Asp Pro Ser Ile Met Gly Gly Met Ile Val Arg Ile Gly Glu Lys
                180             185             190

Tyr Ala Asp Met Ser Ala Lys Thr Lys Ile Gln Lys Leu Ser Arg Ala
            195             200             205

Met Arg Glu Ile Phe
    210
```

<210> SEQ ID NO 64
<211> LENGTH: 519
<212> TYPE: PRT
<213> ORGANISM: Felis catus

<400> SEQUENCE: 64

```
Met Ala Ala Pro Ser Arg Leu Leu Ile Arg Gly Gly Arg Val Val Asn
1               5               10              15

Asp Asp Leu Ser Gln Val Ala Asp Val Leu Val Glu Asp Gly Val Val
                20              25              30

Arg Ala Leu Gly Arg Asp Leu Leu Pro Pro Gly Gly Ala Pro Ala Gly
        35              40              45
```

-continued

```
Leu Arg Val Leu Asp Ala Ala Gly Lys Leu Val Leu Pro Gly Gly Ile
    50                  55                  60

Asp Thr His Thr His Met Gln Phe Pro Phe Met Gly Ala Arg Ser Val
65                  70                  75                  80

Asp Asp Phe His Gln Gly Thr Lys Ala Ala Leu Ala Gly Gly Thr Thr
                85                  90                  95

Met Ile Ile Asp Phe Ala Ile Pro Gln Lys Gly Gly Ser Leu Ile Lys
            100                 105                 110

Ala Phe Glu Thr Trp Arg Ser Trp Ala Asp Pro Lys Val Cys Cys Asp
        115                 120                 125

Tyr Ser Leu His Val Ala Val Thr Trp Trp Ser Asp Gln Val Lys Glu
    130                 135                 140

Glu Met Lys Ile Leu Thr Gln Asp Lys Gly Val Asn Ser Phe Lys Met
145                 150                 155                 160

Phe Met Ala Tyr Lys Asp Leu Tyr Met Val Arg Asp Glu Glu Leu Tyr
                165                 170                 175

Ala Ala Phe Ser Gln Cys Lys Glu Ile Gly Ala Ile Ala Gln Val His
            180                 185                 190

Ala Glu Asn Gly Asp Leu Ile Ala Glu Gly Ala Lys Lys Met Leu Ala
        195                 200                 205

Leu Gly Ile Thr Gly Pro Glu Gly His Glu Leu Cys Arg Pro Glu Ala
    210                 215                 220

Val Glu Ala Glu Ala Thr Leu Arg Ala Ile Thr Ile Ala Ser Ala Val
225                 230                 235                 240

Asn Cys Pro Leu Tyr Ile Val His Val Met Ser Lys Ser Ala Ala Lys
                245                 250                 255

Val Ile Ala Asp Ala Arg Arg Asp Gly Lys Val Val Tyr Gly Glu Pro
            260                 265                 270

Ile Ala Ala Ser Leu Gly Thr Asp Gly Thr His Tyr Trp His Lys Asp
        275                 280                 285

Trp His His Ala Ala His His Val Met Gly Pro Pro Leu Arg Pro Asp
    290                 295                 300

Pro Ser Thr Pro Asp Phe Leu Met Asn Leu Leu Ala Asn Gly Asp Leu
305                 310                 315                 320

Thr Thr Thr Gly Thr Asp His Cys Thr Phe Asn Thr Cys Gln Lys Ala
                325                 330                 335

Leu Gly Lys Asp Asp Phe Thr Lys Ile Pro Asn Gly Val Asn Gly Val
            340                 345                 350

Glu Asp Arg Met Ser Val Ile Trp Glu Lys Gly Val His Ser Gly Lys
        355                 360                 365

Met Asp Glu Asn Arg Phe Val Ala Val Thr Ser Thr Asn Ala Ala Lys
    370                 375                 380

Val Phe Asn Leu Tyr Pro Arg Lys Gly Arg Ile Ala Val Gly Ser Asp
385                 390                 395                 400

Ala Asp Ile Val Ile Trp Asp Pro Lys Ala Thr Arg Thr Ile Ser Ala
                405                 410                 415

Arg Thr His His Gln Ala Val Asn Phe Asn Ile Phe Glu Gly Met Val
            420                 425                 430

Cys His Gly Val Pro Leu Val Thr Ile Ser Arg Gly Lys Val Val Tyr
        435                 440                 445

Glu Ala Gly Val Leu Ser Val Thr Ala Gly Asp Gly Lys Phe Ile Pro
    450                 455                 460
```

-continued

```
Arg Lys Pro Phe Ala Glu Tyr Ile Tyr Lys Arg Ile Lys Gln Arg Asp
465                 470                 475                 480

Gln Thr Cys Thr Pro Thr Pro Val Glu Arg Glu Pro Tyr Lys Gly Glu
                485                 490                 495

Val Val Thr Leu Lys Thr Arg Glu Thr Lys Glu Asp Ala Ala Ala Gly
            500                 505                 510

Thr Arg Lys Gln Ala His Pro
            515

<210> SEQ ID NO 65
<211> LENGTH: 513
<212> TYPE: PRT
<213> ORGANISM: Felis catus

<400> SEQUENCE: 65

Met Ala Ala Pro Ser Arg Leu Leu Ile Arg Gly Gly Arg Val Val Asn
1               5                   10                  15

Asp Asp Leu Ser Gln Val Ala Asp Val Leu Val Glu Asp Gly Val Val
            20                  25                  30

Arg Ala Leu Gly Arg Asp Leu Leu Pro Pro Gly Gly Ala Pro Ala Gly
            35                  40                  45

Leu Arg Val Leu Asp Ala Ala Gly Lys Leu Val Leu Pro Gly Gly Ile
    50                  55                  60

Asp Thr His Thr His Met Gln Phe Pro Phe Met Gly Ala Arg Ser Val
65                  70                  75                  80

Asp Asp Phe His Gln Gly Thr Lys Ala Ala Leu Ala Gly Gly Thr Thr
            85                  90                  95

Met Ile Ile Asp Phe Ala Ile Pro Gln Lys Gly Gly Ser Leu Ile Lys
            100                 105                 110

Ala Phe Glu Thr Trp Arg Ser Trp Ala Asp Pro Lys Val Cys Cys Asp
            115                 120                 125

Tyr Ser Leu His Val Ala Val Thr Trp Trp Ser Asp Gln Val Lys Glu
    130                 135                 140

Glu Met Lys Ile Leu Thr Gln Asp Lys Gly Val Asn Ser Phe Lys Met
145                 150                 155                 160

Phe Met Ala Tyr Lys Asp Leu Tyr Met Val Arg Asp Glu Glu Leu Tyr
            165                 170                 175

Ala Ala Phe Ser Gln Cys Lys Glu Ile Gly Ala Ile Ala Gln Val His
            180                 185                 190

Ala Glu Asn Gly Asp Leu Ile Ala Glu Gly Ala Lys Lys Met Leu Ala
            195                 200                 205

Leu Gly Ile Thr Gly Pro Glu Gly His Glu Leu Cys Arg Pro Glu Ala
    210                 215                 220

Val Glu Ala Glu Ala Thr Leu Arg Ala Ile Thr Ile Ala Ser Ala Val
225                 230                 235                 240

Asn Cys Pro Leu Tyr Ile Val His Val Met Ser Lys Ser Ala Ala Lys
            245                 250                 255

Val Ile Ala Asp Ala Arg Arg Asp Gly Lys Val Val Tyr Gly Glu Pro
            260                 265                 270

Ile Ala Ala Ser Leu Gly Thr Asp Gly Thr His Tyr Trp His Lys Asp
            275                 280                 285

Trp His His Ala Ala His His Val Met Gly Pro Pro Leu Arg Pro Asp
    290                 295                 300

Pro Ser Thr Pro Asp Phe Leu Met Asn Leu Leu Ala Asn Gly Asp Leu
305                 310                 315                 320
```

```
Thr Thr Thr Gly Thr Asp His Cys Thr Phe Asn Thr Cys Gln Lys Ala
            325                 330                 335

Leu Gly Lys Asp Asp Phe Thr Lys Ile Pro Asn Gly Val Asn Gly Val
            340                 345                 350

Glu Asp Arg Met Ser Val Ile Trp Glu Lys Gly Val His Ser Gly Lys
            355                 360                 365

Met Asp Glu Asn Arg Phe Val Ala Val Thr Ser Thr Asn Ala Ala Lys
        370                 375                 380

Val Phe Asn Leu Tyr Pro Arg Lys Gly Arg Ile Ala Val Gly Ser Asp
385                 390                 395                 400

Ala Asp Ile Val Ile Trp Asp Pro Lys Ala Thr Arg Thr Ile Ser Ala
            405                 410                 415

Arg Thr His His Gln Ala Val Asn Phe Asn Ile Phe Glu Gly Met Val
            420                 425                 430

Cys His Gly Val Pro Leu Val Thr Ile Ser Arg Gly Lys Val Val Tyr
            435                 440                 445

Glu Ala Gly Val Leu Ser Val Thr Ala Gly Asp Gly Lys Phe Ile Pro
        450                 455                 460

Arg Lys Pro Phe Ala Glu Tyr Ile Tyr Lys Arg Ile Lys Gln Arg Asp
465                 470                 475                 480

Gln Val Lys Ser Glu Lys Arg Ile Leu Leu Phe Pro Ser Leu Leu Ser
            485                 490                 495

Val Val Ser Pro Trp Arg Asn Arg Pro His Phe Asn Ser Pro Arg Cys
            500                 505                 510

Phe

<210> SEQ ID NO 66
<211> LENGTH: 466
<212> TYPE: PRT
<213> ORGANISM: Mus musculus

<400> SEQUENCE: 66

Met Gly Ala Gly Ala Leu Ala Leu Gly Ala Ser Glu Pro Cys Asn Leu
1               5                   10                  15

Ser Ser Ala Ala Pro Leu Pro Asp Gly Ala Ala Thr Ala Ala Arg Leu
            20                  25                  30

Leu Val Leu Ala Ser Pro Pro Ala Ser Leu Leu Pro Pro Ala Ser Glu
        35                  40                  45

Gly Ser Ala Pro Leu Ser Gln Gln Trp Thr Ala Gly Met Gly Leu Leu
        50                  55                  60

Leu Ala Leu Ile Val Leu Leu Ile Val Val Gly Asn Val Leu Val Ile
65                  70                  75                  80

Val Ala Ile Ala Lys Thr Pro Arg Leu Gln Thr Leu Thr Asn Leu Phe
            85                  90                  95

Ile Met Ser Leu Ala Ser Ala Asp Leu Val Met Gly Leu Leu Val Val
            100                 105                 110

Pro Phe Gly Ala Thr Ile Val Val Trp Gly Arg Trp Glu Tyr Gly Ser
        115                 120                 125

Phe Phe Cys Glu Leu Trp Thr Ser Val Asp Val Leu Cys Val Thr Ala
        130                 135                 140

Ser Ile Glu Thr Leu Cys Val Ile Ala Leu Asp Arg Tyr Leu Ala Ile
145                 150                 155                 160

Thr Ser Pro Phe Arg Tyr Gln Ser Leu Leu Thr Arg Ala Arg Ala Arg
            165                 170                 175
```

-continued

```
Ala Leu Val Cys Thr Val Trp Ala Ile Ser Ala Leu Val Ser Phe Leu
            180                 185                 190

Pro Ile Leu Met His Trp Trp Arg Ala Glu Ser Asp Glu Ala Arg Arg
            195                 200                 205

Cys Tyr Asn Asp Pro Lys Cys Cys Asp Phe Val Thr Asn Arg Ala Tyr
            210                 215                 220

Ala Ile Ala Ser Ser Val Val Ser Phe Tyr Val Pro Leu Cys Ile Met
225                 230                 235                 240

Ala Phe Val Tyr Leu Arg Val Phe Arg Glu Ala Gln Lys Gln Val Lys
                245                 250                 255

Lys Ile Asp Ser Cys Glu Arg Arg Phe Leu Gly Gly Pro Ala Arg Pro
            260                 265                 270

Pro Ser Pro Glu Pro Ser Pro Ser Pro Gly Pro Pro Arg Pro Ala Asp
            275                 280                 285

Ser Leu Ala Asn Gly Arg Ser Ser Lys Arg Arg Pro Ser Arg Leu Val
            290                 295                 300

Ala Leu Arg Glu Gln Lys Ala Leu Lys Thr Leu Gly Ile Ile Met Gly
305                 310                 315                 320

Val Phe Thr Leu Cys Trp Leu Pro Phe Phe Leu Ala Asn Val Val Lys
                325                 330                 335

Ala Phe His Arg Asp Leu Val Pro Asp Arg Leu Phe Val Phe Phe Asn
                340                 345                 350

Trp Leu Gly Tyr Ala Asn Ser Ala Phe Asn Pro Ile Ile Tyr Cys Arg
            355                 360                 365

Ser Pro Asp Phe Arg Lys Ala Phe Gln Arg Leu Leu Cys Cys Ala Arg
            370                 375                 380

Arg Ala Ala Cys Arg Arg Arg Ala Ala His Gly Asp Arg Pro Arg Ala
385                 390                 395                 400

Ser Gly Cys Leu Ala Arg Ala Gly Pro Pro Pro Ser Pro Gly Ala Pro
                405                 410                 415

Ser Asp Asp Asp Asp Asp Asp Ala Gly Thr Thr Pro Pro Ala Arg Leu
            420                 425                 430

Leu Glu Pro Trp Thr Gly Cys Asn Gly Gly Thr Thr Thr Val Asp Ser
            435                 440                 445

Asp Ser Ser Leu Asp Glu Pro Gly Arg Gln Gly Phe Ser Ser Glu Ser
450                 455                 460

Lys Val
465
```

```
<210> SEQ ID NO 67
<211> LENGTH: 477
<212> TYPE: PRT
<213> ORGANISM: Homo sapiens

<400> SEQUENCE: 67
```

```
Met Gly Ala Gly Val Leu Val Leu Gly Ala Ser Glu Pro Gly Asn Leu
1               5                   10                  15

Ser Ser Ala Ala Pro Leu Pro Asp Gly Ala Ala Thr Ala Ala Arg Leu
            20                  25                  30

Leu Val Pro Ala Ser Pro Pro Ala Ser Leu Leu Pro Pro Ala Ser Glu
            35                  40                  45

Ser Pro Glu Pro Leu Ser Gln Gln Trp Thr Ala Gly Met Gly Leu Leu
            50                  55                  60

Met Ala Leu Ile Val Leu Leu Ile Val Ala Gly Asn Val Leu Val Ile
```

-continued

```
65                    70                    75                    80

Val Ala Ile Ala Lys Thr Pro Arg Leu Gln Thr Leu Thr Asn Leu Phe
                85                    90                    95

Ile Met Ser Leu Ala Ser Ala Asp Leu Val Met Gly Leu Leu Val Val
                100                   105                   110

Pro Phe Gly Ala Thr Ile Val Val Trp Gly Arg Trp Glu Tyr Gly Ser
                115                   120                   125

Phe Phe Cys Glu Leu Trp Thr Ser Val Asp Val Leu Cys Val Thr Ala
        130                   135                   140

Ser Ile Glu Thr Leu Cys Val Ile Ala Leu Asp Arg Tyr Leu Ala Ile
145                   150                   155                   160

Thr Ser Pro Phe Arg Tyr Gln Ser Leu Leu Thr Arg Ala Arg Ala Arg
                165                   170                   175

Gly Leu Val Cys Thr Val Trp Ala Ile Ser Ala Leu Val Ser Phe Leu
                180                   185                   190

Pro Ile Leu Met His Trp Trp Arg Ala Glu Ser Asp Glu Ala Arg Arg
                195                   200                   205

Cys Tyr Asn Asp Pro Lys Cys Cys Asp Phe Val Thr Asn Arg Ala Tyr
        210                   215                   220

Ala Ile Ala Ser Ser Val Val Ser Phe Tyr Val Pro Leu Cys Ile Met
225                   230                   235                   240

Ala Phe Val Tyr Leu Arg Val Phe Arg Glu Ala Gln Lys Gln Val Lys
                245                   250                   255

Lys Ile Asp Ser Cys Glu Arg Arg Phe Leu Gly Gly Pro Ala Arg Pro
                260                   265                   270

Pro Ser Pro Ser Pro Ser Pro Val Pro Ala Pro Ala Pro Pro Pro Gly
                275                   280                   285

Pro Pro Arg Pro Ala Ala Ala Ala Ala Thr Ala Pro Leu Ala Asn Gly
        290                   295                   300

Arg Ala Gly Lys Arg Arg Pro Ser Arg Leu Val Ala Leu Arg Glu Gln
305                   310                   315                   320

Lys Ala Leu Lys Thr Leu Gly Ile Ile Met Gly Val Phe Thr Leu Cys
                325                   330                   335

Trp Leu Pro Phe Phe Leu Ala Asn Val Val Lys Ala Phe His Arg Glu
                340                   345                   350

Leu Val Pro Asp Arg Leu Phe Val Phe Phe Asn Trp Leu Gly Tyr Ala
                355                   360                   365

Asn Ser Ala Phe Asn Pro Ile Ile Tyr Cys Arg Ser Pro Asp Phe Arg
        370                   375                   380

Lys Ala Phe Gln Arg Leu Leu Cys Cys Ala Arg Arg Ala Ala Arg Arg
385                   390                   395                   400

Arg His Ala Thr His Gly Asp Arg Pro Arg Ala Ser Gly Cys Leu Ala
                405                   410                   415

Arg Pro Gly Pro Pro Pro Ser Pro Gly Ala Ala Ser Asp Asp Asp Asp
                420                   425                   430

Asp Asp Val Val Gly Ala Thr Pro Pro Ala Arg Leu Leu Glu Pro Trp
                435                   440                   445

Ala Gly Cys Asn Gly Gly Ala Ala Ala Asp Ser Asp Ser Ser Leu Asp
        450                   455                   460

Glu Pro Cys Arg Pro Gly Phe Ala Ser Glu Ser Lys Val
465                   470                   475
```

<210> SEQ ID NO 68

```
<211> LENGTH: 473
<212> TYPE: PRT
<213> ORGANISM: Canis lupus familiaris

<400> SEQUENCE: 68

Met Gly Ala Gly Ala Leu Ala Leu Gly Ala Ser Glu Pro Cys Asn Leu
1               5                   10                  15

Ser Ser Ala Ala Pro Leu Pro Asp Gly Ala Ala Thr Ala Ala Arg Leu
            20                  25                  30

Leu Val Pro Ala Ser Pro Ser Ala Ser Pro Leu Ala Pro Thr Ser Glu
        35                  40                  45

Gly Pro Ala Pro Leu Ser Gln Gln Trp Thr Ala Gly Ile Gly Leu Leu
    50                  55                  60

Met Ala Leu Ile Val Leu Leu Ile Val Ala Gly Asn Val Leu Val Ile
65                  70                  75                  80

Ala Ala Ile Ala Lys Thr Pro Arg Leu Gln Thr Leu Thr Asn Leu Phe
                85                  90                  95

Ile Met Ser Leu Ala Ser Ala Asp Leu Val Met Gly Leu Leu Val Val
            100                 105                 110

Pro Phe Gly Ala Thr Ile Val Met Arg Gly Arg Trp Glu Tyr Gly Ser
        115                 120                 125

Phe Leu Cys Glu Leu Trp Thr Ser Val Asp Val Leu Cys Val Thr Ala
    130                 135                 140

Ser Ile Glu Thr Leu Cys Val Ile Ala Leu Asp Arg Tyr Leu Ala Ile
145                 150                 155                 160

Thr Ala Pro Phe Arg Tyr Gln Ser Leu Leu Thr Arg Ala Arg Ala Arg
                165                 170                 175

Ala Leu Val Cys Thr Val Trp Ala Ile Ser Ala Leu Val Ser Phe Leu
            180                 185                 190

Pro Ile Leu Met His Trp Trp Arg Ala Gly Gly Asp Glu Ala Arg Arg
        195                 200                 205

Cys Tyr Asn Asp Pro Lys Cys Cys Asp Phe Val Thr Asn Arg Ala Tyr
    210                 215                 220

Ala Ile Ala Ser Ser Val Val Ser Phe Tyr Val Pro Leu Cys Ile Met
225                 230                 235                 240

Ala Phe Val Tyr Leu Arg Val Phe Arg Glu Ala Gln Lys Gln Val Lys
                245                 250                 255

Lys Ile Asp Ser Cys Glu Arg Arg Phe Leu Gly Gly Pro Ala Arg Pro
            260                 265                 270

Pro Ala Pro Pro Pro Ala Pro Ala Pro Pro Pro Ala Pro Gly
        275                 280                 285

Ser Pro Arg Pro Ala Ala Ala Ala Pro Leu Ala Asn Gly Arg Val Gly
    290                 295                 300

Arg Arg Arg Pro Ser Arg Leu Val Ala Leu Arg Glu Gln Lys Ala Leu
305                 310                 315                 320

Lys Thr Leu Gly Ile Ile Met Gly Val Phe Thr Leu Cys Trp Leu Pro
                325                 330                 335

Phe Phe Leu Ala Asn Val Val Lys Ala Phe His Arg Asp Leu Val Pro
            340                 345                 350

Asp Arg Leu Phe Val Phe Phe Asn Trp Leu Gly Tyr Ala Asn Ser Ala
        355                 360                 365

Phe Asn Pro Ile Ile Tyr Cys Arg Ser Pro Asp Phe Arg Arg Ala Phe
    370                 375                 380

Gln Arg Leu Leu Cys Cys Ala Arg Arg Ala Ala Arg Gly Ser His Gly
```

-continued

```
385                 390                 395                 400

Ala Ala Gly Asp Pro Pro Arg Ala Arg Pro Pro Pro Ser Pro Gly Ala
                405                 410             415

Ala Ser Asp Asp Asp Asp Asp Asp Glu Asp Asp Ala Gly Ala Gly Ala
                420             425             430

Gly Ala Ala Pro Pro Ala Arg Leu Leu Glu Pro Trp Ala Gly Cys Asn
            435             440             445

Gly Gly Ala Ala Ala Asp Ser Asp Ser Ser Leu Asp Gly Ala Gly Ser
    450             455             460

Pro Ala Gly Ala Ser Glu Ser Arg Val
465             470

<210> SEQ ID NO 69
<211> LENGTH: 474
<212> TYPE: PRT
<213> ORGANISM: Felis catus

<400> SEQUENCE: 69

Met Gly Ala Gly Ala Leu Ala Leu Gly Ala Ser Glu Pro Cys Asn Leu
1               5               10              15

Ser Ser Ala Ala Pro Leu Pro Asp Gly Ala Ala Thr Ala Ala Arg Leu
                20              25              30

Leu Val Pro Ala Ser Pro Ser Ala Ser Pro Leu Thr Pro Thr Ser Glu
            35              40              45

Gly Pro Ala Pro Leu Ser Gln Gln Trp Thr Ala Gly Ile Gly Leu Leu
    50              55              60

Met Ala Leu Ile Val Leu Leu Ile Val Ala Gly Asn Val Leu Val Ile
65              70              75              80

Val Ala Ile Ala Lys Thr Pro Arg Leu Gln Thr Leu Thr Asn Leu Phe
                85              90              95

Ile Met Ser Leu Ala Ser Ala Asp Leu Val Met Gly Leu Leu Val Val
            100             105             110

Pro Phe Gly Ala Thr Ile Val Met Arg Gly Arg Trp Glu Tyr Gly Ser
            115             120             125

Phe Phe Cys Glu Leu Trp Thr Ser Val Asp Val Leu Cys Val Thr Ala
    130             135             140

Ser Ile Glu Thr Leu Cys Val Ile Ala Leu Asp Arg Tyr Leu Ala Ile
145             150             155             160

Thr Ser Pro Phe Arg Tyr Gln Ser Leu Leu Thr Arg Ala Arg Ala Arg
                165             170             175

Ala Leu Val Cys Thr Val Trp Ala Ile Ser Ala Leu Val Ser Phe Leu
            180             185             190

Pro Ile Leu Met His Trp Trp Arg Ala Glu Gly Asp Glu Ala Arg Arg
            195             200             205

Cys Tyr Asn Asp Pro Lys Cys Cys Asp Phe Val Thr Asn Arg Ala Tyr
    210             215             220

Ala Ile Ala Ser Ser Val Val Ser Phe Tyr Val Pro Leu Cys Ile Met
225             230             235             240

Ala Phe Val Tyr Leu Arg Val Phe Arg Glu Ala Gln Lys Gln Val Lys
                245             250             255

Lys Ile Asp Ser Cys Glu Arg Arg Phe Leu Ser Gly Pro Ala Arg Pro
            260             265             270

Pro Ser Pro Ala Pro Ala Pro Gly Ser Pro Arg Pro Ala Ala Thr Ala
            275             280             285
```

-continued

```
Ala Ala Ala Ala Ala Ala Ala Pro Leu Ala Asn Gly Arg Ile Ser Lys
290             295             300

Arg Arg Pro Ser Arg Leu Val Ala Leu Arg Glu Gln Lys Ala Leu Lys
305             310             315             320

Thr Leu Gly Ile Ile Met Gly Val Phe Thr Leu Cys Trp Leu Pro Phe
                325             330             335

Phe Leu Ala Asn Val Val Lys Ala Phe His Arg Asp Leu Val Pro Asp
            340             345             350

Arg Leu Phe Val Phe Phe Asn Trp Leu Gly Tyr Ala Asn Ser Ala Phe
            355             360             365

Asn Pro Ile Ile Tyr Cys Arg Ser Pro Asp Phe Arg Lys Ala Phe Gln
    370             375             380

Arg Leu Leu Cys Phe Ala Arg Arg Ala Ala Arg Gly Gly His Ala Ala
385             390             395             400

Ala Gly Asp Arg Pro Arg Ala Ser Gly Cys Leu Pro Gly Thr Arg Pro
                405             410             415

Pro Pro Ser Pro Gly Ala Ala Ser Asp Glu Asp Asp Asp Asp Val
                420             425             430

Gly Ala Ala Pro Pro Ala Arg Leu Leu Glu Pro Trp Ala Gly Cys Asn
            435             440             445

Gly Gly Ala Ala Ala Ala Asp Ser Asp Ser Ser Leu Asp Glu Pro Gly
    450             455             460

Arg Pro Ala Gly Ala Ser Glu Ser Lys Val
465             470
```

```
<210> SEQ ID NO 70
<211> LENGTH: 255
<212> TYPE: PRT
<213> ORGANISM: Mus musculus

<400> SEQUENCE: 70

Met Asp Asp Arg Glu Asp Leu Val Tyr Gln Ala Lys Leu Ala Glu Gln
1               5               10              15

Ala Glu Arg Tyr Asp Glu Met Val Glu Ser Met Lys Lys Val Ala Gly
            20              25              30

Met Asp Val Glu Leu Thr Val Glu Glu Arg Asn Leu Leu Ser Val Ala
            35              40              45

Tyr Lys Asn Val Ile Gly Ala Arg Arg Ala Ser Trp Arg Ile Ile Ser
    50              55              60

Ser Ile Glu Gln Lys Glu Glu Asn Lys Gly Gly Glu Asp Lys Leu Lys
65              70              75              80

Met Ile Arg Glu Tyr Arg Gln Met Val Glu Thr Glu Leu Lys Leu Ile
                85              90              95

Cys Cys Asp Ile Leu Asp Val Leu Asp Lys His Leu Ile Pro Ala Ala
            100             105             110

Asn Thr Gly Glu Ser Lys Val Phe Tyr Tyr Lys Met Lys Gly Asp Tyr
            115             120             125

His Arg Tyr Leu Ala Glu Phe Ala Thr Gly Asn Asp Arg Lys Glu Ala
    130             135             140

Ala Glu Asn Ser Leu Val Ala Tyr Lys Ala Ala Ser Asp Ile Ala Met
145             150             155             160

Thr Glu Leu Pro Pro Thr His Pro Ile Arg Leu Gly Leu Ala Leu Asn
                165             170             175

Phe Ser Val Phe Tyr Tyr Glu Ile Leu Asn Ser Pro Asp Arg Ala Cys
            180             185             190
```

-continued

Arg Leu Ala Lys Ala Ala Phe Asp Asp Ala Ile Ala Glu Leu Asp Thr
        195                 200                 205

Leu Ser Glu Glu Ser Tyr Lys Asp Ser Thr Leu Ile Met Gln Leu Leu
        210                 215                 220

Arg Asp Asn Leu Thr Leu Trp Thr Ser Asp Met Gln Gly Asp Gly Glu
225                 230                 235                 240

Glu Gln Asn Lys Glu Ala Leu Gln Asp Val Glu Asp Glu Asn Gln
                245                 250                 255

<210> SEQ ID NO 71
<211> LENGTH: 246
<212> TYPE: PRT
<213> ORGANISM: Mus musculus

<400> SEQUENCE: 71

Met Thr Met Asp Lys Ser Glu Leu Val Gln Lys Ala Lys Leu Ala Glu
1               5                   10                  15

Gln Ala Glu Arg Tyr Asp Asp Met Ala Ala Ala Met Lys Ala Val Thr
                20                  25                  30

Glu Gln Gly His Glu Leu Ser Asn Glu Glu Arg Asn Leu Leu Ser Val
        35                  40                  45

Ala Tyr Lys Asn Val Val Gly Ala Arg Arg Ser Ser Trp Arg Val Ile
        50                  55                  60

Ser Ser Ile Glu Gln Lys Thr Glu Arg Asn Glu Lys Lys Gln Gln Met
65                  70                  75                  80

Gly Lys Glu Tyr Arg Glu Lys Ile Glu Ala Glu Leu Gln Asp Ile Cys
                85                  90                  95

Asn Asp Val Leu Glu Leu Leu Asp Lys Tyr Leu Ile Leu Asn Ala Thr
                100                 105                 110

Gln Ala Glu Ser Lys Val Phe Tyr Leu Lys Met Lys Gly Asp Tyr Phe
        115                 120                 125

Arg Tyr Leu Ser Glu Val Ala Ser Gly Glu Asn Lys Gln Thr Thr Val
        130                 135                 140

Ser Asn Ser Gln Gln Ala Tyr Gln Glu Ala Phe Glu Ile Ser Lys Lys
145                 150                 155                 160

Glu Met Gln Pro Thr His Pro Ile Arg Leu Gly Leu Ala Leu Asn Phe
                165                 170                 175

Ser Val Phe Tyr Tyr Glu Ile Leu Asn Ser Pro Glu Lys Ala Cys Ser
                180                 185                 190

Leu Ala Lys Thr Ala Phe Asp Glu Ala Ile Ala Glu Leu Asp Thr Leu
        195                 200                 205

Asn Glu Glu Ser Tyr Lys Asp Ser Thr Leu Ile Met Gln Leu Leu Arg
        210                 215                 220

Asp Asn Leu Thr Leu Trp Thr Ser Glu Asn Gln Gly Asp Glu Gly Asp
225                 230                 235                 240

Ala Gly Glu Gly Glu Asn
                245

<210> SEQ ID NO 72
<211> LENGTH: 245
<212> TYPE: PRT
<213> ORGANISM: Mus musculus

<400> SEQUENCE: 72

Met Asp Lys Asn Glu Leu Val Gln Lys Ala Lys Leu Ala Glu Gln Ala
1               5                   10                  15

-continued

Glu Arg Tyr Asp Asp Met Ala Ala Cys Met Lys Ser Val Thr Glu Gln
              20                  25                  30

Gly Ala Glu Leu Ser Asn Glu Glu Arg Asn Leu Leu Ser Val Ala Tyr
              35                  40                  45

Lys Asn Val Val Gly Ala Arg Arg Ser Ser Trp Arg Val Val Ser Ser
              50                  55                  60

Ile Glu Gln Lys Thr Glu Gly Ala Glu Lys Lys Gln Gln Met Ala Arg
65                  70                  75                  80

Glu Tyr Arg Glu Lys Ile Glu Thr Glu Leu Arg Asp Ile Cys Asn Asp
                  85                  90                  95

Val Leu Ser Leu Leu Glu Lys Phe Leu Ile Pro Asn Ala Ser Gln Pro
              100                 105                 110

Glu Ser Lys Val Phe Tyr Leu Lys Met Lys Gly Asp Tyr Tyr Arg Tyr
              115                 120                 125

Leu Ala Glu Val Ala Ala Gly Asp Asp Lys Lys Gly Ile Val Asp Gln
              130                 135                 140

Ser Gln Gln Ala Tyr Gln Glu Ala Phe Glu Ile Ser Lys Lys Glu Met
145                 150                 155                 160

Gln Pro Thr His Pro Ile Arg Leu Gly Leu Ala Leu Asn Phe Ser Val
                  165                 170                 175

Phe Tyr Tyr Glu Ile Leu Asn Ser Pro Glu Lys Ala Cys Ser Leu Ala
                  180                 185                 190

Lys Thr Ala Phe Asp Glu Ala Ile Ala Glu Leu Asp Thr Leu Ser Glu
                  195                 200                 205

Glu Ser Tyr Lys Asp Ser Thr Leu Ile Met Gln Leu Leu Arg Asp Asn
              210                 215                 220

Leu Thr Leu Trp Thr Ser Asp Thr Gln Gly Asp Glu Ala Glu Ala Gly
225                 230                 235                 240

Glu Gly Gly Glu Asn
                  245

<210> SEQ ID NO 73
<211> LENGTH: 245
<212> TYPE: PRT
<213> ORGANISM: Mus musculus

<400> SEQUENCE: 73

Met Glu Lys Thr Glu Leu Ile Gln Lys Ala Lys Leu Ala Glu Gln Ala
1                   5                   10                  15

Glu Arg Tyr Asp Asp Met Ala Thr Cys Met Lys Ala Val Thr Glu Gln
              20                  25                  30

Gly Ala Glu Leu Ser Asn Glu Glu Arg Asn Leu Leu Ser Val Ala Tyr
              35                  40                  45

Lys Asn Val Val Gly Gly Arg Arg Ser Ala Trp Arg Val Ile Ser Ser
              50                  55                  60

Ile Glu Gln Lys Thr Asp Thr Ser Asp Lys Lys Leu Gln Leu Ile Lys
65                  70                  75                  80

Asp Tyr Arg Glu Lys Val Glu Ser Glu Leu Arg Ser Ile Cys Thr Thr
                  85                  90                  95

Val Leu Glu Leu Leu Asp Lys Tyr Leu Ile Ala Asn Ala Thr Asn Pro
              100                 105                 110

Glu Ser Lys Val Phe Tyr Leu Lys Met Lys Gly Asp Tyr Phe Arg Tyr
              115                 120                 125

Leu Ala Glu Val Ala Cys Gly Asp Asp Arg Lys Gln Thr Ile Glu Asn

-continued

```
        130                    135                    140

Ser Gln Gly Ala Tyr Gln Glu Ala Phe Asp Ile Ser Lys Lys Glu Met
145                 150                 155                 160

Gln Pro Thr His Pro Ile Arg Leu Gly Leu Ala Leu Asn Phe Ser Val
                165                 170                 175

Phe Tyr Tyr Glu Ile Leu Asn Asn Pro Glu Leu Ala Cys Thr Leu Ala
            180                 185                 190

Lys Thr Ala Phe Asp Glu Ala Ile Ala Glu Leu Asp Thr Leu Asn Glu
        195                 200                 205

Asp Ser Tyr Lys Asp Ser Thr Leu Ile Met Gln Leu Leu Arg Asp Asn
    210                 215                 220

Leu Thr Leu Trp Thr Ser Asp Ser Ala Gly Glu Glu Cys Asp Ala Ala
225                 230                 235                 240

Glu Gly Ala Glu Asn
                245
```

<210> SEQ ID NO 74
<211> LENGTH: 246
<212> TYPE: PRT
<213> ORGANISM: Mus musculus

<400> SEQUENCE: 74

```
Met Gly Asp Arg Glu Gln Leu Leu Gln Arg Ala Arg Leu Ala Glu Gln
1               5                   10                  15

Ala Glu Arg Tyr Asp Asp Met Ala Ser Ala Met Lys Ala Val Thr Glu
                20                  25                  30

Leu Asn Glu Pro Leu Ser Asn Glu Asp Arg Asn Leu Leu Ser Val Ala
            35                  40                  45

Tyr Lys Asn Val Val Gly Ala Arg Arg Ser Ser Trp Arg Val Ile Ser
    50                  55                  60

Ser Ile Glu Gln Lys Thr Met Ala Asp Gly Asn Glu Lys Lys Leu Glu
65                  70                  75                  80

Lys Val Lys Ala Tyr Arg Glu Lys Ile Glu Lys Glu Leu Glu Thr Val
                85                  90                  95

Cys Asn Asp Val Leu Ala Leu Leu Asp Lys Phe Leu Ile Lys Asn Cys
            100                 105                 110

Asn Asp Phe Gln Tyr Glu Ser Lys Val Phe Tyr Leu Lys Met Lys Gly
        115                 120                 125

Asp Tyr Tyr Arg Tyr Leu Ala Glu Val Ala Ser Gly Glu Lys Lys Asn
    130                 135                 140

Ser Val Val Glu Ala Ser Glu Ala Ala Tyr Lys Glu Ala Phe Glu Ile
145                 150                 155                 160

Ser Lys Glu His Met Gln Pro Thr His Pro Ile Arg Leu Gly Leu Ala
                165                 170                 175

Leu Asn Phe Ser Val Phe Tyr Tyr Glu Ile Gln Asn Ala Pro Glu Gln
            180                 185                 190

Ala Cys Leu Leu Ala Lys Gln Ala Phe Asp Asp Ala Ile Ala Glu Leu
        195                 200                 205

Asp Thr Leu Asn Glu Asp Ser Tyr Lys Asp Ser Thr Leu Ile Met Gln
    210                 215                 220

Leu Leu Arg Asp Asn Leu Thr Leu Trp Thr Ser Asp Gln Gln Asp Glu
225                 230                 235                 240

Glu Ala Gly Glu Gly Asn
                245
```

-continued

<210> SEQ ID NO 75
<211> LENGTH: 247
<212> TYPE: PRT
<213> ORGANISM: Mus musculus

<400> SEQUENCE: 75

```
Met Val Asp Arg Glu Gln Leu Val Gln Lys Ala Arg Leu Ala Glu Gln
1               5                   10                  15

Ala Glu Arg Tyr Asp Asp Met Ala Ala Ala Met Lys Asn Val Thr Glu
                20                  25                  30

Leu Asn Glu Pro Leu Ser Asn Glu Glu Arg Asn Leu Leu Ser Val Ala
            35                  40                  45

Tyr Lys Asn Val Val Gly Ala Arg Arg Ser Ser Trp Arg Val Ile Ser
        50                  55                  60

Ser Ile Glu Gln Lys Thr Ser Ala Asp Gly Asn Glu Lys Lys Ile Glu
65                  70                  75                  80

Met Val Arg Ala Tyr Arg Glu Lys Ile Glu Lys Glu Leu Glu Ala Val
                85                  90                  95

Cys Gln Asp Val Leu Ser Leu Leu Asp Asn Tyr Leu Ile Lys Asn Cys
                100                 105                 110

Ser Glu Thr Gln Tyr Glu Ser Lys Val Phe Tyr Leu Lys Met Lys Gly
            115                 120                 125

Asp Tyr Tyr Arg Tyr Leu Ala Glu Val Ala Thr Gly Glu Lys Arg Ala
        130                 135                 140

Thr Val Val Glu Ser Ser Glu Lys Ala Tyr Ser Glu Ala His Glu Ile
145                 150                 155                 160

Ser Lys Glu His Met Gln Pro Thr His Pro Ile Arg Leu Gly Leu Ala
                165                 170                 175

Leu Asn Tyr Ser Val Phe Tyr Tyr Glu Ile Gln Asn Ala Pro Glu Gln
                180                 185                 190

Ala Cys His Leu Ala Lys Thr Ala Phe Asp Asp Ala Ile Ala Glu Leu
            195                 200                 205

Asp Thr Leu Asn Glu Asp Ser Tyr Lys Asp Ser Thr Leu Ile Met Gln
        210                 215                 220

Leu Leu Arg Asp Asn Leu Thr Leu Trp Thr Ser Asp Gln Gln Asp Asp
225                 230                 235                 240

Asp Gly Gly Glu Gly Asn Asn
                245
```

<210> SEQ ID NO 76
<211> LENGTH: 248
<212> TYPE: PRT
<213> ORGANISM: Mus musculus

<400> SEQUENCE: 76

```
Met Glu Arg Ala Ser Leu Ile Gln Lys Ala Lys Leu Ala Glu Gln Ala
1               5                   10                  15

Glu Arg Tyr Glu Asp Met Ala Ala Phe Met Lys Ser Ala Val Glu Lys
                20                  25                  30

Gly Glu Glu Leu Ser Cys Glu Glu Arg Asn Leu Leu Ser Val Ala Tyr
            35                  40                  45

Lys Asn Val Val Gly Gly Gln Arg Ala Ala Trp Arg Val Leu Ser Ser
        50                  55                  60

Ile Glu Gln Lys Ser Asn Glu Glu Gly Ser Glu Glu Lys Gly Pro Glu
65                  70                  75                  80
```

-continued

Val Lys Glu Tyr Arg Glu Lys Val Glu Thr Glu Leu Arg Gly Val Cys
                    85              90              95

Asp Thr Val Leu Gly Leu Leu Asp Ser His Leu Ile Lys Gly Ala Gly
                100             105             110

Asp Ala Glu Ser Arg Val Phe Tyr Leu Lys Met Lys Gly Asp Tyr Tyr
                115             120             125

Arg Tyr Leu Ala Glu Val Ala Thr Gly Asp Asp Lys Lys Arg Ile Ile
        130             135             140

Asp Ser Ala Arg Ser Ala Tyr Gln Glu Ala Met Asp Ile Ser Lys Lys
145             150             155             160

Glu Met Pro Pro Thr Asn Pro Ile Arg Leu Gly Leu Ala Leu Asn Phe
                165             170             175

Ser Val Phe His Tyr Glu Ile Ala Asn Ser Pro Glu Glu Ala Ile Ser
                180             185             190

Leu Ala Lys Thr Thr Phe Asp Glu Ala Met Ala Asp Leu His Thr Leu
                195             200             205

Ser Glu Asp Ser Tyr Lys Asp Ser Thr Leu Ile Met Gln Leu Leu Arg
        210             215             220

Asp Asn Leu Thr Leu Trp Thr Ala Asp Ser Ala Gly Glu Glu Gly Gly
225             230             235             240

Glu Ala Pro Glu Glu Pro Gln Ser
                245

<210> SEQ ID NO 77
<211> LENGTH: 492
<212> TYPE: PRT
<213> ORGANISM: Mus musculus

<400> SEQUENCE: 77

Met Gly Ala Gly Gly Pro Arg Arg Gly Ala Gly Pro Pro Asp Gly Gly
1               5               10              15

Trp Gly Trp Val Val Leu Gly Ala Cys Phe Val Val Thr Gly Phe Ala
                20              25              30

Tyr Gly Phe Pro Lys Ala Val Ser Val Phe Phe Arg Glu Leu Lys Arg
        35              40              45

Asp Phe Gly Ala Gly Tyr Ser Asp Thr Ala Trp Val Ser Ser Ile Met
    50              55              60

Leu Ala Met Leu Tyr Gly Thr Gly Pro Leu Ser Ser Ile Leu Val Thr
65              70              75              80

Arg Phe Gly Cys Arg Pro Val Met Leu Ala Gly Gly Leu Leu Ala Ser
                85              90              95

Ala Gly Met Ile Leu Ala Ser Phe Ala Ser Arg Leu Val Glu Leu Tyr
                100             105             110

Leu Thr Ala Gly Val Leu Thr Gly Leu Gly Leu Ala Leu Asn Phe Gln
                115             120             125

Pro Ser Leu Ile Met Leu Gly Leu Tyr Phe Glu Arg Arg Arg Pro Leu
        130             135             140

Ala Asn Gly Leu Ala Ala Ala Gly Ser Pro Val Phe Leu Ser Met Leu
145             150             155             160

Ser Pro Leu Gly Gln Leu Leu Gly Glu Arg Phe Gly Trp Arg Gly Gly
                165             170             175

Phe Leu Leu Phe Gly Gly Leu Leu Leu His Cys Cys Ala Cys Gly Ala
                180             185             190

Val Met Arg Pro Pro Pro Gly Pro Pro Arg Arg Asp Pro Ser Pro
                195             200             205

-continued

```
His Gly Gly Pro Ala Arg Arg Arg Arg Leu Leu Asp Val Ala Val Cys
    210             215                 220

Thr Asp Arg Ala Phe Val Val Tyr Val Val Thr Lys Phe Leu Met Ala
225                 230                 235                 240

Leu Gly Leu Phe Val Pro Ala Ile Leu Leu Val Asn Tyr Ala Lys Asp
                245                 250                 255

Ala Gly Val Pro Asp Ala Glu Ala Ala Phe Leu Leu Ser Ile Val Gly
                260                 265                 270

Phe Val Asp Ile Val Ala Arg Pro Ala Cys Gly Ala Leu Ala Gly Leu
                275                 280                 285

Gly Arg Leu Arg Pro His Val Pro Tyr Leu Phe Ser Leu Ala Leu Leu
    290                 295                 300

Ala Asn Gly Leu Thr Asp Leu Ile Ser Ala Arg Ala Arg Ser Tyr Gly
305                 310                 315                 320

Thr Leu Val Ala Phe Cys Ile Ala Phe Gly Leu Ser Tyr Gly Met Val
                325                 330                 335

Gly Ala Leu Gln Phe Glu Val Leu Met Ala Thr Val Gly Ala Pro Arg
                340                 345                 350

Phe Pro Ser Ala Leu Gly Leu Val Leu Leu Val Glu Ala Val Ala Val
                355                 360                 365

Leu Ile Gly Pro Pro Ser Ala Gly Arg Leu Val Asp Ala Leu Lys Asn
    370                 375                 380

Tyr Glu Ile Ile Phe Tyr Leu Ala Gly Ser Glu Val Ala Leu Ala Gly
385                 390                 395                 400

Val Phe Met Ala Val Thr Thr Tyr Cys Cys Leu Arg Cys Ser Lys Asn
                405                 410                 415

Ile Ser Ser Gly Arg Ser Ala Glu Gly Gly Ala Ser Asp Pro Glu Asp
                420                 425                 430

Val Glu Ala Glu Arg Asp Ser Glu Pro Met Pro Ala Ser Thr Glu Glu
                435                 440                 445

Pro Gly Ser Leu Glu Ala Leu Glu Val Leu Ser Pro Arg Ala Gly Ser
    450                 455                 460

Pro Glu Gln Glu Pro Glu Glu Glu Ala Val Pro Glu Leu Asp His Glu
465                 470                 475                 480

Ser Ile Gly Gly His Glu Ala Arg Gly Gln Lys Ala
                485                 490
```

<210> SEQ ID NO 78
<211> LENGTH: 470
<212> TYPE: PRT
<213> ORGANISM: Mus musculus

<400> SEQUENCE: 78

```
Met Gly Gly Ala Val Val Asp Glu Gly Pro Thr Gly Ile Lys Ala Pro
1               5                   10                  15

Asp Gly Gly Trp Gly Trp Ala Val Leu Phe Gly Cys Phe Ile Ile Thr
                20                  25                  30

Gly Phe Ser Tyr Ala Phe Pro Lys Ala Val Ser Val Phe Phe Lys Glu
        35                  40                  45

Leu Met His Glu Phe Gly Ile Gly Tyr Ser Asp Thr Ala Trp Ile Ser
    50                  55                  60

Ser Ile Leu Leu Ala Met Leu Tyr Gly Thr Gly Pro Leu Cys Ser Val
65                  70                  75                  80

Cys Val Asn Arg Phe Gly Cys Arg Pro Val Met Leu Val Gly Gly Leu
```

-continued

```
              85                    90                    95

Phe Ala Ser Leu Gly Met Val Ala Ala Ser Phe Cys Arg Ser Ile Ile
            100                   105                   110

Gln Ile Tyr Leu Thr Thr Gly Val Ile Thr Gly Leu Gly Leu Ala Leu
            115                   120                   125

Asn Phe Gln Pro Ser Leu Ile Met Leu Asn Arg Tyr Phe Asn Lys Arg
        130                   135                   140

Arg Pro Ile Ala Asn Gly Leu Ala Ala Ala Gly Ser Pro Val Phe Leu
145                   150                   155                   160

Cys Ala Leu Ser Pro Leu Gly Gln Leu Leu Gln Asp His Tyr Gly Trp
                165                   170                   175

Arg Gly Gly Phe Leu Ile Leu Gly Gly Leu Leu Leu Asn Cys Cys Val
                180                   185                   190

Cys Ala Ala Leu Met Arg Pro Leu Val Ala Pro Gln Val Gly Gly Gly
                195                   200                   205

Thr Glu Pro Arg Gly Pro Gln Arg Pro Pro Gln Arg Leu Leu Asp Leu
        210                   215                   220

Ser Val Phe Arg Asp Arg Gly Phe Leu Ile Tyr Ala Val Ala Ala Ser
225                   230                   235                   240

Ile Met Val Leu Gly Leu Phe Val Pro Pro Val Phe Val Val Ser Tyr
                245                   250                   255

Ala Lys Asp Met Gly Val Pro Asp Thr Lys Ala Ala Phe Leu Leu Thr
                260                   265                   270

Ile Leu Gly Phe Ile Asp Ile Phe Ala Arg Pro Thr Ala Gly Phe Ile
                275                   280                   285

Thr Gly Leu Lys Lys Val Arg Pro Tyr Ser Val Tyr Leu Phe Ser Phe
        290                   295                   300

Ala Met Phe Phe Asn Gly Phe Thr Asp Leu Thr Gly Ser Thr Ala Thr
305                   310                   315                   320

Asp Tyr Gly Gly Leu Val Val Phe Cys Ile Phe Phe Gly Ile Ser Tyr
                325                   330                   335

Gly Met Val Gly Ala Leu Gln Phe Glu Val Leu Met Ala Ile Val Gly
                340                   345                   350

Thr Gln Lys Phe Ser Ser Ala Ile Gly Leu Val Leu Leu Leu Glu Ala
        355                   360                   365

Val Ala Val Leu Ile Gly Pro Pro Ser Gly Gly Lys Leu Leu Asp Ala
        370                   375                   380

Thr Lys Val Tyr Lys Tyr Val Phe Ile Leu Ala Gly Ala Glu Val Leu
385                   390                   395                   400

Thr Ser Ser Leu Val Leu Leu Leu Gly Asn Phe Phe Cys Ile Gly Lys
                405                   410                   415

Arg Lys Arg Pro Glu Val Thr Glu Pro Glu Glu Val Ala Ser Glu Glu
            420                   425                   430

Lys Leu His Lys Pro Pro Val Asp Val Gly Val Asp Ser Arg Glu Val
        435                   440                   445

Glu His Phe Leu Lys Ala Glu Pro Glu Lys Asn Gly Glu Val Val His
        450                   455                   460

Thr Pro Glu Thr Ser Val
465                   470

<210> SEQ ID NO 79
<211> LENGTH: 119
<212> TYPE: PRT
<213> ORGANISM: Mus musculus
```

-continued

```
<400> SEQUENCE: 79

Met Lys Leu Val Arg Phe Leu Met Lys Leu Ser His Glu Thr Val Thr
1               5                   10                  15

Ile Glu Leu Lys Asn Gly Thr Gln Val His Gly Thr Ile Thr Gly Val
                20                  25                  30

Asp Val Ser Met Asn Thr His Leu Lys Ala Val Lys Met Thr Leu Lys
            35                  40                  45

Asn Arg Glu Pro Val Gln Leu Glu Thr Leu Ser Ile Arg Gly Asn Asn
        50                  55                  60

Ile Arg Tyr Phe Ile Leu Pro Asp Ser Leu Pro Leu Asp Thr Leu Leu
65                  70                  75                  80

Val Asp Val Glu Pro Lys Val Lys Ser Lys Lys Arg Glu Ala Val Ala
                85                  90                  95

Gly Arg Gly Arg Gly Arg Gly Arg Gly Arg Gly Arg Gly Arg Gly Arg
                100                 105                 110

Gly Arg Gly Gly Pro Arg Arg
        115

<210> SEQ ID NO 80
<211> LENGTH: 213
<212> TYPE: PRT
<213> ORGANISM: Mus musculus

<400> SEQUENCE: 80

Met Ala Ala Pro Ala Ala Ser Gly Leu Ser Arg Gln Val Arg Ser Phe
1               5                   10                  15

Ser Thr Ser Val Val Arg Pro Phe Ala Lys Leu Val Arg Pro Pro Val
                20                  25                  30

Gln Val Tyr Gly Ile Glu Gly Arg Tyr Ala Thr Ala Leu Tyr Ser Ala
            35                  40                  45

Ala Ser Lys Glu Lys Lys Leu Asp Gln Val Glu Lys Glu Leu Leu Arg
        50                  55                  60

Val Gly Gln Leu Leu Lys Asp Pro Lys Val Ser Leu Ala Val Leu Asn
65                  70                  75                  80

Pro Tyr Ile Lys Arg Thr Val Lys Val Lys Ser Leu Asn Asp Ile Thr
                85                  90                  95

Lys Arg Glu Lys Phe Ser Pro Leu Thr Ala Asn Leu Met Asn Leu Leu
                100                 105                 110

Ala Glu Asn Gly Arg Leu Gly Asn Thr Gln Gly Ile Ile Ser Ala Phe
            115                 120                 125

Ser Thr Ile Met Ser Val His Arg Gly Glu Val Pro Cys Thr Val Thr
        130                 135                 140

Thr Ala Ser Pro Leu Asp Asp Ala Val Leu Ser Glu Leu Lys Thr Val
145                 150                 155                 160

Leu Lys Ser Phe Leu Ser Pro Asn Gln Ile Leu Lys Leu Glu Ile Lys
                165                 170                 175

Thr Asp Pro Ser Ile Met Gly Gly Met Ile Val Arg Ile Gly Glu Lys
                180                 185                 190

Tyr Val Asp Met Ser Ala Lys Ser Lys Ile Gln Lys Leu Ser Lys Ala
            195                 200                 205

Met Arg Glu Met Leu
        210
```